United States Patent
Achilefu

(10) Patent No.: US 8,053,415 B2
(45) Date of Patent: Nov. 8, 2011

(54) COMPOUNDS HAVING RD TARGETING MOTIFS

(75) Inventor: Samuel Achilefu, St. Louis, MO (US)

(73) Assignee: Washington University in St. Louis, St. Louis, MO (US)

(*) Notice: Subject to any disclaimer, the term of this patent is extended or adjusted under 35 U.S.C. 154(b) by 649 days.

(21) Appl. No.: 11/814,215

(22) PCT Filed: Jan. 20, 2006

(86) PCT No.: PCT/US2006/002056
§ 371 (c)(1), (2), (4) Date: Sep. 18, 2008

(87) PCT Pub. No.: WO2006/078914
PCT Pub. Date: Jul. 27, 2006

(65) Prior Publication Data
US 2009/0028788 A1    Jan. 29, 2009

Related U.S. Application Data

(60) Provisional application No. 60/645,816, filed on Jan. 21, 2005.

(51) Int. Cl.
  *A61K 38/08* (2006.01)
  *A61B 5/055* (2006.01)
(52) U.S. Cl. ........ 514/21.8; 530/329; 424/9.3; 536/26.6
(58) Field of Classification Search .................. None
  See application file for complete search history.

(56) References Cited

U.S. PATENT DOCUMENTS

| | | | |
|---|---|---|---|
| 5,972,890 A * | 10/1999 | Lees et al. ................... | 514/13 |
| 6,358,920 B1 * | 3/2002 | Blaschuk et al. ............ | 514/19.1 |
| 6,491,894 B1 | 12/2002 | Ruoslahti et al. | |
| 6,610,651 B1 * | 8/2003 | Ruoslahti et al. .......... | 514/3.7 |
| 2002/0041898 A1 * | 4/2002 | Unger et al. ................ | 424/486 |

FOREIGN PATENT DOCUMENTS

WO     2006078914 A1    7/2006

OTHER PUBLICATIONS

Bugaj 2001, Journal of Biomedical Optics, 6, 122-133.*
International Search Report dated Aug. 2, 2007; 7 pages.
International Search Report regarding PCT/US06/02056, dated May 24, 2006; 5 pages.
Achilefu, S., Lighting up tumors with receptor-specific optical molecular probes, Technol. Cancer Res. Treat., 2004, pp. 393-409, vol. 3, No. 4.
Achilefu, S. et al, Novel receptor-targeted fluorescent contrast agents for in vivo tumor imaging, Invest Radiol, 2000, pp. 479-85, vol. 35, No. 8.
Achilefu, S, et al, Synthesis, in vitro receptor binding, and in vivo evaluation of fluorescein and carbocyanine peptide-based contrast agents, J. Med. Chem., 2002, pp. 2003-15, vol. 45m No. 10.
Achilefu, S, et al, Synergistic effects of light-emitting probes and peptides for targeting and monitoring intergrin expression, PNAS, 2005, pp. 7976-7981, vol. 102, No. 22.
Allman, R, et al, In vitro and in vivo effects of a cyclic peptide with affinity for the alpha(nu)beta3 integrin in human melanoma cells, Eur J Cancer, 2000, pp. 410-22. vol. 36, No. 3.
Arap, W, et al, Cancer treatment by targeted drug delivery to tumor vasculature in a mouse model, Science, 1998, pp. 377-80, vol. 279, No. 5349.
Arnaout, Ma, Integrin structure: new twists and turns in dynamic cell adhesion, Immunol Rev, 2002, pp. 125-40, vol. 186.
Arnaout, Ma, et al, Coming to grips with integrin binding to ligands, Curr Opin Cell Biol, 2002, pp. 641-51, vol. 14, No. 5.
Bloch, et al, Targeting Beta-3 Integrin Using a Linear Hexapeptide Labeled with a Near-Infrared Fluorescent Molecular Probe, Molecular Pharmaceutics, 2006, pp. 539-549. vol. 3, No. 5.
Bloch, et al, Whole-body fluorescence lifetime imaging of a tumor-targeted near-infrared molecular probe in mice. J Biomed Opt., 2005, pp. 054003-1-054003-8, vol. 10, No. 5.
Bugaj, J, et al, Novel fluorescent contrast agents for optical imaging of in vivo tumors based on a receptor-targeted dye-peptide conjugate platform, J. Biomed Opt., 2001, pp. 122-33, vol. 6, No. 2.
Haubner, R, et al, Glycosylated RGD-Containing Peptides: Tracer for Tumor Targeting and Angiogenesis Imaging with Improved Biokinetics, The Journal of Nuclear Medicine, 2001, pp. 326-336, vol. 42, No. 2.
Haubner, R, et al, Radiolabeled αvβ3 Integrin Antagonists: A New Class of Tracers for Tumor Targeting, J Nucl Med, 1999, pp. 1061-1071, vol. 40.
Haubner, R, et al, Noninvasve Imaging of αvβ3 Integrin Expression Using 18F-labled RGD-containing Glycopeptide and Positron Emission Tomography, Cancer Research, 2001, pp. 1781-1785, vol. 61.
Janssen, M, et al, Tumor Targeting with Radiolabeled αvβ3 Integrin Binding Peptides in a Nude Mouse Model, Cancer Research, 2002, pp. 6146-6151, vol. 62.
Sivolapenko, GB, et al, Imaging of metastatic melanoma utilising a technetium-99m labelled RGD-containing synthetic peptide, Eur J Nucl Med, 1998, pp. 1383-1389, vol. 25, No. 10.
Van Hagen, PM, et al, Evaluation of a radiolabelled cyclic DTPA-RGD analogue for tumour imaging and radionuclide therapy, Int J Cancer, 2000, pp. 186-198, vol. 90, No. 4.
Ye, Y, et al, Design, synthesis, and evaluation of near infrared fluorescent multimeric RGD peptides for targeting tumors, J. Med. Chem., 2006, pp. 2268-2275. vol. 49, No. 7.
Ye, Y, et al, Polyvalent carbocyanine molecular beacons for molecular recognitions, J Am Chem, 2004, pp. 7740-7741, vol. 126, No. 25.
Ye Y, et al, Novel Near-Infrared Fluorescent Integrin-Targeted DFO Analogue, Bioconjugate Chem, 2008, pp. 225-234, vol. 19.
Ye, Y, et al, Multivalent carbocyanine molecular probes: synthesis and applications, Bioconjug Chem, 2005, pp. 51-61, vol. 16, No. 1.
Zhang, Z, et al, Monomolecular multimodal fluorescence-radioisotope imaging, Bioconjug Chem, 2005, pp. 1232-1239, vol. 16, No. 5.

* cited by examiner

Primary Examiner — Cecilia J Tsang
Assistant Examiner — Satyanarayana Gudibande
(74) Attorney, Agent, or Firm — Polsinelli Shughart PC

(57) ABSTRACT

The present invention provides compounds that have motifs that target the compounds to cells that express integrins. In particular, the compounds have peptides with one or more RD motifs conjugated to an agent selected from an imaging agent and a targeting agent. The compounds may be used to detect, monitor and treat a variety of disorders mediated by integrins.

15 Claims, 26 Drawing Sheets
(13 of 26 Drawing Sheet(s) Filed in Color)

A B

C D

COMPOUNDS HAVING RD TARGETING MOTIFS

CROSS-REFERENCE TO RELATED APPLICATION

This application claims priority from PCT Application No. PCT/US2006/002056 that was filed on Jan. 20, 2006, which claims priority from Provisional Application No. 60/645,816 that was filed on Jan. 21, 2005, both of which are hereby incorporated by reference in their entirety.

GOVERNMENTAL RIGHTS

This invention was made with government support under the National Science Foundation Grant BES-01194889 and National Institutes of Health Grants R01CA109754 and R33CA100972. The government has certain rights in the invention.

FIELD OF THE INVENTION

The present invention provides compounds that have motifs that target the compounds to cells that express integrins. In particular, the compounds have peptides with one or more RD motifs conjugated to an agent selected from an imaging agent and a targeting agent. The compounds may be used to detect, monitor and treat a variety of disorders mediated by integrins.

BACKGROUND OF THE INVENTION

Angiogenesis, the formation of new blood vessels, is the cardinal feature of virtually all malignant tumors and because of its commonality, probing tumor-induced angiogenesis and associated proteins is a viable approach to detect and treat a wide range of cancers. Angiogenesis is stimulated by integrins, a large family of transmembrane proteins that mediate dynamic linkages between extracellular adhesion molecules and the intracellular actin skeleton. Integrins are composed of two different subunits, $\alpha$ and $\beta$, which are non-covalently bound into $\alpha\beta$ complexes. Particularly, the expression of $\alpha_v\beta_3$ integrin (ABI) in tumor cells undergoing angiogenesis and on the epithelium of tumor-induced neovasculature alters the interaction of cells with the extracellular matrix, thereby increasing tumorigenicity and invasiveness of cancers.

Numerous studies have shown that ABI and more than 7 other heterodimeric integrins recognize proteins and low molecular weight ligands containing RGD (arginine-glycine-aspartic acid) motifs in proteins and small peptides. Based on structural and bioactivity considerations, cyclic RGD peptide ligands are preferred as delivery vehicles of molecular probes for imaging and treating ABI-positive tumors and proliferating blood vessels. Until recently, most of the in vivo imaging studies were performed with radiopharmaceuticals because of the high sensitivity and clinical utility of nuclear imaging methods. Particularly, the use of small monoatomic radioisotopes does not generally interfere with the biodistribution and bioactivity of ligands. Therefore, once a high affinity ligand for a target receptor is identified, the radiolabeled analogue is typically used to monitor the activity, pharmacokinetics and pharmacodynamics of the drug or imaging agent. Despite these advantages, nuclear imaging is currently performed in specialized centers because of regulatory, production and handling issues associated with radiopharmaceuticals. Optical imaging is an alternative, but complementary method to interrogate molecular processes in vivo and in vitro.

Optical imaging for biomedical applications typically relies on activating chromophore systems with low energy radiation between 400 and 1500 nm wavelengths and monitoring the propagation of light in deep tissues with a charge-coupled device (CCD) camera or other point source detectors. Molecular optical imaging of diseases with molecular probes is attractive because of the flexibility to alter the detectable spectral properties of the beacons, especially in the fluorescence detection mode. The probes can be designed to target cellular and molecular processes at functional physiological concentrations. For deep tissue imaging, molecular probes that are photoactive in the near infrared (NIR) instead of visible wavelengths are preferred to minimize background tissue autofluorescence and light attenuation caused by absorption by intrinsic chromophores. In contrast to radioisotopes, the NIR antennas are usually large heteroatomic molecules that could impact the biodistribution and activity of conjugated bioactive ligands. However, previous studies have shown that conjugating small peptide carriers with NIR molecular probes successfully delivered the beacons to target proteins in vivo, and the nonspecific distribution of the conjugate in non-target tissues can be minimized by adjusting the net lipophilicity and ionic character of the conjugate.

A need, however, exists for additional compounds that can target and monitor integrin expression. In particular, a need exists for compounds that can target, monitor and/or treat a variety of integrin-mediated disorders.

SUMMARY OF THE INVENTION

The present invention provides compounds with motifs that target the compounds to cells that express integrins. One aspect of the invention encompasses a compound comprising at least one linear or cyclic peptide having a RD motif, the peptide conjugated to at least one agent selected from an imaging agent and a treatment agent. Another aspect of the invention encompasses a compound comprising at least one peptide having a RD motif and at least one cyclic peptide having a RGD motif, the peptide conjugated to at least one agent selected from an imaging agent and a treatment agent. Another aspect of the invention provides a method for selectively targeting at least one agent to a cell expressing a $\beta_3$ subunit of integrin, the method comprising conjugating a peptide having a RD motif to the agent, the peptide selectively targeting the agent to the cell.

Other aspects and features of the invention are described in more detail herein.

DESCRIPTION OF THE FIGURES

This application file contains at least one figure executed in color. Copies of this patent application publication with color figures will be provided by the Office upon request and payment of the necessary fee.

DETAILED DESCRIPTION OF THE PREFERRED EMBODIMENTS

Figure 1:
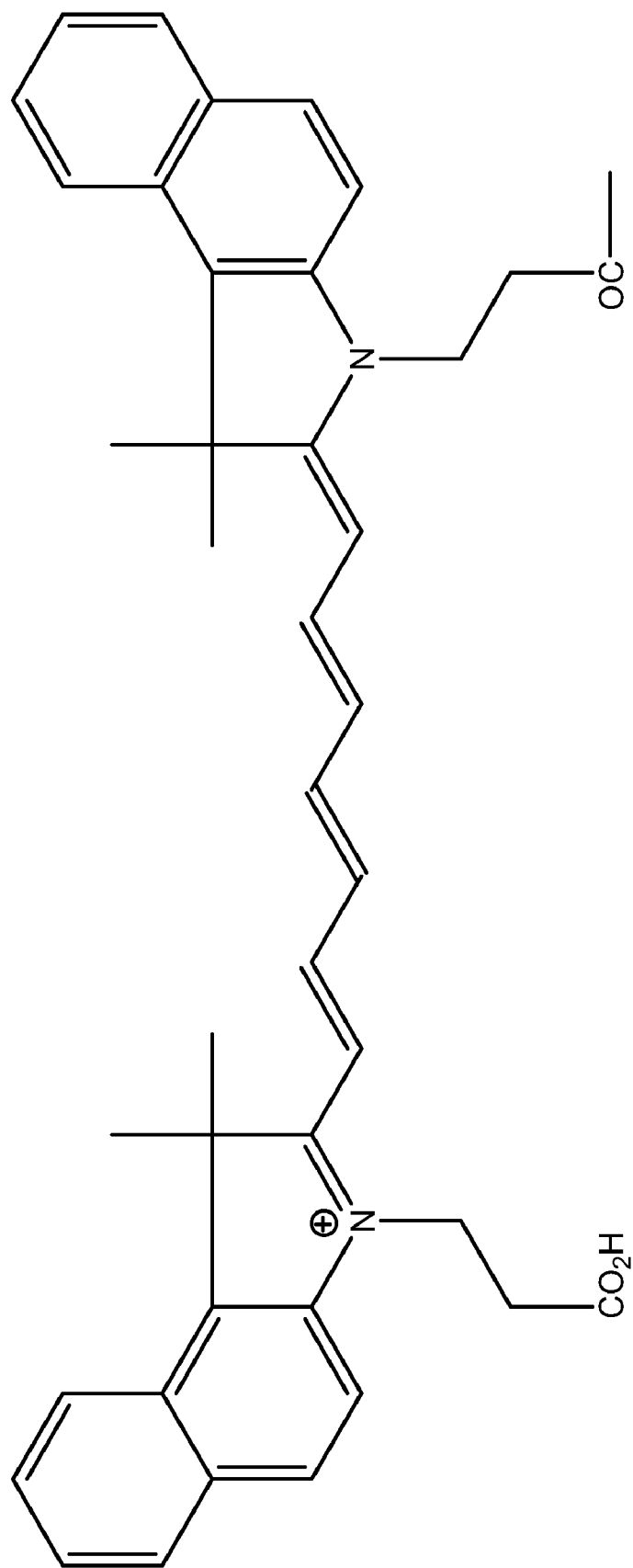
FIG. 1 presents the structure of cypate.

It has been discovered, as detailed in the examples, that a compound comprising a peptide having a RD motif, when conjugated to an agent such as an imaging agent or a treatment agent, targets the compound to a cell that expresses integrins. The present invention, accordingly, provides compounds that may be used to detect, monitor, and treat a variety of integrin-mediated biological processes, including the progression of disease states such as diabetes, cardiovascular disease, inflammation and cancer.

Compounds of the Invention

The compounds of the invention typically comprise at least one linear or cyclic peptide having a RD motif that is conjugated to at least one agent selected from an imaging agent and a treatment agent. The peptide may be conjugated to the agent directly by a covalent bond. Alternatively, the peptide may be conjugated to the agent by a linker. Suitable linkers are described below.

(1) Peptide Regions of the Compound

Generally, the peptide portion of the compound minimally has a size that includes at least one RD motif. In some embodiments, the peptide may be linear. In other embodiments, the peptide may be cyclic. Typically, the peptide will have from about 3 to about 50 amino acid residues. In another embodiment, the peptide will have from about 3 to about 30 amino acid residues. In a further embodiment, the peptide will have from about 3 to about 20 amino acid residues. In yet another embodiment, the peptide will have from about 3 to about 15 amino acid residues. In still another embodiment, the peptide will have from about 4 to about 12 amino acid residues. In a further embodiment, the peptide will have from about 4 to about 8 amino acid residues. In another embodiment, the peptide will have 4 amino acid residues. In an additional embodiment, the peptide will have 5 amino acid residues. In still another embodiment, the peptide will have 6 amino acid residues. In an additional embodiment, the peptide will have 7 amino acid residues. In yet another embodiment, the peptide will have 8 amino acid residues. In each of the aforementioned embodiments, the peptide, irrespective of its length, has at least one RD motif. It will be appreciated by the skilled artisan, that it is possible, and depending upon the embodiment, it may be desirable to have more than one RD motif within a peptide. For example, it is envisioned, depending upon the length of the peptide, that there may be from 2 to about 5 RD motifs in a given peptide.

The choice of amino acid residues, in addition to the RD motif, that will comprise the peptide will vary greatly depending upon the particular application for the compound. For example, it may be desirable in certain imaging or treatment applications that the compound be substantially hydrophilic. In other imaging or treatment applications, it may be desirable for the compound to be substantially hydrophobic. Generally, the amino acids may be selected from any amino acid residue including hydrophobic amino acids (e.g., L, A, P, V, M, F, W, and I), polar, uncharged amino acids (e.g., G, S, N, Q, T, Y, and C), acidic amino acids (e.g., D and E) and basic amino acids (e.g., K, H, and R). The amino acid residues may also be modified amino acid residues that are commonly known in the art. For embodiments in which a hydrophobic compound is desired, typically the amino acid residues comprising the peptide will be predominantly selected from hydrophobic amino acids. In embodiments in which a hydrophilic compound is desired, typically polar, typically the amino acid residues comprising the peptide will be predominantly polar, uncharged or polar, charged amino residues.

In an alternative embodiment, the compound may have more than one peptide having a RD motif with the size (i.e., number of amino acid residues) and amino acid composition detailed above. For applications involving more than one peptide, the individual peptides may form a single continuous chain with each individual peptide attached together either directly by a covalent bond or they may be separated by a linker. The single continuous chain of individual peptides may then be conjugated to the agent either directly via a covalent bond or by a linker. Alternatively, individual peptides may each be conjugated directly to the agent by either a covalent bond or by a linker. The number of individual peptides can and will vary. Typically, there may be from about 1 to about 15 peptides having a RD motif. In another embodiment, there may be from about 1 to about 12 peptides. In a further embodiment, there may be from about 1 to about 10 peptides. In yet another embodiment, there may be from about 1 to about 5 peptides. In a further embodiment, there is one peptide. In yet another embodiment, there are two peptides. In an additional embodiment, there are 3 peptides. In an additional embodiment, there are 4 peptides. In still another embodiment, there are 5 peptides.

In an alternative embodiment, the compound may include one or more cyclic peptides having at least one RGD motif. The cyclic peptide can and will vary in size. In one embodiment, the cyclic peptide is from about 4 amino acid residues to about 10 amino acid residues in size. In another embodiment, the cyclic peptide is from about 4 to about 6 amino acid residues in size. In yet another embodiment, the cyclic peptide is 5 amino acid residues in size. In a further embodiment, the cyclic peptide is 6 amino acid residues in size. The compound, as will be appreciated by a skilled artisan, may have more than one cyclic peptide. For example, the compound may have from 1 to about 10 cyclic peptides. More typically, the compound will have from about 1 to about 5 cyclic peptides. In one embodiment, the cyclic peptide may be conjugated to the compound by a covalent bound. Alternatively, the cyclic peptide may be conjugated to the compound by a linker.

(2) Imaging Agents and Treatment Agents

The compound of the invention may include at least one agent selected from an imaging agent and a treatment agent.

In one embodiment, the compound may comprise an imaging agent. In an alternative embodiment, the compound may comprise a treatment agent. In still another alternative embodiment, the compound may comprise an imaging agent and a treatment agent. Irrespective of the embodiment, the agent(s) may be either conjugated to the compound by a covalent bond or conjugated via a linker.

Several imaging agents are suitable for use to the extent that they provide the ability to detect or monitor the localization of the compound(s) of the present invention. In one embodiment, the imaging agent comprises an optical imaging agent. Optical imaging agents suitable for use in the invention can and will vary depending on the embodiment, but include fluorophores, organic fluorescent dyes, luminescent imaging agents, fluorescent lanthanide complexes, and fluorescent semiconductor nanocrystals. Examples of suitable visible (400-700 nm) fluorescent dyes include fluorescein, FITC, rhodamine, Texas Red, CyDyes (e.g., Cy3, Cy5, Cy5.5), Alexa Fluors (e.g., Alexa$^{488}$, Alexa$^{555}$, Alexa$^{594}$; Alexa$^{647}$) and DyDelight Dyes. Examples of suitable near infrared (NIR) (700-900 nm) fluorescent dyes include carbocyanine dyes, such as cypate and its derivatives. Luminescence imaging agents include luminescent lanthanide chelates and bioluminescence compounds (e.g., bacterial Lux, eukaryotic Luc or Ruc systems).

In an alternative embodiment, the imaging agent is a radiological imaging agent. A variety of radioisotopes that are capable of being detected, such as in a PET or SPECT diagnostic imaging procedure, are suitable for use in the present invention. Suitable examples of radiological imaging agents include Antimony-124, Antimony-125, Arsenic-74, Barium-103, Barium-140, Beryllium-7, Bismuth-206, Bismuth-207, Cadmium-109, Cadium-115, Calcium-45, Cerium-139, Cerium-141, Cerium-144, Cesium-137, Chromium-51, Gadolinium-153, Gold-195, Gold-199, Hafnium-175-181, Indium-111, Iridium-192, Iron-55, Iron-59, Krypton-85, Lead-210, Manganese-54, Mercury-197, Mercury-203, Molybdenum-99, Neodymium-147, Neptunium-237, Nickel-63, Niobium-95, Osmium-185, Palladium-103, Platinum-195, Praseodymium-143, Promethium-147, Protactinium-233, Radium-226, Rhenium-186, Rubidium-86, Ruthenium-103, Ruthenium-106, Scandium-44, Scandium-46, Selenium-75, Silver-110, Silver-111, Sodium-22, Strontium-85, Strontium-89, Strontium-90, Sulfur-35, Tantalum-182, Technetium-99, Tellurium-125, Tellurium-132, Thallium-204, Thorium-228, Thorium-232, Thallium-170, Tin-113, Titanium-44, Tungsten-185, Vanadium-48, Vanadium-49, Ytterbium-169, Yttrium-88, Yttrium-90, Yttrium-91, Zinc-65, and Zirconium. In a further alternative embodiment, the radiological imaging agent is selected from the group consisting of Technecium-99, Indium-111, Strontium-90, Iodine-125, Thallium-201, fluorine-18, carbon-11, carbon-13, nitrogen-13, Oxygen-15, Copper-64, Lutetium-177, Yttrium-90, and Iodine-131

A variety of other imaging agents are suitable for use in the invention. For example, other imaging agents include, Gadolinium, metalloporphyrins, ferric chloride, ferric ammonium citrate, and ferrioxamine methanesulfonate for magnetic resonance imaging.

The compound of the invention optionally includes one or more treatment agents, such as a drug or hormone. As will be appreciated by the skilled artisan, the choice of a particular treatment agent can and will vary depending upon the indication to be treated and its stage of progression. Because the compounds of the invention are selectively targeted to cells that express integrins, as detailed in the examples, the treatment agents are generally directed toward treatment of an intregrin-mediated disorder such as diabetes, inflammation, cardiovascular disease, and cancer. For example, when the indication is diabetes, the treatment agent may be sulfonylureas, biguanides, thiazolidinediones, meglitinides, D-phenylalinine derivatives, amylin synthetic derivatives, and incretin mimetics, In a further embodiment, when the indication is inflammation, the treatment agent may be an NSAID such as aniline derivatives (acetomenaphin), indole-3-acetic acid derivatives (indomethacin), specific Cox-2 inhibitors (Celebrex), and aspirin. By way of further example, when the indication is cardiovascular disease, the treatment agent may include sodium-channel blockers (e.g., quinidine), beta-blockers (e.g., propranolol), calcium-channel blockers (e.g., diltiazen), diuretics (e.g., hydrochlorothiazide), ACE inhibitors (e.g., captopril), and thrombolytic agents (e.g., tissue plasminogen activator and streptokinase). In an additional embodiment when the indication is cancer, the treatment agent may include DNA synthesis inhibitors (e.g., daunorubicin, and adriamycin), mitotic inhibitors (e.g., the taxanes, paclitaxel, and docetaxel), the vinca alkaloids (e.g., vinblastine, vincristine, and vinorelbine), antimetabolites (e.g., 5-fluorouracil, capecitabine, 6-mercaptopurine, methotrexate, gemcitabine, cytarabine (ara-C), fludarabine, pemetrexed, cytosine arabinoside, methotrexate, and aminopterin), alkylating agents (e.g., busulfan, cisplatin, carboplatin, chlorambucil, cyclophosphamide, ifosfamide, dacarbazine (DTIC), mechlorethamine (nitrogen mustard), melphalan, and temozolomide), nitrosoureas (e.g., carmustine (BCNU) and lomustine (CCNU) anthracyclines (e.g., daunorubicin, doxorubicin (Adriamycin), epirubicin, idarubicin, and mitoxantrone), topoisomerase inhibitors (e.g., topotecan, irinotecan, etoposide (VP-16), and teniposide), cytotoxins (e.g., paclitaxel, vinblastine, and macromycin,), anti-cytoskeletals (e.g., taxol and cholchicine) and angiogenesis inhibitors (e.g., VEGF inhibitors, anti-VEGF Abs). Other suitable treatment agents may include hormones (e.g., steroids), antibodies, antibody fragments, peptides, glycopeptides, peptidomimetic, drug mimic, metal chelating agents, radioactive agents, echogenic agents, various drugs (in addition to the ones specifically delineated), antisense molecules, and small inhibitory RNAs.

(3) Linkers

In certain embodiments, the imaging agent and/or treatment agent is conjugated to the linear peptide via one or more linkers. In other embodiments having more than one linear peptide or one or more cyclic peptides, the individual peptides may optionally be conjugated via one or more linkers.

A variety of linkers are suitable in the present invention, but typically the linker will impart a degree of flexibility to the compound of the invention. Generally speaking, the chain of atoms defining the linker can and will vary depending upon the embodiment. In certain embodiment, the linker will comprise one or more amino acids. Exemplary amino acid utilized in the linker include G, S and A.

In a further embodiment, the linker will comprise hydrocarbyl or substituted hydrocarbyl groups. In a typical alternative of this embodiment, the linker is from about 1 to about 50 atoms in length. Alternatively, the linker is from about 2 to about 30 atoms in length. In an exemplary embodiment, the linker is from about 4 to about 20 atoms in length. The linker may comprise a variety of heteroatoms that may be saturated or unsaturated, substituted or unsubstituted, linear or cyclic, or straight or branched. The chain of atoms defining the linker will typically be selected from the group consisting of carbon, oxygen, nitrogen, sulfur, selenium, silicon and phosphorous.

In an alternative embodiment, the chain of atoms is selected from the group consisting of carbon, oxygen, nitrogen, sulfur and selenium. In an exemplary embodiment, the linker will comprise substantially carbon and oxygen atoms. In addition, the chain of atoms defining the linker may be substituted or unsubstituted with atoms other than hydrogen, including, but not limited to, hydroxy, keto (=O), or acyl, such as acetyl. Thus, the chain may optionally include one or more ether, thioether, selenoether, amide, or amine linkages between hydrocarbyl or substituted hydrocarbyl regions. Exemplary linkers include ethylene glycol and aminohexanoic acid.

(4) Exemplary Compounds of the Invention

In one exemplary embodiment, the compound will have the characteristics detailed above and will be defined by formula (I):

wherein:
R$^1$ and R$^2$ are independently selected from the group consisting of an imaging agent, a treatment agent, hydrogen, hydroxyl, hydrocarbyl, and substituted hydrocarbyl, provided at least one of R$^1$ or R$^2$ is an imaging agent or a treatment agent;
X$^1$ and X$^2$ are independently selected from any amino acid residue;
X$^1_m$—R-D-X$^2_p$ together form a linear or cyclic peptide;
m is an integer from 1 to about 10;
n is an integer from 1 to about 10;
p is an integer from 1 to about 10; and
a dash (-) represent a covalent bond.

In an alternative embodiment, the compound will have formula (I) wherein:
n is from 1 to 5;
m is from 1 to 3;
p is from 1 to 3; and
X$^1$ and X$^2$ are selected from the group consisting of G, S, N, Q, D, E, K,
R, T, Y, C, and H.

In each embodiment for compounds having formula (I), the compound may optionally comprise a linker, L$^1$, that conjugates R$^1$ to X$^1$. The compound may additionally comprise a linker, L$^2$, that conjugates R$^2$ to X$^2$. In addition, the compound may additionally comprise a linker, L$^3$, that conjugates R$^1$ to X$^2$. The compound may additionally comprise a linker, L$^4$, that conjugates R$^2$ to X$^1$. The compound may additionally comprise a linker, L$^5$, that conjugates X$^1$ to X$^2$. Furthermore, the compound may additionally comprise a linker, L$^6$, that conjugates R$^1$ to R$^2$.

Alternatively, for each embodiment for compounds having formula (I), the compound may optionally comprise at least one cyclic peptide having a RGD motif. Generally, the cyclic peptide has from about 4 amino acid residues to about 10 amino acid residues. In one embodiment, the cyclic peptide has 5 amino acid residues. In this embodiment, 3 of the amino acid residues will be the RGD motif and the other two amino acid residues may be selected from any amino acid residue detailed above. In an alternative embodiment, the cyclic peptide has 6 amino acid residues. In this embodiment, 3 of the amino acid residues will be the RGD motif and the other three may be selected from any amino acid residue detailed above.

In a further exemplary embodiment, the compound will have the characteristics detailed above and will be defined by formula (II):

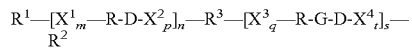

wherein:
  $R^1$ and $R^2$ are independently selected from the group consisting of an imaging agent, a treatment agent, hydrogen, hydroxyl, hydrocarbyl, and substituted hydrocarbyl, provided at least one of $R^1$ or $R^2$ is an imaging agent or a treatment agent;
  $R^3$ is a covalent bond or a linker;
  $X^1$, $X^2$, $X^3$ and $X^4$ are independently selected from any amino acid residue;
  $X^1_m$—R-D-$X^2_p$ together form a linear or cyclic peptide;
  $X^3_q$—R-G-D-$X^4_t$ together form a cyclic peptide;
  m is an integer from 1 to about 10;
  n is an integer from 1 to about 10;
  p is an integer from 1 to about 10;
  q is an integer from about 1 to 5;
  s is an integer from about 1 to 10;
  t is an integer from about 1 to 5; and
  a dash (-) represent a covalent bond.

In an alternative embodiment, the compound will have formula (II) wherein:
  n is from 1 to 3;
  m is from 1 to 3;
  p is from 1 to 3;
  q is 2 or 3;
  s is from 1 to 3;
  t is 2 or 3;
  $X^1$ and $X^2$ are selected from the group consisting of G, S, N, Q, D, E, K, R, T, Y, C, and H; and
  $X^3$ and $X^4$ are selected from any amino acid residue.

In each embodiment for compounds having formula (II), the compound may optionally comprise a linker, $L^1$, that conjugates $R^1$ to $X^1$. In addition, the compound may additionally comprise a linker, $L^2$, that conjugates $R^2$ to $X^2$.

Other exemplary compounds of the invention are illustrated in the Examples.

In addition, the compound(s) of the present invention can exist in tautomeric, geometric or stereoisomeric forms. The present invention contemplates all such compounds, including cis- and trans-geometric isomers, E- and Z-geometric isomers, R- and S-enantiomers, diastereomers, d-isomers, l-isomers, the racemic mixtures thereof and other mixtures thereof. Pharmaceutically acceptable salts of such tautomeric, geometric or stereoisomeric forms are also included within the invention. The terms "cis" and "trans", as used herein, denote a form of geometric isomerism in which two carbon atoms connected by a double bond will each have a hydrogen atom on the same side of the double bond ("cis") or on opposite sides of the double bond ("trans"). Some of the compounds described contain alkenyl groups, and are meant to include both cis and trans or "E" and "Z" geometric forms. Furthermore, some of the compounds described contain one or more stereocenters and are meant to include R, S, and mixtures of R and S forms for each stereocenter present.

In a further embodiment, the compound(s) of the present invention may be in the form of free bases or pharmaceutically acceptable acid addition salts thereof. The term "pharmaceutically-acceptable salts" are salts commonly used to form alkali metal salts and to form addition salts of free acids or free bases. The nature of the salt may vary, provided that it is pharmaceutically acceptable. Suitable pharmaceutically acceptable acid addition salts of compounds for use in the present methods may be prepared from an inorganic acid or from an organic acid. Examples of such inorganic acids are hydrochloric, hydrobromic, hydroiodic, nitric, carbonic, sulfuric and phosphoric acid. Appropriate organic acids may be selected from aliphatic, cycloaliphatic, aromatic, araliphatic, heterocyclic, carboxylic and sulfonic classes of organic acids, examples of which are formic, acetic, propionic, succinic, glycolic, gluconic, lactic, malic, tartaric, citric, ascorbic, glucuronic, maleic, fumaric, pyruvic, aspartic, glutamic, benzoic, anthranilic, mesylic, 4-hydroxybenzoic, phenylacetic, mandelic, embonic (pamoic), methanesulfonic, ethanesulfonic, benzenesulfonic, pantothenic, 2-hydroxyethanesulfonic, toluenesulfonic, sulfanilic, cyclohexylaminosulfonic, stearic, algenic, hydroxybutyric, salicylic, galactaric and galacturonic acid. Suitable pharmaceutically-acceptable base addition salts of compounds of use in the present methods include metallic salts made from aluminum, calcium, lithium, magnesium, potassium, sodium and zinc or organic salts made from N,N'-dibenzylethylenediamine, chloroprocaine, choline, diethanolamine, ethylenediamine, meglumine-(N-methylglucamine) and procaine.

As will be appreciated by a skilled artisan, the compound(s) of the present invention can be administered by a number of different means that will deliver an effective dose for either detection or treatment purposes. Such compositions can be administered orally, parenterally, by inhalation spray, rectally, intradermally, transdermally, or topically in dosage unit formulations containing conventional nontoxic pharmaceutically acceptable carriers, adjuvants, and vehicles as desired. Topical administration may also involve the use of transdermal administration such as transdermal patches or iontophoresis devices. The term parenteral as used herein includes subcutaneous, intravenous, intramuscular, or intrasternal injection, or infusion techniques. Formulation of drugs is discussed in, for example, Hoover, John E., Remington's Pharmaceutical Sciences, Mack Publishing Co., Easton, Pa. (1975), and Liberman, H. A. and Lachman, L., Eds., Pharmaceutical Dosage Forms, Marcel Decker, New York, N.Y. (1980).

Injectable preparations, for example, sterile injectable aqueous or oleaginous suspensions, can be formulated according to the known art using suitable dispersing or wetting agents and suspending agents. The sterile injectable preparation may also be a sterile injectable solution or suspension in a nontoxic parenterally acceptable diluent or solvent. Among the acceptable vehicles and solvents that may be employed are water, Ringer's solution, and isotonic sodium chloride solution. In addition, sterile, fixed oils are conventionally employed as a solvent or suspending medium. For this purpose, any bland fixed oil may be employed, including synthetic mono- or diglycerides. In addition, fatty acids such as oleic acid are useful in the preparation of injectables. Dimethyl acetamide, surfactants including ionic and non-ionic detergents, and polyethylene glycols can be used. Mixtures of solvents and wetting agents such as those discussed above are also useful.

Solid dosage forms for oral administration may include capsules, tablets, pills, powders, and granules. In such solid dosage forms, the compound is ordinarily combined with one or more adjuvants appropriate to the indicated route of administration. If administered per os, the compound can be admixed with lactose, sucrose, starch powder, cellulose esters of alkanoic acids, cellulose alkyl esters, talc, stearic acid, magnesium stearate, magnesium oxide, sodium and calcium salts of phosphoric and sulfuric acids, gelatin, acacia gum, sodium alginate, polyvinylpyrrolidone, and/or polyvinyl alcohol, and then tableted or encapsulated for convenient administration. Such capsules or tablets can contain a controlled-release formulation as can be provided in a dispersion of active compound in hydroxypropylmethyl cellulose. In the case of capsules, tablets, and pills, the dosage forms can also comprise buffering agents such as sodium citrate, or magnesium or calcium carbonate or bicarbonate. Tablets and pills can additionally be prepared with enteric coatings.

For therapeutic purposes, formulations for parenteral administration can be in the form of aqueous or non-aqueous isotonic sterile injection solutions or suspensions. These solutions and suspensions can be prepared from sterile powders or granules having one or more of the carriers or diluents mentioned for use in the formulations for oral administration. The compounds can be dissolved in water, polyethylene glycol, propylene glycol, ethanol, corn oil, cottonseed oil, peanut oil, sesame oil, benzyl alcohol, sodium chloride, and/or various buffers. Other adjuvants and modes of administration are well and widely known in the pharmaceutical art.

Liquid dosage forms for oral administration can include pharmaceutically acceptable emulsions, solutions, suspensions, syrups, and elixirs containing inert diluents commonly used in the art, such as water. Such compositions can also comprise adjuvants, such as wetting agents, emulsifying and suspending agents, and sweetening, flavoring, and perfuming agents.

The compound(s) of the present invention may be employed for the detecting, monitoring and/or treatment or prevention of a variety of integrin-mediated disorders, as identified above, in a number of subjects. Besides being useful for human detection, monitoring, treatment and/or prevention, the compound(s) is also useful for veterinary treatment of companion animals, exotic animals and farm animals, including mammals, rodents, avians, and the like. More preferred animals include horses, dogs, cats, sheep, and pigs.

DEFINITIONS

The term "detect" as used herein refers to diagnostic procedures and methods to image the compounds of the invention. These procedures include, but are not limited to, optical tomography, fluorescence endoscopy, imaging detection or measurement of or by fluorescence and imaging absorption, light scattering, acoustic, sonographic, magnetic resonance, or radiation means.

The term "hydrocarbyl" as used herein describe organic compounds or radicals consisting exclusively of the elements carbon and hydrogen. These moieties include alkyl, alkenyl, alkynyl, and aryl moieties. These moieties also include alkyl, alkenyl, alkynyl, and aryl moieties substituted with other aliphatic or cyclic hydrocarbon groups, such as alkaryl, alkenaryl and alkynaryl. Unless otherwise indicated, these moieties preferably comprise 1 to 20 carbon atoms.

The term "localized therapy" is a procedure for administering a compound of the invention directly into pathological tissue. Treatment in localized therapy may be accomplished by photo-, chemical-, or biological activation of the compound of the invention. Photoactivation may be conducted with light within a specific wavelength range. Chemical activation may be induced cytotoxicity. Biological activation may be initiated by physiological and molecular processes, including enzymatic activation of the compound.

The term "monitoring" as used herein refers to the continued or intermittent detection and may be combined with treatment for purposes including, but not limited to, ascertaining the progress or mechanism of pathology and efficacy of a particular treatment regime.

The term "substituted hydrocarbyl" moieties described herein are hydrocarbyl moieties which are substituted with at least one atom other than carbon, including moieties in which a carbon chain atom is substituted with a hetero atom such as nitrogen, oxygen, silicon, phosphorous, boron, sulfur, or a halogen atom. These substituents include halogen, carbocycle, aryl, heterocyclo, alkoxy, alkenoxy, alkynoxy, aryloxy, hydroxy, protected hydroxy, keto, acyl, acyloxy, nitro, amino, amido, nitro, cyano, thiol, ketals, acetals, esters and ethers.

The term "treat" or "treatment" includes partial or total inhibition of the progression of a particular disorder. For example when the disorder is cancer, treatment include partial or total inhibition of neoplasia growth, spreading or metastasis, as well as partial or total destruction of the neoplasia cells. Treatment also includes prevention of a neoplasia or related disorder. By way of further example when the disorder is inflammation, the term "treat" also includes partial or total inhibition of inflammation or an inflammation related disorder. Treatment also includes prevention of an inflammation or inflammation related disorder.

As various changes could be made in the above compounds, products and methods without departing from the scope of the invention, it is intended that all matter contained in the above description and in the examples given below, shall be interpreted as illustrative and not in a limiting sense.

EXAMPLES

The following examples illustrate various embodiments of the invention.

Example 1

Synergistic Effects of Light-Emitting Probes and Peptides for Targeting and Monitoring Integrin Expression Angiogenesis, the formation of new blood vessels, is the cardinal feature of virtually all malignant tumors. Because of this commonality, probing tumor-induced angiogenesis and associated proteins is a viable approach to detect and treat wide range of cancers. Angiogenesis is stimulated by integrins, large family of transmembrane proteins that mediate dynamic linkages between extracellular adhesion molecules and the intracellular actin skeleton. Integrins are composed of two different subunits, $\alpha$ and $\beta$, which are noncovalently bound into $\alpha\beta$ complexes. Particularly, the expression of $\alpha_v\beta_3$ integrin (ABI) in tumor cells undergoing angiogenesis and on the epithelium of tumor-induced neovasculature alters the interaction of cells with the extracellular matrix, thereby increasing tumorigenicity and invasiveness of cancers. Numerous studies have shown that ABI and more than seven other heterodimeric integrins recognize proteins and low molecular weight ligands containing RGD (arginine-glycine-aspartic acid) motifs in proteins and small peptides. Based on structural and bioactivity considerations, cyclic RGD peptide ligands are preferentially used as delivery vehicles for molecular probes for imaging and treating ABI-positive tumors and proliferating blood vessels. Until recently, most of the in vivo imaging studies were performed with radiopharmaceuticals because of the high sensitivity and clinical utility of nuclear imaging methods. Particularly, the use of small mono-atomic radioisotopes does not generally interfere with the biodistribution and bioactivity of ligands. Despite these advantages, nuclear imaging is currently only performed in specialized centers because of regulatory, production, and handling issues associated with radiopharmaceuticals. Optical imaging is an alternative but complementary method to interrogate molecular processes in vivo and in vitro.

Optical imaging for biomedical applications typically relies on activating chromophore systems with low energy radiation between 400- and 1,500-nm wavelengths and monitoring the propagation of light in deep tissues with a charge-coupled device camera or other point source detectors. Molecular optical imaging of diseases with molecular probes is attractive because of the flexibility of altering the detectable spectral properties of the probes, especially in the fluorescence detection mode. The probes can be designed to target cellular and molecular processes at functional physiological concentrations. For deep-tissue imaging, molecular probes that are photoactive in the near-infrared (NIR) instead of visible wavelengths are preferred to minimize background tissue autofluorescence and light attenuation caused by absorption by intrinsic chromophores. In contrast to radioisotopes, the NIR antennas are usually large heteroatomic molecules that could impact the biodistribution and activity of conjugated bioactive ligands. However, studies have shown that conjugating small peptide carriers with NIR molecular probes successfully delivered the probes to target proteins in vivo, and the nonspecific distribution of the conjugate in nontarget tissues can be minimized by adjusting its net lipophilicity and ionic character (Achilefu (2004) Technol. Cancer Res. Treat. 3:393-40920).

This study reports a previously undescribed integrin-specific ligand prepared from two motifs that lack ABI recognizable motifs. One motif is a NIR carbocyanine fluorescent probe (cypate) that is currently used to develop bioactive optical contrast agents (Achilefu et al. (2000) Invest. Radiol. 36:479-485), and the other is a linear hexapeptide (GRDSPK, abbreviated GRD) [SEQ ID NO:8] that lacks the RGD sequence. Intuitively, deletion of glycine in the linear RGD heptapeptide would be expected to diminish or eradicate the binding of the resulting GRD peptide to ABI because of alteration in the interatomic distances between the arginine and aspartic acid binding groups. Expectedly, the GRD peptide and its radiometal chelate conjugate (for scintigraphy) were not retained in the ABI-positive A549 tumor. In contrast, the cypate-GRD conjugate was internalized in A549 cells in vitro and its uptake was inhibited by high affinity ABI-binding ligands. Particularly, antibody-blocking studies demonstrate the effective inhibition of cypate-GRD uptake by anti-$\beta_3$ monoclonal antibody (mAb) and to a lesser extent by anti-$\alpha_v$ mAb. This finding suggests that the $\beta_3$ subunit in ABI initiates the cellular uptake of cypate-GRD by A549 cells. In vivo, the molecular probe preferentially accumulated in A549 tumors in nude mice. Coadministration of the probe with high-affinity ABI-binding ligand successfully blocked the probe's uptake in the tumor, thereby demonstrating the specificity of the observed tumor retention of cypate-GRD. These results demonstrate the synergistic effects of the tandem carbocyanine molecular probe and the peptide motif in targeting integrin-positive tumors. The findings suggest that the structural framework of the probe can serve as an optical scaffold to develop novel bioactive molecules for imaging diseases and potentially monitoring the efficacy of new drugs.

Molecular Design and Synthesis

All reagents and solvents were obtained from commercial sources and used without further purification. Amino acids were purchased from Novabiochem (San Diego, Calif.). The ABI-avid peptide, cyclo[RGDfV] [SEQ ID NO:1], which binds to ABI, was purchased from Peptides International Inc., (Louisville, Ky.) and used for blocking studies. Octreotate, an octapeptide that binds somatostatin receptors but not ABI, was prepared as previously described (Achilefu et al. (2002) J. Med. Chem. 45:2003-2015). Purification and analysis of the new peptides were performed on an HPLC system equipped with a tunable UV-visible detector. Analytical (flow rate=0.5 mL/min) and semipreparative (flow rate=10 mL/min) reverse phase-HPLC were performed on C-18 columns and detected at 214 and 254 nm. The gradient elution protocol ranged from a mixture of 95% solvent A and 5% solvent B to 30% A and 70% B in 30 min, where solvent A is 0.1% aqueous TFA and solvent B is acetonitrile containing 0.1% of a solution of 0.1% aqueous TFA. All percentages are expressed in v/v. Electrospray ionization mass spectrometry (ES-MS) analysis was performed on a triple quadruple mass spectrometer. The electrospray interface was operated in positive ion mode with a spray voltage of 3.0 kV and a capillary temperature of 300° C. Samples in 70% solvent A and 30% solvent B were introduced into the spectrometer by direct injection. The HPLC purities of all compounds used for the in vivo and in vitro studies were generally >95%.

Synthesis of Cypate (NIR Dyes)

A general method for the synthesis of cypate (FIG. 1) (>99%) is described in Ye et al. (2004) (J. Am. Chem. Soc. 126:7740-7741) and is incorporated by reference herein.

To synthesize cypate, a mixture of 1,1,2-trimethyl-[1H]-benz[e]indole (40.0 g, 19.11 mmol) and 3-bromopropanoic acid (40.0 g, 26.15 mmol) in 1,2-dichlorobenzene (200 mL) was heated at 110° C. for 18 h. After the resulting mixture was cooled to room temperature, the precipitate was collected by filtration, followed by trituration in dichloromethane (DCM) to remove the un-reacted material, and then dried under vacuum to afford 1,1,2-trimethyl[1H]-benz[e]indole-3-propanoic acid. A solution of acetic anhydride (1.20 g, 11.75 mmol) in DCM (5 mL) was added dropwise to a cooled suspension of glutaconaldehyde dianil monohydrochloride (2.84 g, 9.97 mmol) and diisopropylethylamine (DIEA, 2.60 g, 20.11 mmol) in DCM (20 mL). The resulting clear solution was stirred for 1 h and added dropwise to a refluxing solution of 1,1,2-trimethyl[1H]-benz[e]indole-3-propanoic acid (8.2 g, 22.64 mmol) and sodium acetate (3.2 g, 39.01 mmol) in acetonitrile/water (95/5 mL). The mixture was refluxed for 16 h, cooled, filtered, and washed with acetonitrile, 5% HCl solution and ethyl ether. About 6 g (85%) of cypate was obtained. It was further purified by recrystallization from 30% acetonitrile in water. Mass calculated: 625; observed (ESI-MS): 625.34 [M]$^+$.

Cypate-3 is useful to accommodate the optimal spectral properties of a fluorescence microscope in the visible wavelengths. The probe was prepared by a similar procedure described above, starting from malconaldehyde dianilide monohydrochloride (2.0 g) instead of glutaconaldehyde dianil mono hydrochloride to afford cypate-3 (3.1 g, 60%). Mass calculated 599; observed (ESI-MS): 599.32 [M]$^+$.

Synthesis of Linear Peptides and Conjugation with Fluorescent Probes

The peptides were prepared with ACT APEX 396 peptide synthesizer by standard fluorenylmethyl (Fmoc) protocol (Solid Phase Peptide Synthesis: A Practical Approach, Oxford University Press, 1989) as previously described (Achilefu et al. (2000) Invest. Radiol. 35:479-485; Achilefu et al. (2002) J. Med. Chem. 45:2003-2015, which are incorporated by reference herein). Briefly, a Wang resin pre-loaded with Fmoc-Lys-OH on a 25-µmole scale was placed in a reaction vessel. Subsequent Fmoc-protected amino acids (75 µmol) were sequentially coupled to the resin-bound amino acid from the carboxyl to amino terminus. Fmoc removal was accomplished with 20% piperidine in dimethyl formamide (DMF). The coupling reagents N-hydroxybenzotriazole (HOBt, 75 µmol) and 2-(1H-benzotriazol-1-yl)-1,1,3,3-tetramethyluronium hexafluoro phosphate (HBTU, 75 µmol) were used for the peptide assembly in the presence of DIEA (150 µmol). Peptide cleavage from the resin and concomitant removal of the amino acid side-chain protecting groups were accomplished by adding a cleavage mixture (1 mL) of TFA (85%), distilled water (5%), phenol (5%), and thioanisole (5%) to the resin and gently mixing the content for 3 h. The crude peptide was precipitated in cold t-butyl methyl ether (MTBE) and lyophilized in acetonitrile/water (2:3) mixture. The resulting powder was purified by HPLC and analyzed by ES-MS.

Conjugation of the dyes with the peptides was performed on solid supports. After peptide assembly (25 μmol), the N-terminal Fmoc group was removed with 20% piperidine in DMF. Cypate or cypate-3 (75 μmol) was pre-activated with diisopropyl carbodiimide (DIC, 125 μmol) in DMF (2 mL) for 20 min and added to the resin-bound peptide. The mixture was swirled for 12 h, filtered, washed with DMF and methanol. The resulting green resin was treated as described above for peptide cleavage and workup. The following compounds were prepared by this general method:

GRDSPK (also referred to as GRD) [SEQ ID NO:8]: 19.92 mg; 19.9 μmol; 79.6% isolated yield; mass (calculated): 658.35; observed (ES-MS): 659.36 [MH]$^+$.
Cypate-GRDSPK (also referred to as Cyp-GRD) [SEQ ID NO:6]: 8.1 mg; 6.40 μmol; 25.6% isolated yield; mass (calculated): 1265.3; observed (ES-MS): 1265.3 [M]$^+$.
Cypate-GRGDPK [SEQ ID NO:9]: 6.4 mg; 4.84 μmol; 19.4% isolated yield; mass (calculated): 1322.37; observed (ES-MS): 1322.55 [M]$^+$. Cypate-GRGDSPK (also called Cyp-RGD) [SEQ ID NO:5] was used in some experiments.
Cypate-3-GRDSPK (also referred to as Cyp-3-GRD) [SEQ ID NO:10]: 5.2 mg; 4.19 μmol; 16.8% isolated yield; mass (calculated): 1239.4; observed (ES-MS): 1240.4 [MH]$^+$.

Synthesis of Cyclic Peptide and Conjugation

The cyclic Cypate-conjugated peptides Cypate-cyclo[RGDfVL$^{(Cypate)}$] [SEQ ID NO:11] and Cypate-cyclo[RGD-fVK$^{(Cypate)}$] [SEQ ID NO:7] (also referred to as Cyp-cyclo-RGD) were prepared in three steps: (a) solid phase peptide synthesis, (b) intramolecular lactamization in solution, and (c) dye conjugation.

H-Lys(Dde)-Arg(Pbf)-Gly-Asp(Obu$^r$)-Dphe-Val-OH [SEQ ID NO:12]: The linear peptide was assembled on Fmoc-Val-2-chlorotrityl resin (0.6 g, substitution 0.33 mmol/g) by conventional Fmoc chemistry and cleaved with TFA/DCM mixture (1:99), as described above. The filtrate was added to a solution of pyridine (20 mL) and methanol (80 mL), concentrated, washed with water, and dried to afford the desired compound (142.0 mg; 60%). ES-MS: [MH]$^+$ 1193.51

Cyclo[Arg(Pbf)-Gly-Asp(Obu$^r$)-Dphe-Val-Lys] [SEQ ID NO:13]: To a solution of the above linear peptide (130.0 mg, 0.11 mmol), HOBt (23.0 mg, 0.17 mmol), and PyBOP (88.4 mg, 0.17 mmol) in DMF (15 mL) was added DCM (500 mL), followed by DIEA (44.0 mg, 0.34 mmol). The mixture was stirred at room temperature for 24 h, concentrated under vacuum, and re-dissolved in DCM. The solution was washed with water, 5% HCl, and 5% K$_2$CO$_3$, dried, and concentrated to afford a crude cyclic product, cyclo[Arg(Pbf)-Gly-Asp(Obu$^r$)-Dphe-Val-Lys(Dde)] [SEQ ID NO: 14](ES-MS: [MH]$^+$ 1175.47). The crude product was stirred in a 30 mL solution of 5% hydrazine in acetonitrile for 30 min, concentrated, and purified by HPLC to afford 30.0 mg (23%) of the cyclic compound containing free ε-amino lysine group. This product was dissolved in DCM and washed with 5% sodium carbonate solution for subsequent conjugation with cypate. Mass (calculated): 1011.2; observed (ES-MS): 1011.3[M]$^+$, 506.1 [M+2H]$^{2+}$.

Conjugation with cypate: A mixture of cypate (42.3 mg, 0.06 mmol), 1-ethyl-3-(3'-dimethylaminopropyl)carbodiimide (EDCI; 11.5 mg, 0.06 mmol), HOBt (16.0 mg, 0.12 mmol), and the above cyclic peptide (25.0 mg, 0.02 mmol) in DMF (3.0 mL) was stirred for 24 h, concentrated, re-dissolved in DCM, washed with 5% aqueous HCl solution and water, and concentrated to give the protected peptide (ES-MS: 1618.30 [MH]$^+$). The crude product was stirred in 15 mL of TFA/water (95:5) at room temperature for 3 h to remove the side-chain protecting groups, concentrated, and precipitated in cooled MTBE solution. The precipitate was purified by HPLC to afford 3.7 mg (12%) of the desired compound. ES-MS: 1309.47 [MH]$^+$; 655.29 [M+2H]$^{2+}$.

Synthesis of DOTA-Peptide Conjugate

DOTA-Gly-Arg-Asp-Ser-Pro-Lys-OH [SEQ ID NO:15] (DOTA-GRD) was prepared as described above at a 25-μmol scale. After removal of the N-terminal Fmoc, orthogonally protected tri-tert-butyl N',N'',N''', N''''-dodecyltetraacetic acid (DOTA; 75 μmol, Macrocylics, Inc. Dallas, Tex.) was coupled automatically with the free amino group in the presence of HOBt/HBTU/DIEA in DMF. TFA cleavage, workup, and purification were performed as described above to afford DOTA-GRD as a colorless powder (9.2 mg; 8.8 μmol; 35%). Mass (calculated): 1044.8; observed (ES-MS): 1045.69 [MH]$^+$.

Absorption and Emission Properties

The spectral properties of cypate and the cypate-peptide conjugates were determined in 20% aqueous DMSO, which solubilizes all the compounds. This solvent mixture has also been shown to be biocompatible for both in vitro and in vivo applications (Achilefu et al. (2000) Invest. Radiol. loc. cit. and Bugaj et al. (2001) J. Biomed. Optics 6:122-133, the latter incorporated by reference herein). Absorbance measurements were performed with a Beckman Coulter DU 640 spectrophotometer. The fluorescence spectra were recorded on Fluorolog-3 fluorometer (HORIBA Jobin Yvon Inc., Edison, N.J.). To prepare the stock solutions, a high precision analytical balance was used to weigh >2 mg of each compound, which was dissolved in DMSO. The DMSO solutions were then diluted with water to obtain a final solution of 20% aqueous DMSO. An aliquot (known volume) of the solution was transferred to a cuvette with 1 μL precision micropipettes and diluted with 20% aqueous DMSO solvent mixture to give a working solution that absorbs at <1.0 absorbance unit. Aliquots of the working solution were diluted with 20% aqueous DMSO and used to determine the molar absorptivity of each compound. For fluorescence measurements, probe solutions with 0.1 absorbance units were used to minimize inner filter effects.

Previous studies have shown that this solvent mixture boosts fluorescence intensity and is well tolerated by rodents. Additionally, the dyes and their peptide conjugates are soluble in this solvent mixture, providing a common medium for spectral measurements. Table 1 below summarizes the spectral properties of the fluorescent compounds. Conjugation of the probes with the peptides did not alter their spectral properties in dilute solutions. Thus, the dyes and their conjugates were used for in vivo studies using the same excitation and emission wavelengths, as demonstrated in previous studies.

TABLE 1

Spectral properties of the fluorescent compounds in 20% aqueous DMSO.

| Compound | SEQ ID NO: | $^{ab}\lambda_{max}$ (nm) | $^{em}\lambda_{max}$ (nm) | $^{ab}\epsilon_{max}$ (cm$^{-1}$Mol$^{-1}$) |
|---|---|---|---|---|
| Cypate | — | 786 | 811 | 244,400 |
| Cypate-3 | — | 684 | 705 | 141,242 |

TABLE 1-continued

Spectral properties of the fluorescent compounds in 20% aqueous DMSO.

| Compound | SEQ ID NO: | $^{ab}\lambda_{max}$ (nm) | $^{em}\lambda_{max}$ (nm) | $^{ab}\epsilon_{max}$ (cm$^{-1}$Mol$^{-1}$) |
|---|---|---|---|---|
| Cyp-GRD | 6 | 789 | 813 | 237,680 |
| Cyp-RGD | 9 | 789 | 811 | 213,726 |
| Cyp-cyclo-GRD | 7 | 785 | 811 | 177,000 |
| Cyp-3-GRD | 10 | 684 | 703 | 128,538 |

A549 Tumor Cells Express $\alpha_v\beta_3$ Integrin

The human non-small cell carcinoma cell line, A549, is widely used to study the role of integrins in normal and pathophysiological processes. The A549 cells were purchased from American Type Culture Collection (ATCC; Manassas, Va.) and grown in 75 cm tissue culture flasks or on Lab-Tek chambered slides in Ham's F12K medium with 2 mM L-glutamine supplemented with 1.5 g/L sodium bicarbonate, 10% fetal calf serum, 100 units/ml penicillin and 100 units/mL streptomycin. To confirm the presence of ABI in A549 cells, Western blot analysis and immunohistochemistry were performed.

For Western blot analysis, the cells were lysed in radioimmunoprecipitation assay (RIPA) buffer (10 mM Tris-HCl, pH 8.0, 150 mM NaCl, 1% Igepal CA-630, 1 mM PMSF) for 15 min on ice and centrifuged at 10,000×g for 10 min at 4° C. to remove insoluble material. Protein concentration was determined by the Bio-Rad protein assay (Bio-Rad, Inc., Benicia, Calif.) per manufacturer's instructions. Cell lysate containing 20 μg of protein was mixed with two volumes of sample buffer (Bio-Rad) and boiled for 3 min. The cell lysate was resolved by electrophoresis on a 7.5% Tris-HCl polyacrylamide gel at 150V for 45 min. The protein was transferred to polyvinylidene difluoride (PVDF) membranes and nonspecific binding was blocked by incubating in SuperBlock (Pierce Biotechnology, Rockford, Ill.) for 1 h at room temperature. The membranes were then incubated with a 1:5000 dilution of primary antibody (goat anti-$\alpha_v$ or goat anti-$\beta_3$; Santa Cruz Biotechnology, Santa Cruz, Calif.) in SuperBlock for 1 hour at room temperature. After washing in TBS-Tween, the membranes were incubated with a 1:500,000 dilution of horseradish peroxidase-conjugated rabbit anti-goat IgG (Santa Cruz). Bands were visualized by treating the membranes with SuperSignal West Dura chemiluminescent substrate (Pierce) according to manufacturer's instructions and detecting the bioluminescence with Kodak Multistation scanner.

Figure 2:
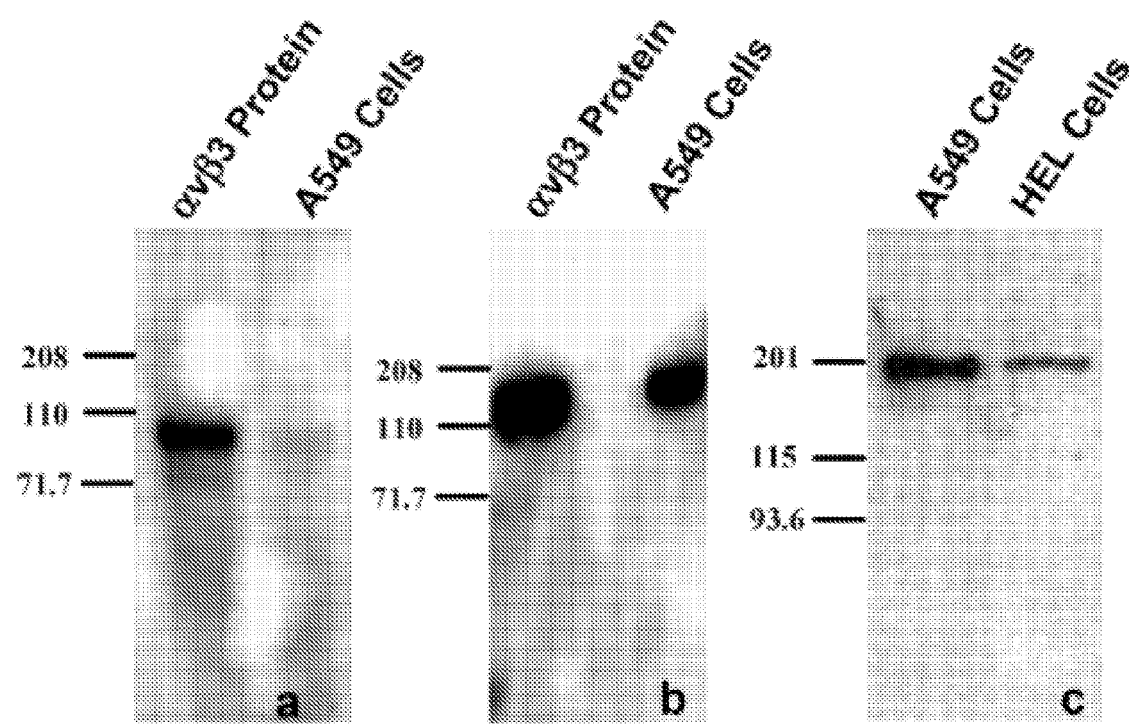
FIG. 2 presents Western blots that identify the integrin proteins present in A549 and HEL cells. Purified $\alpha_v\beta_3$ integrin and cell membranes were probed with (a) anti-$\alpha_v$, (b) anti-$\beta_3$, or (c) anti-$\alpha_{IIb}\beta_3$ antibodies.

FIG. 2 shows that A549 cells express the $\alpha_v\beta_3$ integrin subunits. Purified $\alpha_v\beta_3$ integrin protein (1.8 μg/lane) and A549 cell membrane protein (38 μg/lane) were electrophoresed, blotted, and probed with anti-$\alpha_v$ antibodies (FIG. 2a) or anti-$\beta_3$ (FIG. 2b). The $\alpha_v$ subunit is 132 kDa and the $\beta_3$ subunit is 117 kDa. The level of expression of $\beta_3$ is much higher than that of $\alpha_v$ in these cells.

For immunohistochemistry, A549 cells grown on Lab-Tek microscope slides were fixed in 3.5% paraformaldehyde for 5 min. After washing in PBS, cells were treated with 0.3% H$_2$O$_2$ for 10 min to block endogenous peroxidase activity. Cells were blocked with 5% rabbit serum in PBS for 1 h at room temperature and incubated with a 1:100 dilution of primary antibody (goat anti-$\alpha_v$ or goat anti-$\beta_3$; Santa Cruz) overnight at 4° C. After washing three times for 5 min each with PBS, the cells were incubated with a 1:200 dilution of biotinylated rabbit anti-goat secondary antibody (Vector Laboratories, Burlingame, Calif.) for 1 h at room temperature. Slides were treated with the VECSTASTAIN ABC Peroxidase Reagent Kit and signal developed using the 3,3'-diaminobenzidine (DAB) Substrate Kit, following the manufacturer's instructions (Vector Labs).

Immunohistochemistry revealed the presence of $\alpha_v$ and $\beta_3$ integrin subunits in A549 cells. Cells treated with antibodies revealed brown staining that was not seen in negative control cells that were not exposed to the primary antibodies. These results justified the choice of A549 to study ABI-mediated selective retention of the cypate-peptide in tumors.

Cypate-GRD Compound is Not Cytotoxic to A549 Cells

Cytotoxicity assays were performed using the 3-(4,5-dimethylthiazol-2-yl)-2,5-diphenyltetrazolium bromide (MTT) based in vitro toxicology assay kit (Sigma-Aldrich, St. Louis, Mo.) per the manufacturer's protocol. Briefly, A549 cells were grown in 96 well plates to 75% confluence in phenol red free Dulbecco's Modified Eagle's Medium supplemented with 10% fetal calf serum, 100 units/mL penicillin and 100 units/mL streptomycin. A concentration range (0-125 μM) of the compound to be tested was added to each well in a final volume of 100 μL/well and the cells were incubated for 24 h at 37° C. in 5% CO$_2$. After incubation, the medium was removed and replaced with 100 μL/well phenol red free medium. Absorbances at 570 nm and 690 nm were measured. MTT (10 μL) was added to each well and the cells were incubated for 2 h. MTT solubilization solution (100 μL, formazan crystals dissolved in 0.04 M HCl in 2-propanol) was added to each well and formazan crystals were dissolved by vigorous mixing. Absorbance at 570 nm and 690 nm were measured. The Δ570 and Δ690 were determined by taking the difference of the absorbances before and after the addition of MTT. The percent of viable cells, B, was determined according to the formula:

$$B = \frac{(\lambda_{\Delta 570} - \lambda_{\Delta 690})_{treated}}{(\lambda_{\Delta 570} - \lambda_{\Delta 690})_{untreated}} \times 100$$

where $\lambda_{\Delta 570}$ was the absorbance of formazan crystals at 570 nm and $\lambda_{\Delta 690}$ was background at 690 nm.

Figure 3:
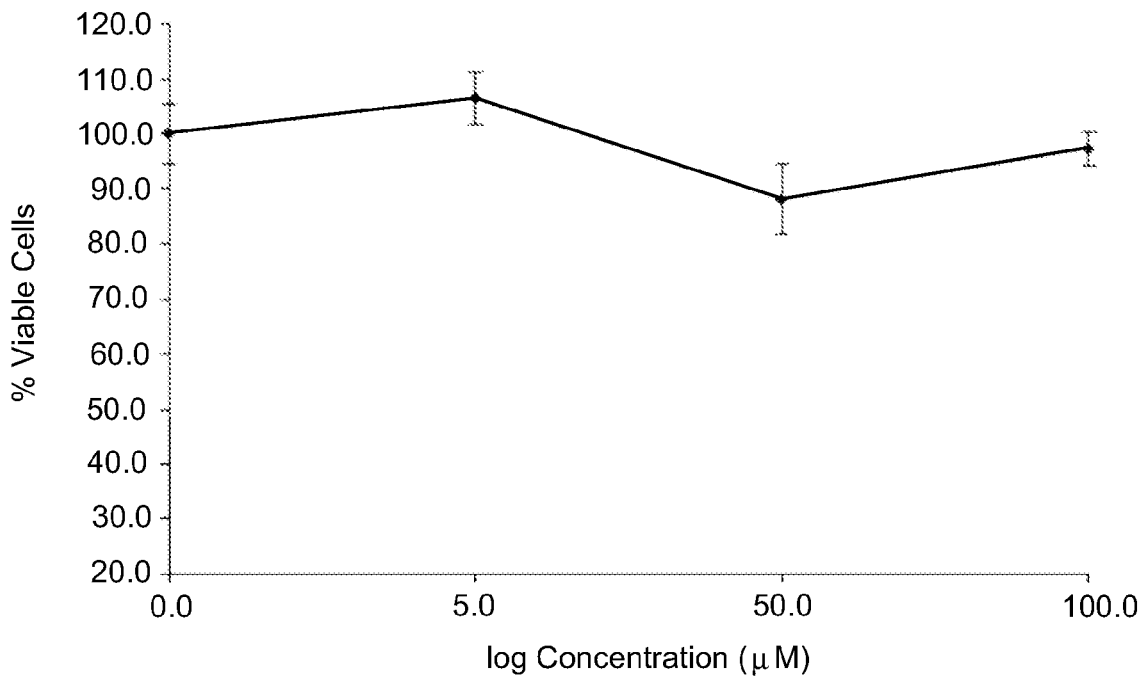
FIG. 3 illustrates that cypate-GRD is not cytotoxic to A549 cells. The percent of viable cells is shown after incubation without or with different concentrations of cypate-GRD.

The conventional MTT protocol typically involves background subtraction at 690 nm from the absorbance at 570 nm. However, the data collected were not consistent with this procedure because of interference from the tail absorption of the NIR probe at 690 nm. This resulted in proportional increase in the background subtraction signal with increasing probe concentration, which yielded false-positive cytotoxicity data. To circumvent this problem, the background absorbance at 690 nm was adjusted by running parallel experiments with and without MTT. The adjusted absorbance was obtained by subtracting the pre-MTT absorbance from the post-MTT value. It was also observed that eliminating phenol red from the cell culture media gave reproducible results. With these considerations, a reliable procedure was developed for determining the cytotoxicity of NIR dye conjugates of biomolecules. The results show that cypate-GRD did not induce cell proliferation or cytotoxicity, up to 100 μM solution in 20% aqueous DMSO (see FIG. 3).

Cypate-GRD Compound is Internalized by A549 Cells

Cells were grown on LabTek microscope slides, as described above. The medium was removed and cells were incubated at 4° C. or 37° C. in PBS containing 1 μM of one of the peptide conjugates for 30 min. For competition studies, the cells were pre-incubated with 1 μM unlabeled cyclo [RGDfV] [SEQ ID NO:1] or octreotate for 15 min at 4° C. prior to the addition of peptide compound. The cells were further incubated at 37° C. for 4 h and visualized with a Zeiss LSM510 system using a 633 laser and an LP650 filter.

For antibody blocking studies, cells were preincubated for 30 min at room temperature with 10 μg/ml function-specific monoclonal antibodies anti-$α_v$ or anti-$β_3$ integrin subunits (Molecular Probes; Eugene Oreg.) before addition of 1 μM of a cypate-peptide conjugate. For nuclear staining, 0.1 μM TOPO-1 (Molecular Probes) was mixed with mounting medium and applied to the cells. All cells were visualized on an Olympus FV1000 microscope equipped with the appropriate bandwidth filters for cypate conjugates (or cypate-3 conjugates) and TROPO-1.

Cyp-3-GRD [SEQ ID NO:10] internalized in A549 cells at 37° C., but it did not translocate into the nucleus (data not shown). In contrast, the conjugate remained in the peripheral region of the cell membrane of cell incubated at 4° C. These features are reminiscent of G protein-coupled receptor-mediated endocytosis of ligands. Furthermore, the uptake of Cyp-3-GRD into A549 cells was specifically inhibited by the commercially available ABI-binding cyclic peptide, cyclo [RGDfV] [SEQ ID NO:1], but not by the non-ABI ligand, octreotate (data not shown).

Figure 4:
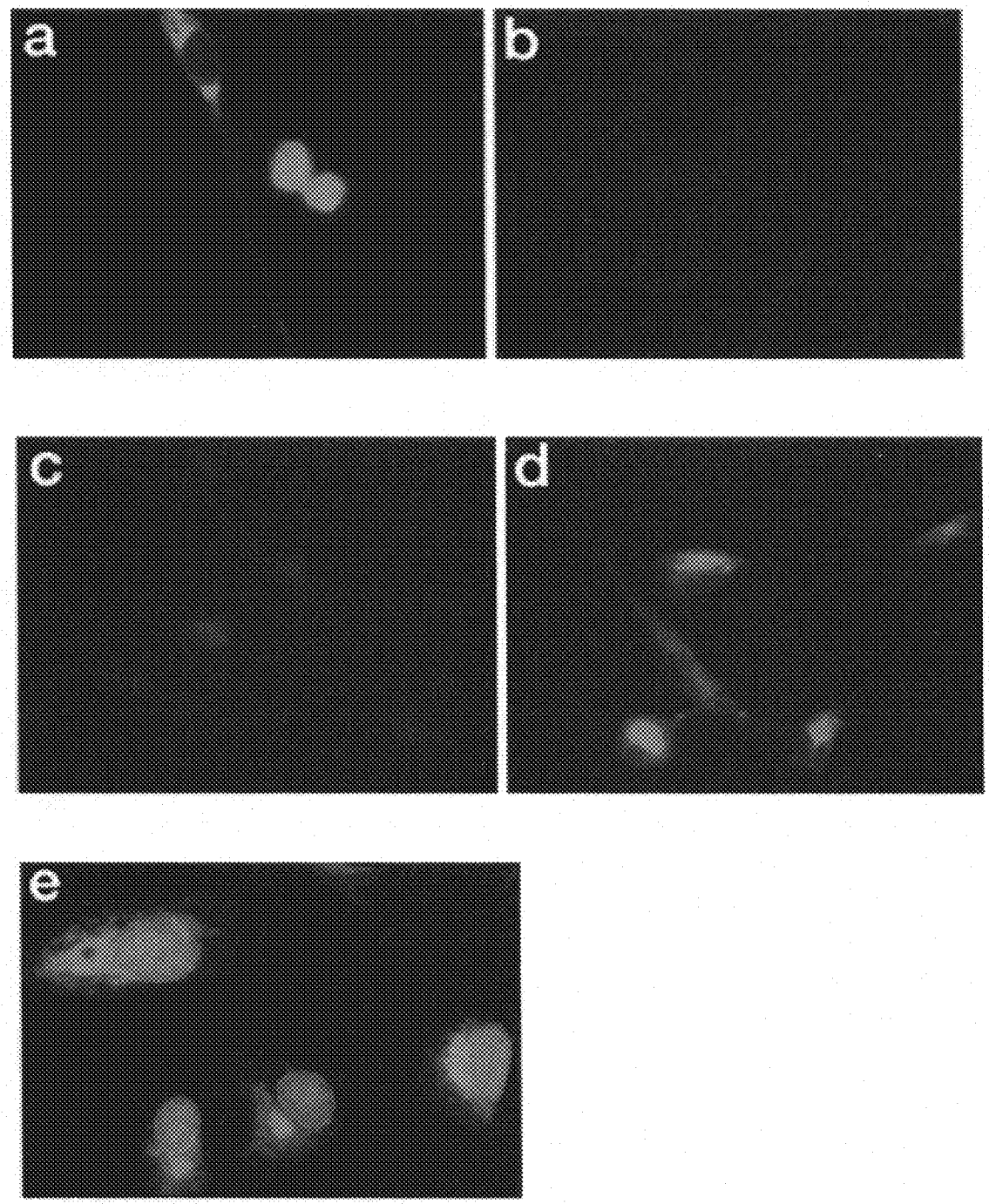
FIG. 4 illustrates the cellular uptake of cypate-GRD. (a) Cyp-GRD was internalized following incubation at 37° C. (b) Preincubation with inhibitor RGD peptide blocked uptake of Cyp-GRD. (c) Preincubation with anti-$\beta_3$ monoclonal antibody blocked uptake of Cyp-GRD. (d) Preincubation with anti-$\alpha_v$ monoclonal antibody partially blocked internalization of Cyp-GRD. (e) Distribution of cypate-GRD (red) and TROPO-1 (blue, nuclear stain), showing that the probe was not localized in the nucleus. Images in b-d were normalized to the highest fluorescence intensity from (a).

FIG. 4a shows that the Cyp-GRD [SEQ ID NO:6] conjugate was internalized by A549 cells at 37° C. The image shows a mature cell with a well-defined nucleus and a mitotic cell at the last stages of cell division with the probe uniformly partitioned between the two dividing cells. The uptake of Cyp-GRD was inhibited by cyclo[RGDfV] [SEQ ID NO:1] (FIG. 4b). To further assess the mechanism of internalization, antibody blocking studies were preformed by preincubating the cells with functional antibodies before addition of cypate-GRD. Uptake of the Cyp-GRD was inhibited by anti-$β_3$ antibodies (FIG. 4c) and to a lesser extent by anti-$α_v$ antibodies (FIG. 4d). These data suggest that the $β_3$ integrin subunit plays a vital role in the binding of Cyp-GRD and probably initiates the receptor-specific internalization of the probe in A549 cells. The high expression of the $β_3$ subunit relative to the $α_v$ subunit in A549 cells (see FIG. 2), support the dominant role of $β_3$ integrin subunit in the molecular recognition of Cyp-GRD. The fact that Cyp-GRD did not translocate to the nucleus (FIG. 4e) further augments its value as a molecular imaging probe.

Cypate-GRD Compound is Selectively Retained by A549 Tumor

All in vivo studies were performed in compliance with the Washington University in St Louis Animal Study Committee's requirements for the care and use of laboratory animals in research. Nude mice (18-22 g) were anesthetized with xylazine/ketamine cocktail via intraperitoneal injection and placed in a supine position. The mice were injected subcutaneously with A549 cells (1×10$^6$) in the lower back of the mice. Tumor masses were palpable at 5-7 days post implant, which reached 5 mm in 10-15 days. Prior to injection of the probe, the mice were anesthetized as described above. A 29-gauge needle was used to inject the probes into the mouse via the lateral tail vein. The molecular probe (100 μL) was injected via the lateral tail vein at 0.3 μmol per kg of body weight. For the blocking studies, equimolar amounts of Cyp-GRD [SEQ ID NO:6] and cyclo[RGDfV] [SEQ ID NO:1] were constituted in a vial, and doses of 0.3 μmol per kg of body weight were injected into the A549 tumor-bearing mice.

A non-invasive in vivo continuous wave fluorescence imaging apparatus was used to visualize the distribution and preferential tissue uptake of the cypate-peptide molecular beacons in the nude mice (Achilefu (2004) Technol. Cancer Res. Treat. 3:393-409, incorporated herein by reference). Light from two laser diodes of nominal wavelength 780 nm and nominal power of 50 mW was launched into a fiber optic bundle. Two laser diodes were used to produce as much uniform illumination of the whole animal or organ parts as possible. The nominal 50 mW of incident power was reduced to about 44 mW at the output of the fiber optic bundle. A de-focusing lens in position after the bundle expanded the beam such that nearly the whole animal was illuminated. A Photometrics CCD camera (16 bit, 1024×1024 pixel, back illuminated, thermoelectric Peltier cooled with forced air) was used to capture the emitted photons. An interference filter (830 nm) was mounted in front of the CCD camera input lens such that only emitted fluorescent light from the contrast agent was imaged. Real-time acquisition, display and data processing software (WinView/32) was used to obtain the optical image. The samples were dissolved in 20% aqueous DMSO and animals were injected with doses of 0.3 μmol/kg body weight via the lateral tail vein. Injected volumes were 100 μL for each mouse. Data analysis consisted of subtracting (pixel by pixel) the pre-injection image from the post injection images, and displaying the false color results. Integration of the relative fluorescence intensities of tumor vs. surrounding tissues indicated the extent of selective uptake of the contrast agent. At the completion of the study, the mice were euthanized and some organ parts were excised and rinsed with water. The tissues were placed under the CCD camera and the fluorescence emission from each organ was measured after excitation with the 780 nm laser sources. Tissue parts, instead of whole organs, were used to minimize problems associated with depth-dependent non-linear fluorescence emission. A statistical program in the WinView package was used to estimate the mean fluorescence intensity per organ part.

Figure 5:
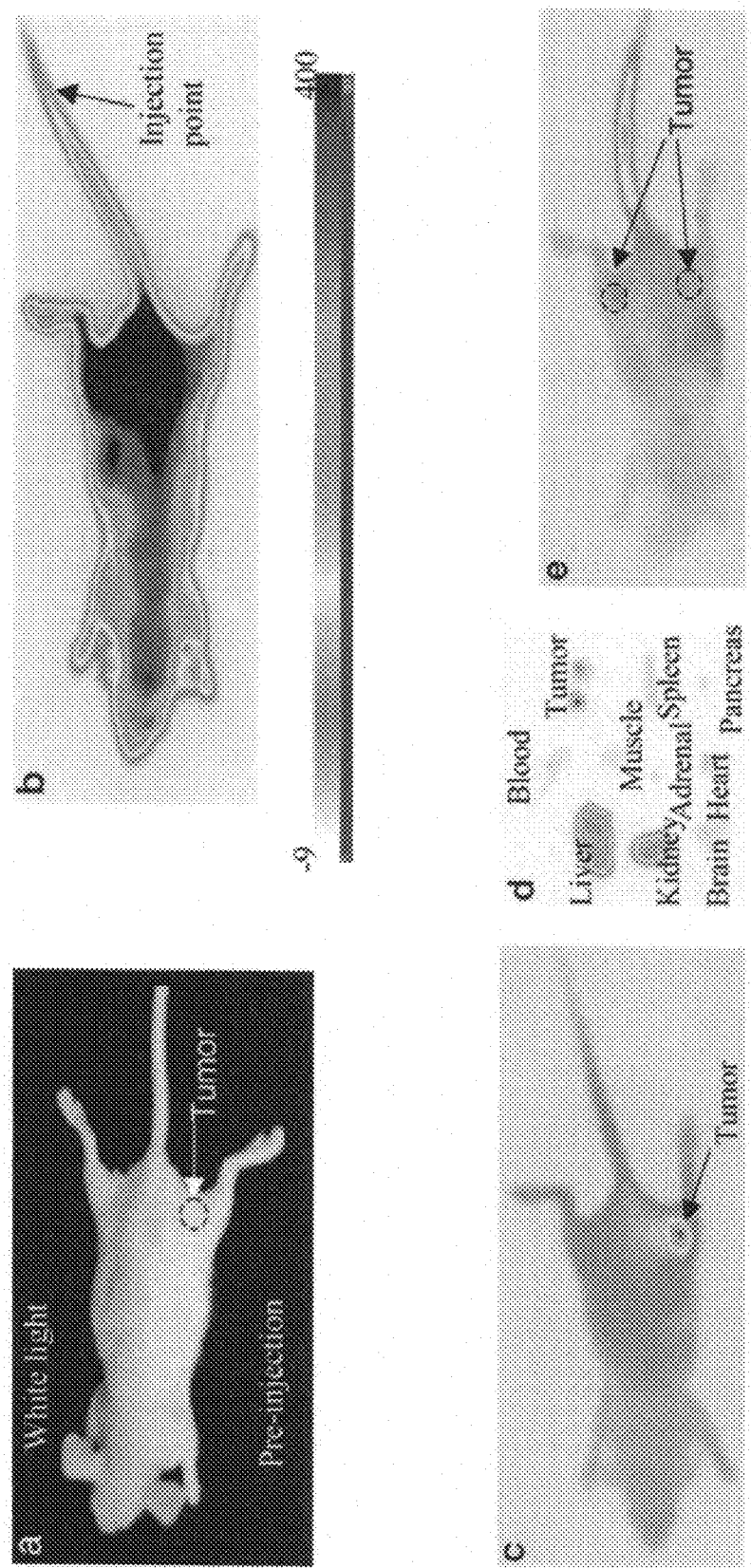
FIG. 5 illustrates the in vivo distribution of cypate-GRD in mice. (a) White light image of A549 tumor-bearing mouse. (b and c) Fluorescence images of cypate-GRD peptide conjugate in A549 tumor-bearing mouse at 5 min (b) and 24 h (c) post injection. (d) Ex vivo image of selected organ parts at 20 h post injection. (e) Inhibition of the tumor uptake of cypate-GRD by inhibitor cylic RGD peptide. All images are on the same relative fluorescence intensity scale (−9 to 400).

Injection of the Cyp-GRD probe into A549 tumor-bearing mice (~5 mm diameter tumors), and subsequent time-sequence optical imaging, showed preferential uptake of the probes in the tumor (FIG. 6) relative to normal tissues. The barely palpable tumor was located on the lower left flank of the mouse (FIG. 5a). The whole animal fluoresced up to 2 h after injection of the probe before the probe started to clear from blood and nontarget tissues (FIG. 5b). The selective uptake of the molecular beacon in tumor became obvious after 8 h post injection when the probe significantly cleared from non-target tissues and by 24 h post injection, the tumor was clearly visible (FIG. 5c). The observed slow clearance of Cyp-GRD from blood supports the notion that the circulating probe was repeatedly taken up by the ABI-positive cells because integrin proteins translocate from the cytoplasm back to the cell surface after internalization of the ligand. This rebound effect is similar to the internalization mechanism by G protein-coupled receptors that has the positive effect of concentrating the receptor-specific probes and drugs in target tissues. Ex vivo analysis of the normalized fluorescence intensity (relative to blood) clearly showed a high density of the fluorescence emission from the tumor tissue (FIG. 5d). Coinjection of equimolar concentrations of Cyp-GRD [SEQ ID NO:6] or cyclo[RGDfV] [SEQ ID NO:1] blocked the uptake of Cyp-GRD into the tumor at 24 h (FIG. 5e).

Figure 6:
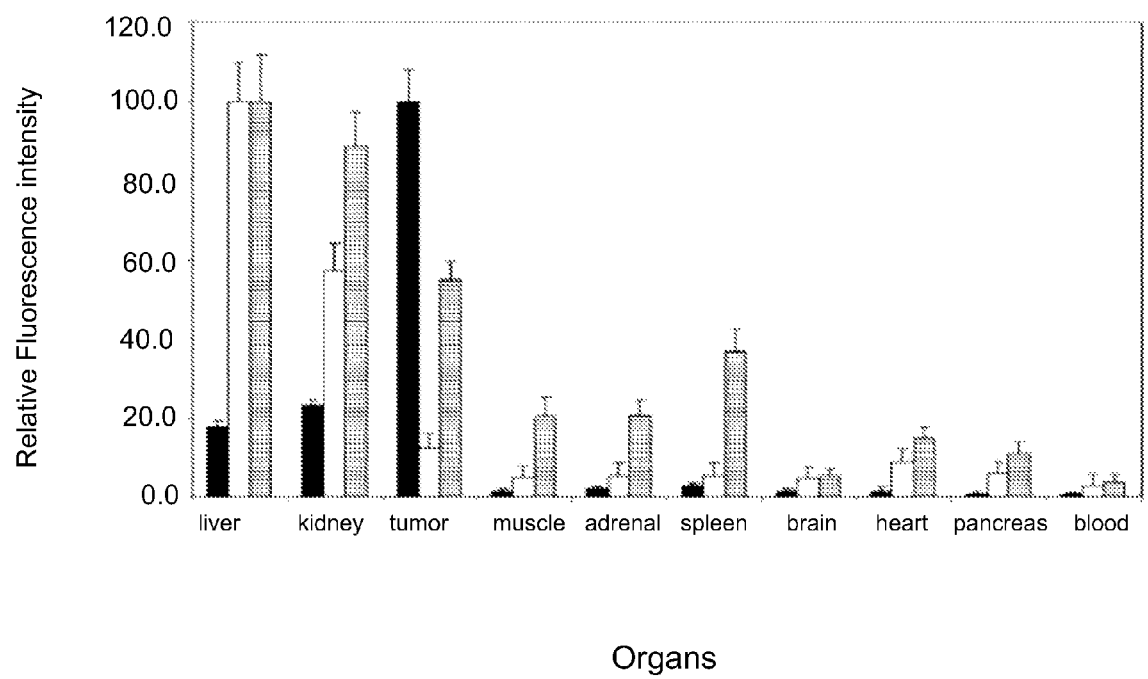
FIG. 6 illustrates the distribution of cypate-peptide conjugates in selected organs of A549 tumor-bearing mice. The relative fluorescence intensities of cypate-GRD (black bars), cypate-RGD (white bars), and cyclic cypate-RGD (striped bars) are presented. The fluorescence intensity was relative to blood (n=3).

The distribution of Cyp-RGD [SEQ ID NO:5] and Cyp-cyclo-RGD [SEQ ID NO:7] were also evaluated in A549 tumors in vivo. FIG. 6 shows that the tumor uptake of these beacons was low, compared with Cyp-GRD at 24 h post injection. While the retention of the cyclic Cyp-RGD in the tumor was higher by a factor of three compared with the linear Cyp-RGD analogue, its accumulation in nontarget tissues was equally high. The linear RGD peptide conjugate was primarily retained in the liver and the kidneys. Therefore, deletion of glycine from the RGD peptide sequence favored its binding to ABI, presumably through initial binding to the $\beta_3$ integrin subunit.

The hypothesis that the "RD" motif was solely responsible for the tumor uptake was further tested by injecting $^{111}$In-DOTA-GRD [SEQ ID NO:15] (120 µCi; 1 Ci=37 GBq) into A549 tumor-bearing mice. Time-sequence scintigraphy showed a rapid renal clearance of the probe, with nearly all of the material localized in the bladder at 30 min after injection. Furthermore, the precursor dye cypate was not retained in the tumor, but was rapidly cleared from blood by the liver within 4 h after infection. This is also in agreement with the in vitro data that showed that cypate did not internalize in A549 cells. These observations demonstrate the synergistic effects of the dye and peptide to enhance the retention of RD compounds in A549 cells and tumor tissue.

To evaluate the extent of nonspecific uptake, the non-conjugated NIR fluorescent probe (cypate), indocyanine green, and a non-ABI-avid cypate-octapeptide conjugate (cytate) were injected into different tumor-bearing mice. None of the three non-ABI-specific probes were retained in the A549 tumor tissue and all predominantly accumulated in the liver within 1 h post injection. This distribution was similar to the hepatobilliary excretion pathway observed in normal rats and in humans using indocyanine green.

Figure 7:
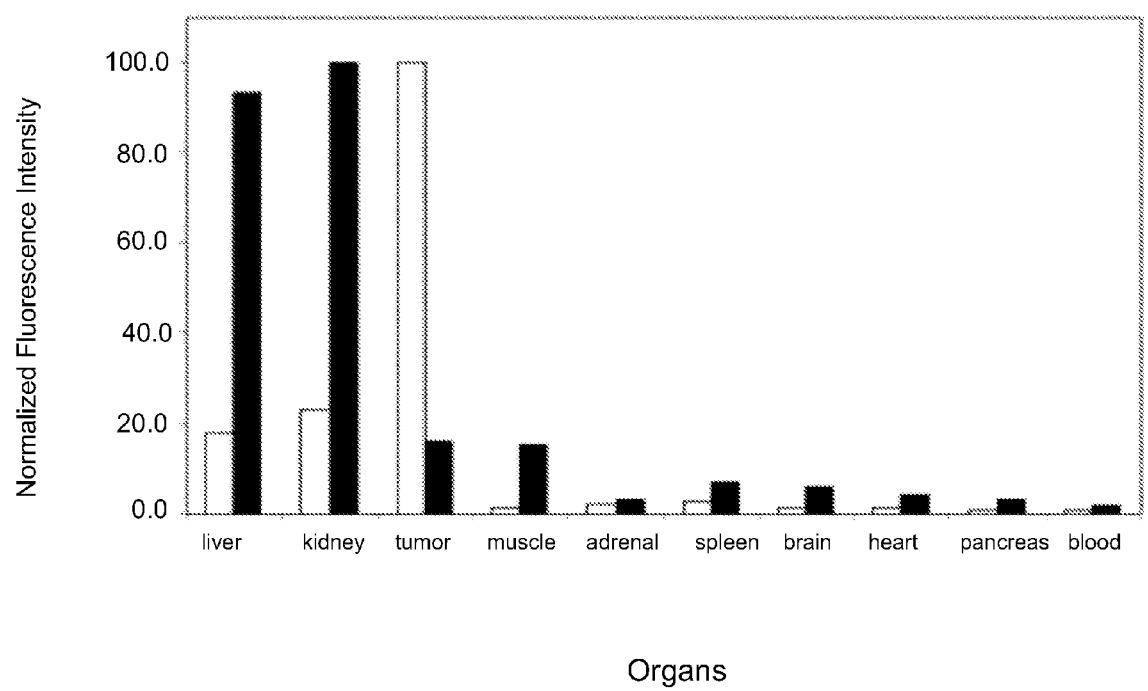
FIG. 7 illustrates the effect of inhibitor cyclic RGD peptide on the distribution of cypate-GRD in selected organs of A549 tumor-bearing mice. Presented is the normalized fluorescence intensity with (black bars) or without (white bars) the cyclic RGD peptide inhibitor, cyclo[RGDfV] [SEQ ID NO: 1]. The fluorescence intensity was normalized to the organ with highest intensity.

To further demonstrate the specificity of the RD motif, the commercially available RGD peptide analogue, cyclo (RGDfV) [SEQ ID NO:1], which has high specificity and affinity for ABI, was used to competitively inhibit the uptake of the optical probe. Co-injection of equimolar concentrations (0.3 µmol/kg body weight) of Cyp-GRD and cyclo (RGDfV) [SEQ ID NO:1] significantly blocked Cyp-GRD uptake in the tumor at 24 h post injection (FIG. 5e and FIG. 7). The GRD peptide [SEQ ID NO:8] alone, however, was unable to block the Cyp-GRD uptake.

These results clearly demonstrate the synergistic effects of the cypate dye and the GRD peptide for ABI molecular recognition. The findings suggest the potential of using carbocyanine probes as optical scaffolds for designing biologically active molecules.

Distribution of Cypate-GRD in Tumor Tissue in Heterogeneous and Correlates with Mitochondrial NADH The non-invasive optical imaging method described above reports on probe distribution within a few millimeters from the tissue surface. The isotropic fluorescence emission captured by the CCD camera appeared to indicate uniform distribution of the probe in tumor tissue. However, the heterogeneity of tumor cells suggests that overexpression of ABI may not be uniform within the tumor tissue. To explore this possibility, a snap-freeze method that preserves a tissue and its redox state for subsequent characterization by high resolution ex vivo fluorescence imaging was used. The method is akin to in situ histologic staining except that fluorescence from the probe retained by the tumor and other endogenous fluorophores is used to characterize the tissue. After performing planar fluorescence imaging, the animal under anesthesia was immersed in liquid nitrogen for 10 min and the tumor tissue was surgically excised, embedded in an ethanol glycerol-water mixture (10:30:60, −30° C.) and mounted in a redox scanner for 3D surface fluorometric scanning. The frozen tumor sample was imaged in the Z direction by chipping the tumor tissue at 100 µm intervals. A bifurcated optical fiber bundle (7 quartz fibers, 70 µm core diameter for each, 1 fiber for emission in center, 6 fibers for excitation around the emission fiber) was stepped across the tissue surface at a fixed distance from the tissue surface (70 µm). The filters for the fluorescence excitation and emission of the probe, NADH and FP were chosen based on the absorption and emission spectra of each fluorophores. Using a Mercury Arc lamp and a 785 nm laser diode as the excitation light sources, the fluorescent signals of FP (filters: Ex: 440DF20, Em: 520DF40), NADH (filters: Ex: 365HT25, Em: 455DF70) and Cyp-GRD (filters: Ex: 780DF10, Em: 830DF20) were imaged at various depths of the tumor. The scanning was performed at 128×128 steps that covered 1.024×1.024 cm$^2$ area (80 µm per step). The fluorescence of FP, NADH and Cyp-GRD were recorded digitally on a PC and reconstructed with MATLAB software. The redox ratio of NADH/(FP+NADH) calculated with MATLAB represented the reduced state of the mitochondria.

Figure 8:
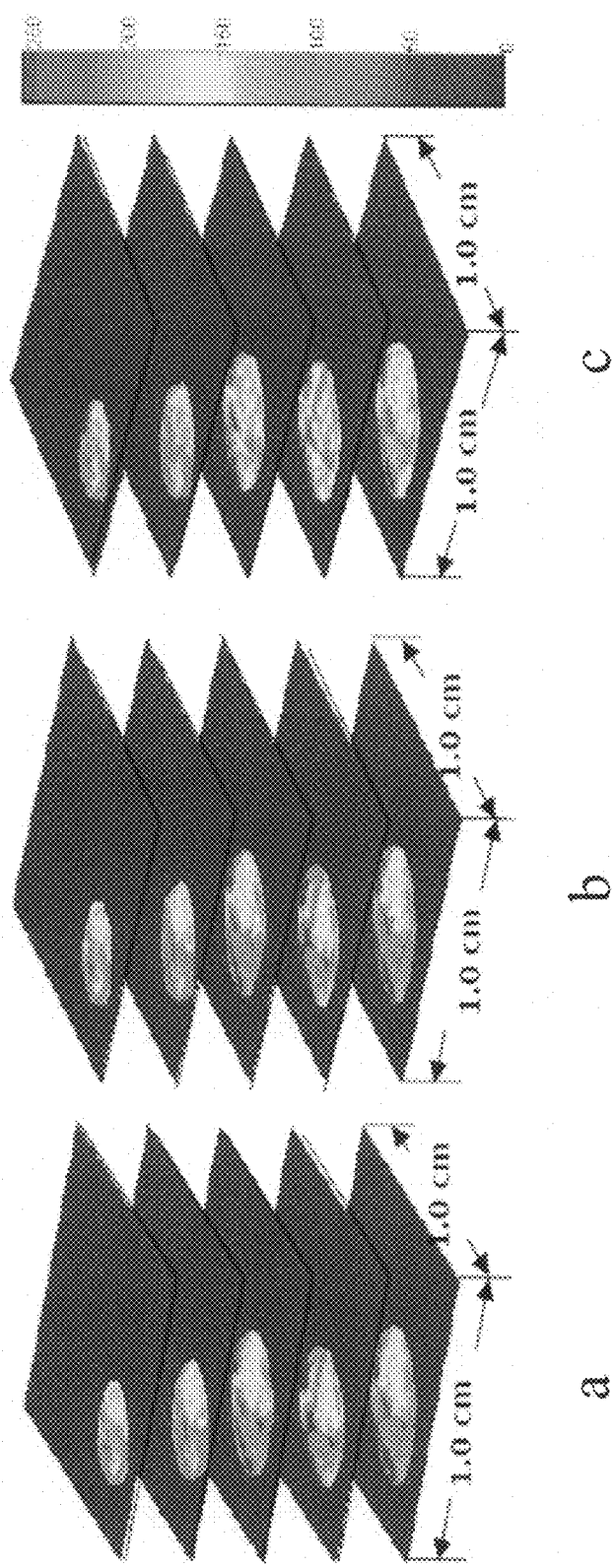
FIG. 8 presents ex vivo stacked fluorescence images of cypate-GRD and mitochondrial proteins in A549 tumor tissue at different depths. (a) Mitochondrial flavoproteins, (b) mitochondrial NADH, and (c) cypate-GRD are shown at depths of 300 μm, 400 μm, 700 μm, 800 μm, and 900 μm (from top to bottom of the figure)

FIG. 8 shows the stacked image of the distribution of mitochondrial flavoproteins, mitochondrial NADH, and Cyp-GRD and demonstrates the heterogeneity of the probe distribution at different tumor depths in the Z direction. The tumor cells were typically mixed with normal (stromal) cells that have low uptake of the beacon (blue to green regions in FIG. 8a). Although the heterogeneous nature of tumors allows them to evade treatment, targeting these abnormal cells with ABI-specific drugs can selectively destroy the tumor cells while preserving healthy tissues.

Figure 9:
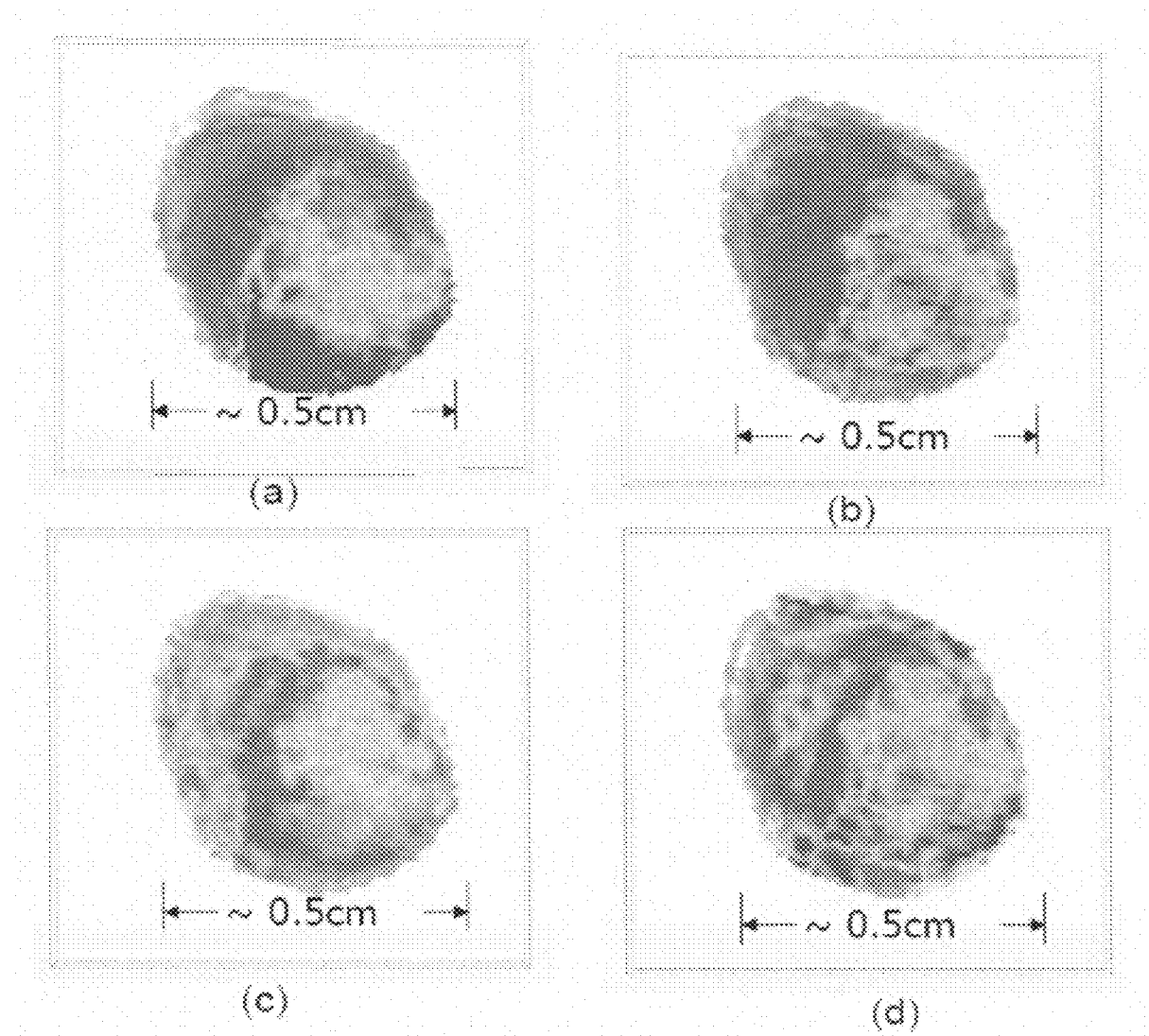
FIG. 9 presents three-dimensional fluorescence images of cypate-GRD and mitochondrial proteins in ex vivo A549 tumor tissue 24 h after injection. (a) Mitochondrial flavoprotein (Fp), (b) NADH, (c) NADH/(Fp+NADH) redox ratio (reduced state), (d) and cypate-GRD.
Figure 10A:
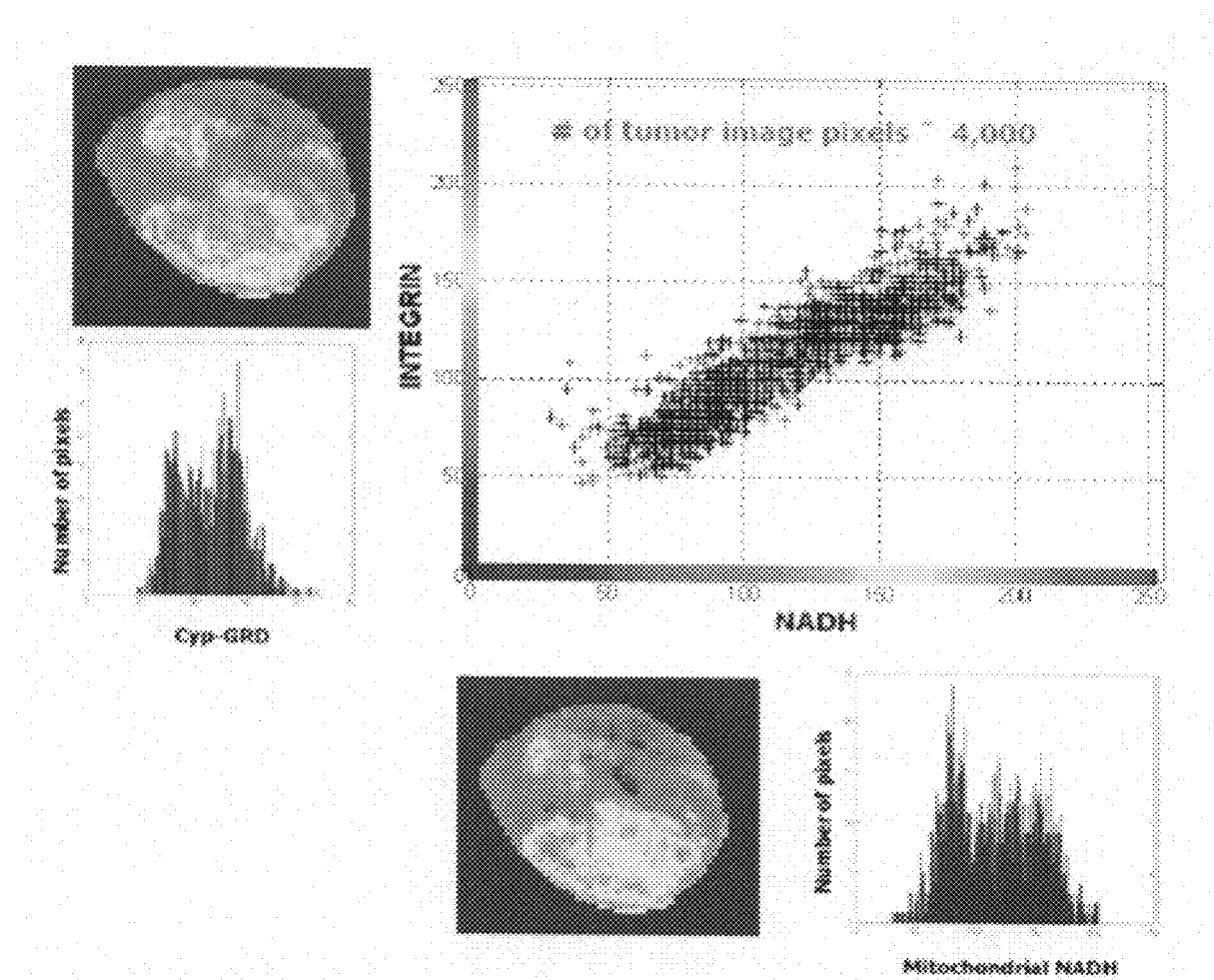
FIG. 10 presents the correlation between the level of mitochondrial NADH expression and the distribution of cypate-GRD in A549 tumor at 24 h postinjection. Correlations at the 400 μm scan surface (a) and the 900 μm scan surface (b) are presented.
Figure 10B:
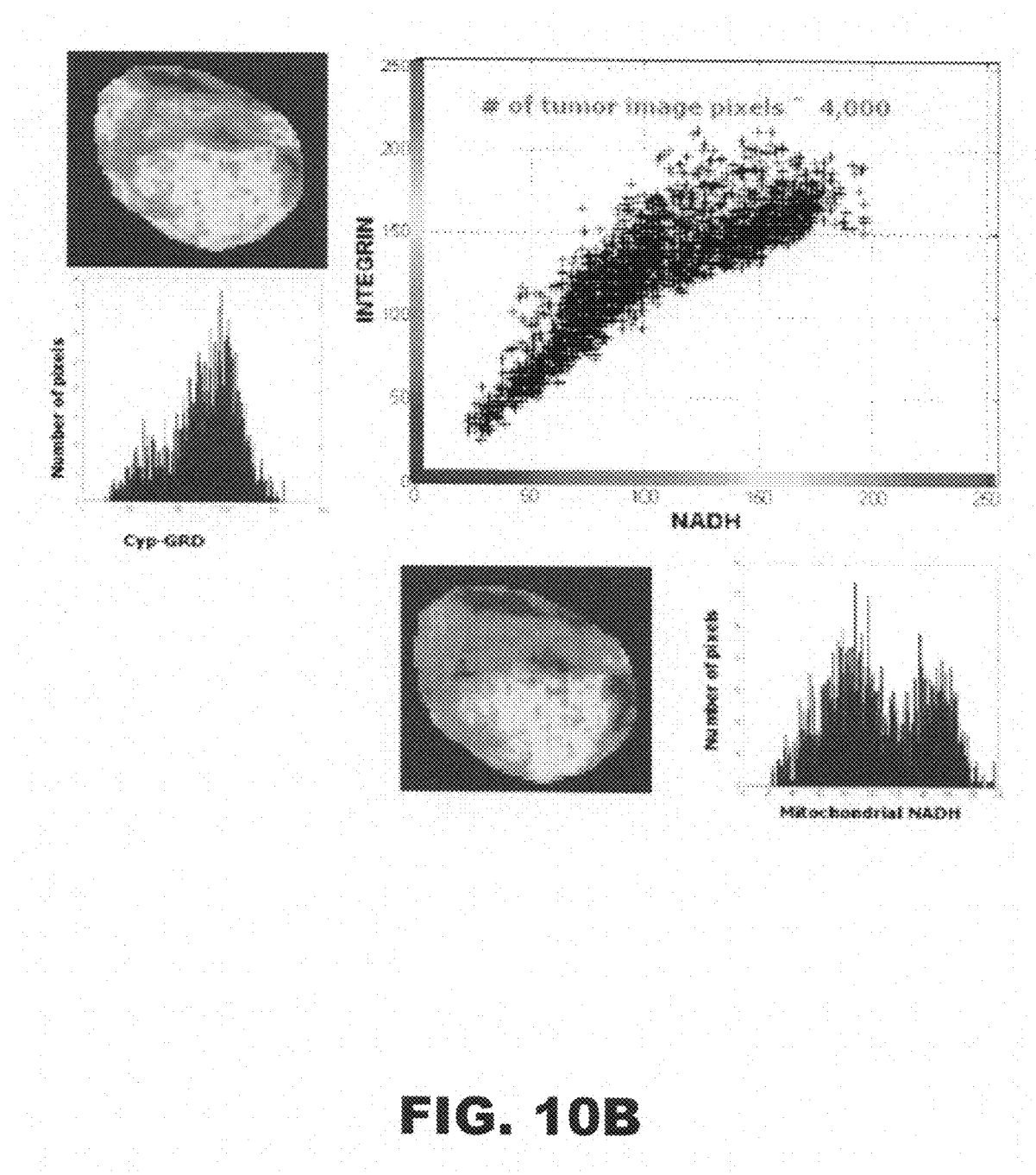

As described previously, the snap-freeze method also provides information about the metabolic state of the cells through measurement of mitochondrial NADH and FP levels. The ratio of these biomolecules in mitochondria is an index of cellular metabolic activity. The large differences in the excitation (365, 440, and 780 nm) and emission (455, 520, and 830 nm) wavelengths of NADH, FP, and Cyp-GRD, respectively, minimized spectral overlap. This facilitated imaging the distribution of all three molecules in the same tissue and correlating their relative expression levels with metabolic state of the tumor. FIG. 9 shows the heterogeneous 3D fluorescence images of mitochondrial FP, NADH, and Cyp-GRD at the same tumor depth. A spatial correlation between the reduced state (high NADH) and Cyp-GRD distribution was observed at different tumor depths (FIGS. 10a and 10b). In contrast, oxidized FP expression (oxidized state), and the overall oxidized (FP/(FP+NADH)) and reduced (NADH/(FP+NADH)) state ratios of the tumor were less spatially correlated to Cyp-GRD distribution. The rationale for strong correlation with NADH but not with FP or redox ratios is not clear at this time. A possible mechanism could involve NAD-mediated oxidation of the polymethine chain of cypate in vivo and the subsequent conversion of the non-fluorescent NAD to NADH. This process would result in the correlation of the local Cyp-GRD distribution with NADH but not the global redox state of the tumor.

Example 2

Design, Synthesis, and Evaluation of NIR fluorescent Cyclic RGD Peptides for Targeting Integrins Biomolecules possessing the RGD peptide sequence are known to bind to the integrin family of cell-surface receptors. These receptors mediate a host of pathophysiological conditions in humans. For this reason, interest in the development of novel RGD peptides has increased in biomedical research. Most research efforts have focused on diverse linear and cyclic RGD peptides and their peptidomimetics. In particular, the cyclic RGD peptides are very attractive because the cyclization is known to improve binding affinity, selectivity, enzymatic stability, pharmacodynamics, and pharmacokinetics in vivo. In particular, the cyclic RGD pentapeptide, cyclo[RGDfV] [SEQ ID NO:1], and its analogues have received much attention because they bind integrins with high affinity.

Labeling these peptides with fluorescent dyes would provide a means to detect, localize, and monitor the functional status of diseases. Because of the deeper penetration of light in tissue at the near infrared (NIR) wavelengths between 700 and 900 nm, conjugation of NIR fluorescent dyes with the peptide would yield compounds that are useful for imaging deep tissues in small animals and humans.

Herein, the design, synthesis, and evaluation of some lactam-based and disulfide-based cyclic RGD peptides that are labeled with a NIR fluorescent, cypate, are reported.

Molecular Design and Synthesis

Figure 11:
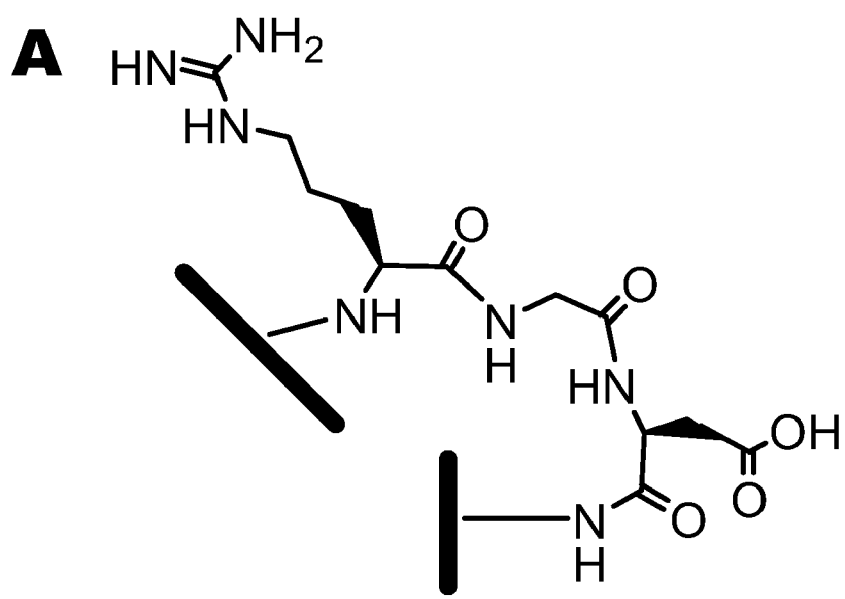
FIG. 11 illustrates the structures of the (a) RGD peptide unit, (b) cypate dye, (c) a lactam-based cyclic cypate-RGD peptide, and (d) a di-cysteine cyclic cypate-RGD peptide.
Figure 11:
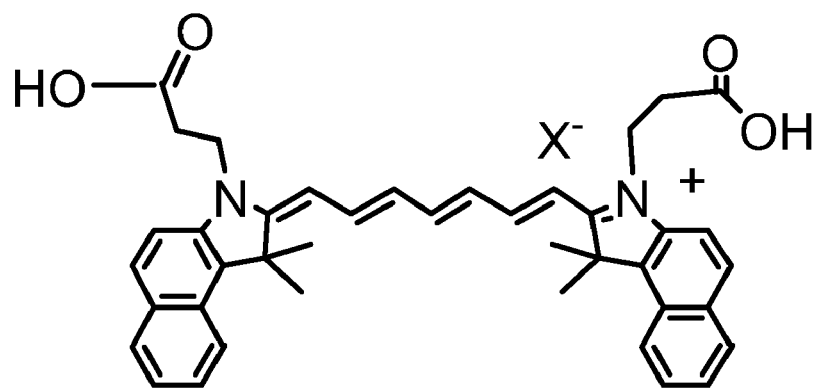
Figure 11C:
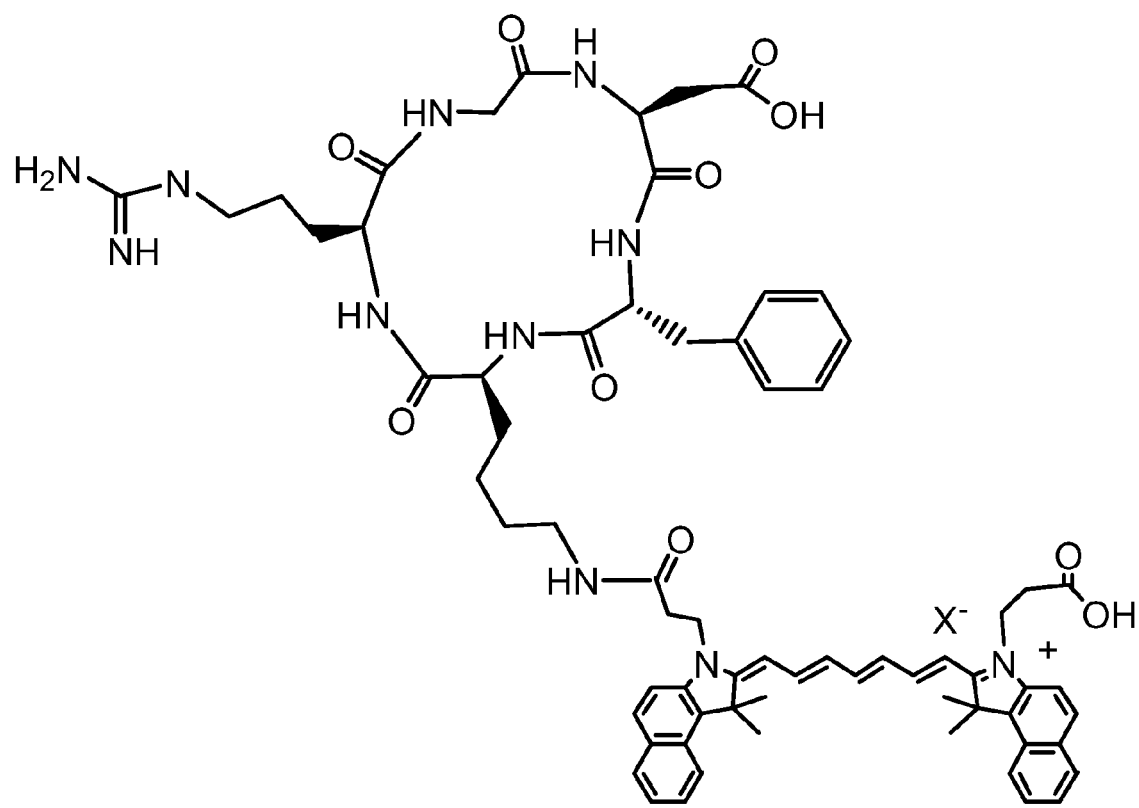
Figure 11D:
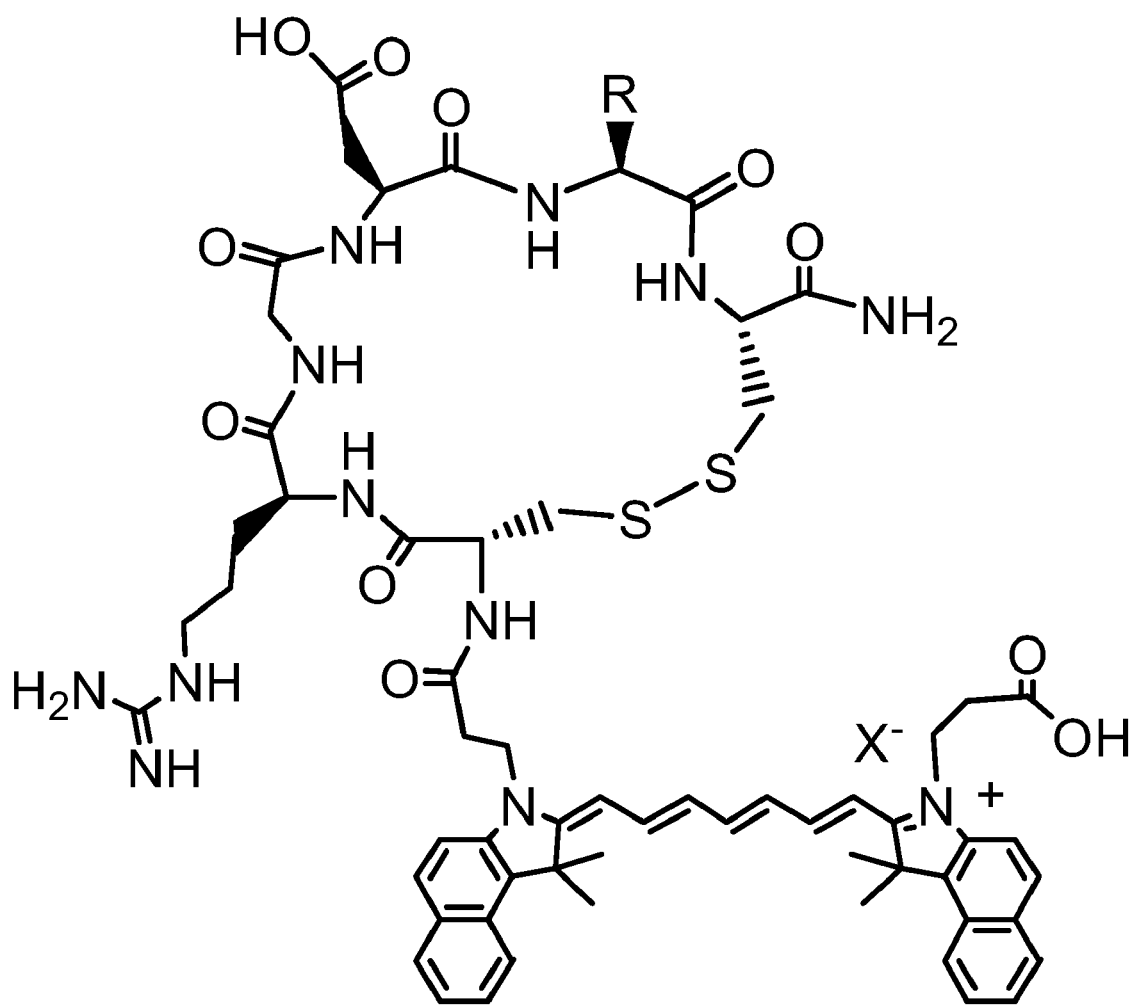

FIG. 11 shows the two different types of cyclic RGD peptides that were prepared. The first type was the lactam-based cyclic pentapeptide (see FIG. 11c) that included peptides obtained by the insertion of lysine or substitution of the valine residue with lysine to afford a reactive site for fluorescent labeling (see Table 2). The second type was based on a cyclic RGD framework with two cysteine residues at both N- and C-termini (see FIG. 11d). Several compounds of this type were designed based on the ring size with different numbers of amino acids and variation of one amino acid residue (see Table 2). As detailed above, a dicarboxylic acid-containing carbocyanine (cypate) was used as a NIR fluorescent probe to label the peptide at the N-terminus of disulfide cyclic peptide or the ε-amino group of lysine.

All the peptides were assembled manually on Rink amide MBHA resin (0.15 g, 0.4 mmol/g) using the conventional Fmoc chemistry in a glass reaction vessel. The coupling reactions were carried out by adding a pre-activated solution of N-α-Fmoc-protected amino acid (3 equiv), HOBT (3 equiv), HBTU (3 equiv), and DIEA (6 equiv) in anhydrous DMF (10 mL/g resin) into the resin (1 equiv) and swirling for 2 h. The progress of the coupling was monitored by Kaiser test. The Fmoc protecting groups were removed by two 10 min treatments with a piperidine/DMF solution (20%). The resin was washed by swirling in methanol (1 min, 2 times), followed by DMF (1 min, 6×). The resin bound di-Cys(Acm) peptide was swirled with Tl($F_3$CCOO)$_3$ (2 equiv) in DMF to form the disulfide peptide, washed with DMF (1 min, 2 times), and finally deblocked with 20% piperidine in DMF. All the crude products were purified by semi-preparative HPLC and identified by both ES-MS and analytical HPLC. They showed the corresponding [MH]$^+$, [MH$_2$]$^{2+}$ and even triple [MH$_3$]$^{3+}$ peaks in their ES-MS spectra.

A mixture of cypate (211.5 mg, 0.3 mmol), DIC (38.0 mg, 0.3 mmol), HOBT (41.0 mg, 0.3 mmol) and the resin bound disulfide RGD peptide (~0.06 mmol) in anhydrous DMF (3 mL) was swirled for 8 h. The resin was filtered, washed with DMF (1 min, 3 times), methanol (1 min, 2 times), and dried under vacuum. The resin was cleaved with TFA (3 mL, 1.5 h, 5 times). The TFA filtrate was concentrated and added to cold MBTE (10 mL). The solid precipitate was collected by filtration, washed with petroleum ether, and purified by semi-preparative HPLC to afford the desired products.

Synthesis of Cypate-Labeled Cyclic Disulfide Peptides

The protected RGD peptide sequence, i.e. Fmoc-Cys(Acm)-Arg(Pbf)-Gly-Asp(OBut)-X$_{AA}$-Cys(Acm) [SEQ ID NO:16], was first assembled on Rink amide MBHA resin (1 equiv) using the conventional Fmoc chemistry (Scheme 1). It was swirled with Tl($F_3$CCOOH)$_3$ (2 equiv) in DMF for 2 h to form the cyclic disulfide peptide, i.e., Fmoc-cyclo[Cys-Arg(Pbf)-Gly-Asp(OBut)-X$_{AA}$-Cys] [SEQ ID NO:17]. The conjugation of cypate with peptide usually afforded the monomeric and dimeric conjugates simultaneously. To increase the yield of monomeric product, 5 equivalents of Cypate were used with 3.5 equivalents of DIC and HOBT. Finally, TFA cleavage afforded the desired product, i.e., Cypate-cyclo(Cys-Arg-Gly-Asp-X$_{AA}$-Cys)-NH$_2$ [SEQ ID NO: 18]. The other cyclic disulfide RGD peptide analogs (Table 2) were synthesized using the same protocol.

Scheme 1. Synthesis of Cypate-labeling cyclic disulfide RGD peptides.

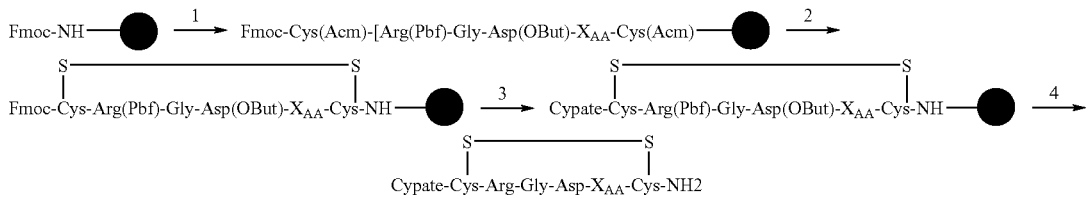

Reagents and conditions: 1. Peptide assembly using Fmoc chemistry; 2. Tl(CF$_3$COO)$_3$/DMF; 3. (a) piperdine/DMF(20%); (b) Cypate/HOBT/DIC/DMF; 4. TFA/water (95:5).

Synthesis of Cypate-Labeled, Lactam-Based, Cyclic RGD Peptides

Two lactam-based cyclic RGD peptides were designed and synthesized for comparison. As shown in Scheme 2, the pentapeptide, Cyclo-[K$^{(Cypate)}$RGDf] [SEQ ID NO:4], was assembled from Asp(OBut)-2-chlorotrityl resin. After cleavage with 1% TFA/DCM, the protected peptide was obtained and cyclized in the presence of PyBOP/HOBT/DIEA in a solution of DCM/DMF (10%). The Dde protecting group was removed with 2% hydrazine/methanol and the resulting peptide was conjugated with Cypate in the presence of DIC/HOBT in DMF. The product was cleaved with TFA/water (95:5) and purified by semi-HPLC. Similarly, a hexapeptide analog, cyclo-[K$^{(Cypate)}$RGDfV] [SEQ ID NO:7], was designed and synthesized by inserting a valine residue.

Scheme 2. Synthesis of Cyclo-[K$^{(Cypate)}$RGDf] [SEQ ID NO: 4]

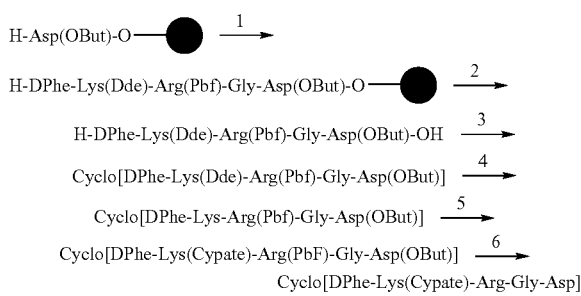

Reagents and conditions: 1.Fmoc chemistry; 2. a) TFA/DCM(1:99); b) Pyridine/DCM/Methanol; 3. EDCI/HOBT/DMF/DCM; 4.Hydrazine/acetonitrile/water (5:90:5); 5. Cypate/HOBT/DIC/DMF; 6. TFA/water(95:5).

UV-Vis and Emission Spectra

Absorbance spectra were measured on a Beckman Coulter DU 640 UV-Visible spectrophotometer. Fluorescence spectra were recorded on a HORIBA Jobin Yvon Fluorolog-3 fluorometer. Stock solutions (1.0 mM) of the conjugates were prepared by dissolving each sample in 80% aqueous DMSO. UV-Vis and fluorescence measurements were carried out by adding 5.0 μL of the stock solutions via a micropipette into 3 mL of 20% aqueous DMSO in a quartz cuvette.

Figure 12A:
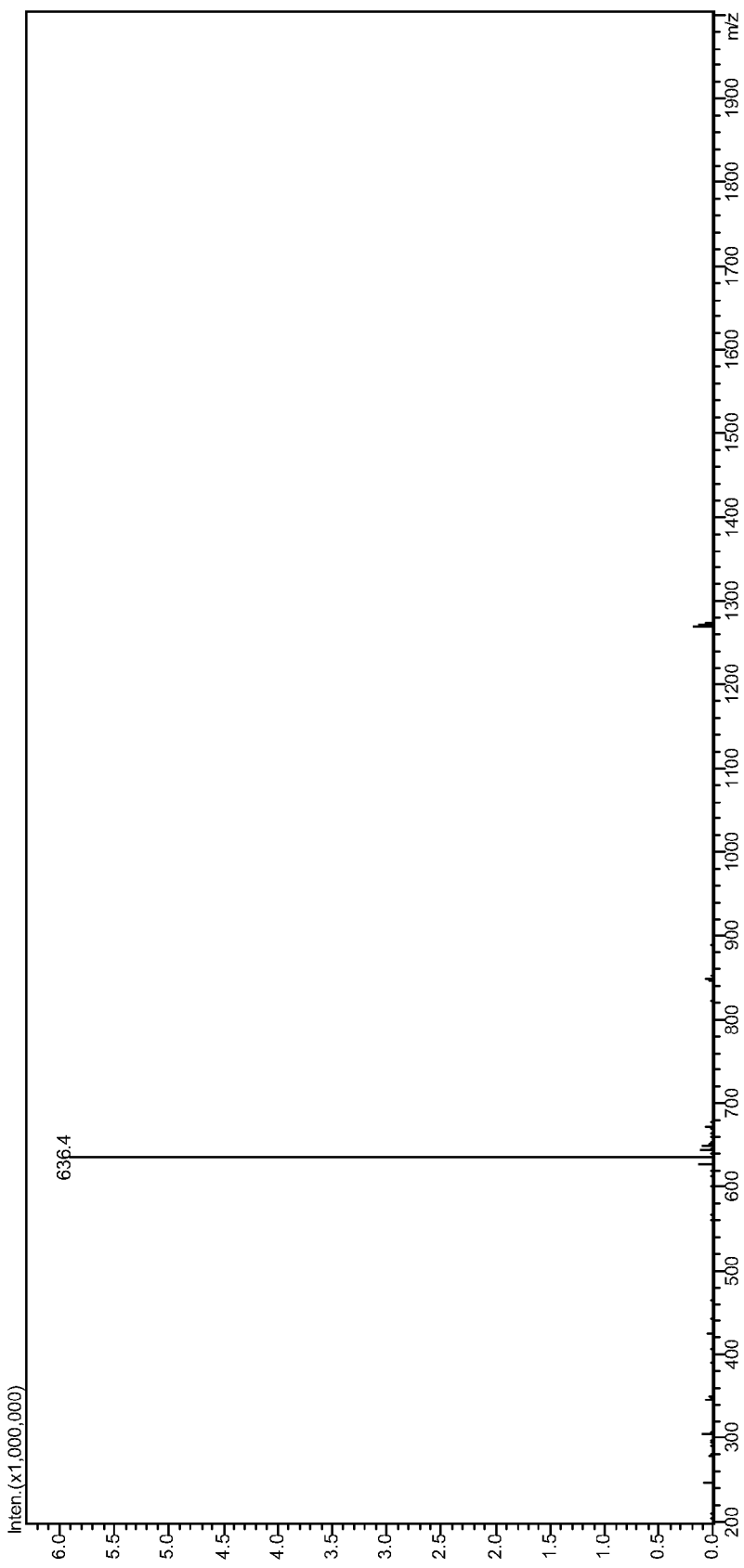
FIG. 12 illustrates the spectral properties of a typical cyclic cypate-RGD conjugate. (Left) ES-MS spectra and (right) normalized UV-Vis and emission spectra of cypate-cyclo[CRGDDC] [SEQ ID NO:2].
Figure 12B:
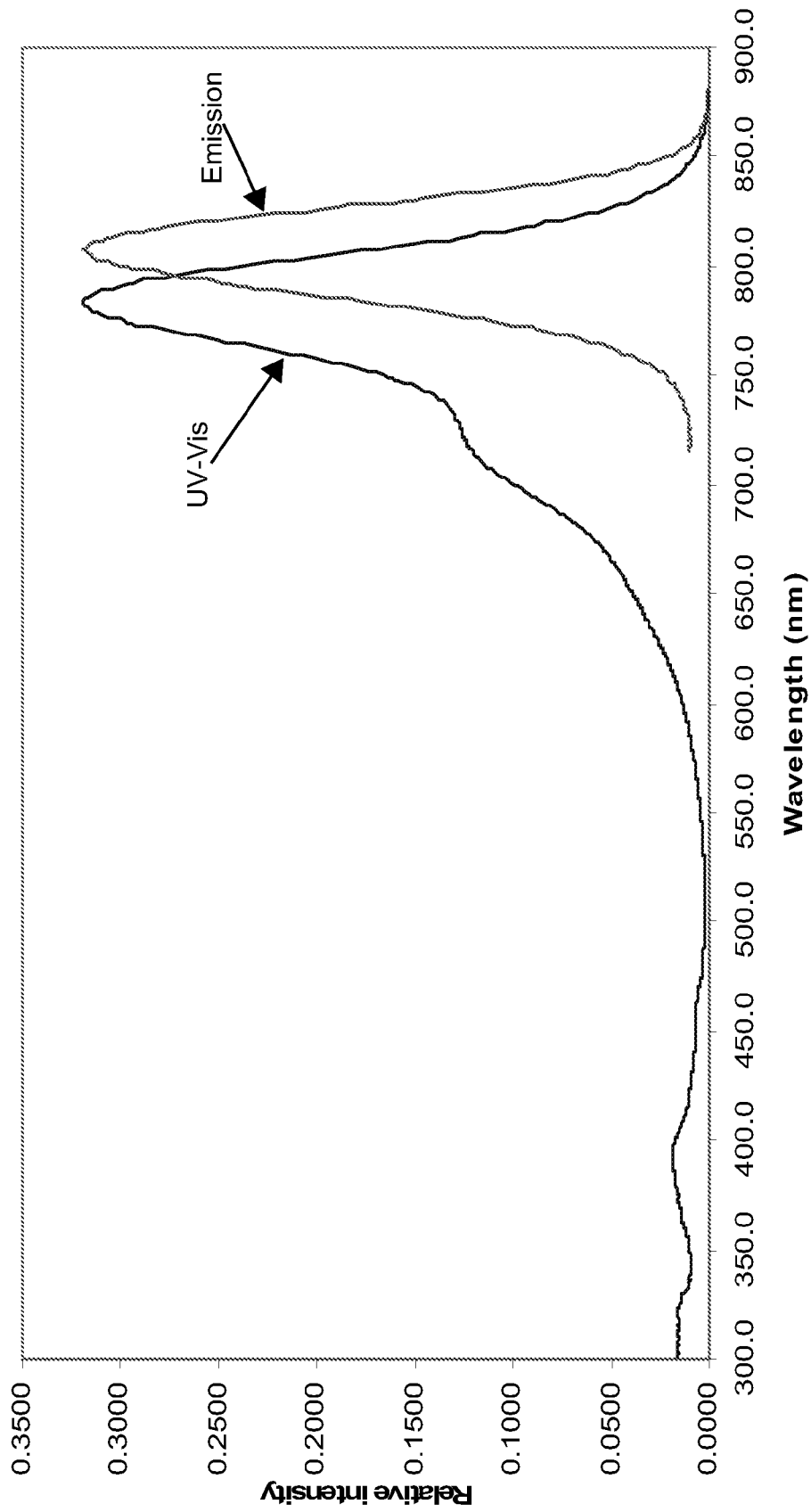

All the Cypate-RGD conjugates displayed UV-vis and emission spectra (783 nm and 808 nm) similar to that shown in FIG. 12.

TABLE 2

List of some cyclic RGD peptides and their $\alpha_v\beta_3$ integrin binding affinities.

| SEQ ID NO | Structure | $IC_{50}$ |
|---|---|---|
| 1 | Cyclo(RGDfV) | $3.25 \times 10^{-7}$ |
| 7 | Cyclo($K^{(Cypate)}$RGDfV) | $7.948 \times 10^{-5}$ |
| 19 | Cypate-cyclo(CRGDC)-NH$_2$ | $4.6 \times 10^{-6}$ |
| 20 | Cypate-cyclo(CRGDSC)-NH$_2$ | $1.14 \times 10^{-6}$ |
| 21 | Cypate-cyclo(CRGDGRC)-NH$_2$ | $1.087 \times 10^{-6}$ |
| 3 | Cypate-cyclo(CRGDLC)-NH$_2$ | $9.64 \times 10^{-6}$ |
| 2 | Cypate-cyclo(CRGDDC)-NH$_2$ | $1.89 \times 10^{-6}$ |

$\alpha_v\beta_3$ Integrin Binding

The binding affinities were measured based on the competitive binding between purified $\alpha_v\beta_3$ integrin (ABI) and peptide ligands. Echistatin is a polypeptide that binds irreversibly with high affinity and specificity to ABI. $^{125}$I-echistatin was used as a tracer in ABI binding assays. Commercially available cyclic RGD pentapeptide, i.e, cyclo (RGDfV) [SEQ ID NO:1] was used as a reference standard because it is known to bind $\alpha_v\beta_3$ integrin with high affinity.

Receptor binding assays were performed by using purified human $\alpha_v\beta_3$ integrin protein from Chemicon International, Inc. (Temecula, Calif.). Assays were carried out using the Millipore Duropore membrane 96-well plates and the Millipore MultiScreen system (Bedford, Mass.). The 96-well membrane plate was blocked with 0.1% Polyethylenimine blocking solution overnight at 4° C. $^{125}$I-echistatin (50 nmol/L) was added to the binding buffer (50 mM Tris-HCl, pH 7.4, 100 mM NaCl, 2 mM CaCl$_2$, 1 mM MgCl$_2$, 1 mM MnCl$_2$, 1% BSA) containing integrin protein (50 ng per well in 96-well membrane plate) and ligands in a total volume of 200 μL per well. The concentration range of ligand was between 0.01 μM and 100 μM. The mixtures were incubated for 2 h at room temperature, the ABI was then filtered by centrifugation at 1500 g and washed three times with 0.20 mL of ice-cold binding buffer. The filters containing radioactivity bound ABI were removed using a punch apparatus and counted using a Packard Cobra II Auto-gamma counter (Meriden, Conn.). Nonspecific binding of $^{125}$I-echistatin was determined to be 5 to 10% of total binding. The 50% inhibitory concentrations ($IC_{50}$) were calculated by nonlinear regression analysis by use of the GraphPad Prism 4 computer fitting program (GraphPad Software, Inc., San Diego, Calif.). Radiolabeling of $^{125}$I-echistatin (Amersham Biosciences, Piscataway, N.J.) was carried out in a mixture of 0.25% BSA, 5.0% lactose, 0.21% citric acid and aprotinin (0.9 TIU/ml). The specific activity of radiolabeled peptide was ~2000 Ci/mmol. Radiochemical purity (90%) was determined by reverse phase HPLC.

Table 2 presents the $IC_{50}$ values of the various cyclic peptides. Both the control cyclo(RGDfV) [SEQ ID NO:1] and its cypate-labeled analog, i.e., Cyclo-[$K^{(Cypate)}$RGDf] [SEQ ID No:4], had similar binding affinities. This indicated the substitution of valine with lysine residue and the cypate-labeling retained the binding affinity. Nevertheless, the insertion of lysine and cypate conjugation decreased greatly the binding affinity as indicated by Cyclo-[$K^{(Cypate)}$RGDfV] [SEQ ID NO:7]. This reflected the proportion change of bioactive conformations from the cyclic pentapeptides to cyclic hexapeptide. Table 3 presents the $IC_{50}$ values (and $R^2$ values) of additional peptide conjugates.

TABLE 3

Properties of additional linear or cyclic RDG and GRD peptides.

| SEQ ID NO: | Structure | $IC_{50}$ (M) | $R^2$ |
|---|---|---|---|
| 24 | Cyclo(DPhe-Val-Lys-Arg-Gly-Asp)-OH | $1.89 \times 10^{-6}$ | 0.996 |
| 25 | Cyclo(Arg-Gly-Asp-DPhe-Asp)-Lys-NH$_2$ | $1.74 \times 10^{-6}$ | 0.982 |
| 26 | Cyclo(Arg-Gly-Asp-DPhe-Asp)-EAhx-Lys-OH | $1.94 \times 10^{-6}$ | 0.9839 |
| 5 | Cypate-Gly-Arg-Gly-Asp-Ser-Pro-Lys-OH | $3.277 \times 10^{-7}$ | 0.9769 |
| 27 | Cypate-Lys-Arg-Gly-Asp-DPhe-EAhx-NH$_2$ | $3.02 \times 10^{-6}$ | 0.9947 |
| 28 | Cypate-Lys-Arg-Gly-Asp-DPhe-Asp-DPhe-EAhx-NH$_2$ | $3.277 \times 10^{-7}$ | 0.9769 |
| 29 | Cypate-DPhe-Cyclo(Cys-Tyr-DTrp-Lys-Thr-Cys)-Thr-Val-Arg-Gly-Asp-NH$_2$ | $4.42 \times 10^{-6}$ | 0.997 |
| 30 | H-DPhe-Val-Arg-Gly-Asp-OH | $5.14 \times 10^{-6}$ | 0.9977 |
| 6 | Cypate-Gly-Arg-Asp-Ser-Pro-Lys-OH | $7.016 \times 10^{-6}$ | |
| 31 | Cypate-BAla-Arg-Gly-Asp-EAhx-Arg-Gly-Asp-EAhx-Arg-Gly-Asp-Ser-Pro-Lys-OH | $6.557 \times 10^{-8}$ | 0.9954 |
| 32 | H-His-Asp-Arg-Gly-Asp-Cys-Phe-Lys-OH | $4.114 \times 10^{-7}$ | 0.9906 |

TABLE 3-continued

Properties of additional linear or cyclic RDG and GRD peptides.

| SEQ ID NO: | Structure | IC$_{50}$ (M) | R$^2$ |
|---|---|---|---|
| 33 | H-B-Ala-Asp-Cys-Arg-Gly-Asp-Cys(Et)-Phe-Val-OH | $3.287 \times 10^{-7}$ | 0.978 |
| 34 | DTPA-His-Asp-Cys(Et)-Arg-Gly-Asp-Cys(Et)-Phe-Lys-OH | $7.124 \times 10^{-7}$ | 0.9944 |
| 35 | Cyclo(DPhe-Val-Arg-Gly-Asp)-OH | $1.061 \times 10^{-8}$ | 0.9944 |
| 36 | DTPA-Val-Arg-Gly-Asp-DPhe-Cyclo(Cys-Tyr-DTrp-Lys-Thr-Cys)-Thr-NH$_2$ | $5.837 \times 10^{-7}$ | 0.9742 |
| 37 | DTPA-DPhe-Cyclo(Cys-Tyr-DTrp-Lys-Thr-Cys)-Thr-Val-Arg-Gly-Asp-NH$_2$ | $1.113 \times 10^{-6}$ | 0.9776 |
| 38 | DTPA-DPhe-Cyclo(Cys-Tyr-DTrp-Lys-Thr-Cys)-Thr-Val-Arg-Gly-Asp-DPhe-NH$_2$ | $9.453 \times 10^{-7}$ | 0.9745 |
| 39 | H-DPhe-Cyclo(Cys-Tyr-DTrp-Lys-Thr-Cys)-Thr-Val-Arg-Gly-Asp-NH$_2$ | $7.221 \times 10^{-7}$ | 0.9422 |
| 40 | H-DPhe-Cyclo(Cys-Tyr-DTrp-Lys-Thr-Cys)-Thr-Val-Arg-Gly-Asp-DPhe-NH$_2$ | $3.567 \times 10^{-7}$ | 0.9738 |
| 41 | H-Val-Arg-Gly-Asp-DPhe-Cyclo(Cys-Tyr-DTrp-Lys-Thr-Cys)-Thr-NH$_2$ | $1.676 \times 10^{-6}$ | 0.9971 |
| 42 | DTPA-Gly-Arg-Asp-Ser-Pro-Lys-OH | $8.492 \times 10^{-7}$ | 0.9893 |
| 43 | DTPA-Gly-Arg-Gly-Asp-Ser-Pro-Lys-OH | $3.533 \times 10^{-7}$ | 0.9987 |
| 44 | DOTA-Arg-Gly-Asp-Ser-Pro-Lys-OH | $6.942 \times 10^{-7}$ | 0.9732 |
| 45 | DOTA-Arg-Gly-Asp-Ser-Pro-Lys(Cypate)-NH$_2$ | $7.221 \times 10^{-7}$ | 0.9422 |
| 46 | H-Arg-Gly-Asp-Ser-Pro-Lys(Cypate)-NH$_2$ | $1.00 \times 10^{-6}$ | 0.9895 |
| 47 | Cypate-BAla-Cyclo(Cys-Arg-Gly-Asp-Cys)-DPhe-Val-NH$_2$ | $9.767 \times 10^{-10}$ | 0.945 |
| 7 | Cyclo(Lys(Cypate)-Arg-Gly-Asp-DPhe-Val) | $7.948 \times 10^{-5}$ | 0.9076 |
| 19 | Cypate-Cyclo(Cys-Arg-Gly-Asp-Cys)-NH$_2$ | $8.112 \times 10^{-10}$ | 0.914 |
|  |  | $4.6 \times 10^{-6}$ | 0.9904 |
| 48 | Cypate(Arg-Gly-Asp-Ser-NH$_2$)1-(D-Glucosamine) | $1.937 \times 10^{-6}$ | 0.8823 |
| 49 | Cypate-[Cyclo(Cys-Arg-Gly-Asp-Ser-Cys)-NH$_2$]1-(D-Glucosamine) | $2.751 \times 10^{-7}$ | 0.9808 |
| 20 | Cypate-[Cyclo-(Cys-Arg-Gly-Asp-Ser-Cys)]1 | $1.574 \times 10^{-9}$ | 0.9315 |
|  |  | $1.14 \times 10^{-6}$ | 0.9997 |
| 50 | Cypate(Octreotate)1-(Arg-Gly-Asp-NH$_2$)1 | $4.67 \times 10^{-6}$ | 0.9948 |
| 51 | Cypate-Val-Arg-Gly-Asp-DPhe-Cyclo(Cys-Tyr-DTrp-Lys-Thr-Cys)-Thr-OH | $3.25 \times 10^{-4}$ | 0.987 |
| 52 | Cypate(3)-Gly-Arg-Asp-Ser-Pro-Lys-OH | $2.673 \times 10^{-3}$ | 0.9856 |
| 53 | Cypate(2)-Gly-Arg-Asp-Ser-Pro-Lys-OH | $2.66 \times 10^{-4}$ | 0.9914 |
| 15 | DOTA-Gly-Arg-Asp-Ser-Pro-Lys-OH | $3.50 \times 10^{-4}$ | 0.9852 |

BAla = beta alanine; Cys(Et) - Ethyl cysteine; Dphe = D-phenylalanine; DTrp = D-tryptophan; EAhx = 6-aminohexanoic acid; and H refers to a free amino group at the N-terminal.

Cellular Internalization

A549 and A427 cells were purchased from ATCC and grown in 75 cm tissue culture flasks or on Lab-Tek chambered slides in Ham's F12K medium with 2 mM L-glutamine supplemented with 1.5 g/L sodium bicarbonate, 10% fetal calf serum, 100 units/ml penicillin and 100 units/mL streptomycin.

Cells were grown to confluence on LabTek microscope slides. After washing with PBS, the cells were incubated with 1 μM of the target compounds for 1 h at 37° C. The medium was removed and the cells washed with PBS. The slides were mounted with anti-fading mounting medium. Cells were visualized with an Olympus microscope system (FV 1000) using 755 excitation and 845 nm emission filters.

Figure 13:
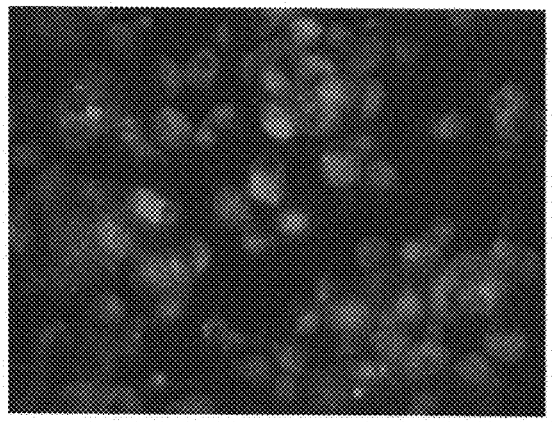
FIG. 13 illustrates the internalization of cypate-cyclic RGD compounds. (a) Uptake of cypate-cyclo[CRGDLC] [SEQ ID NO:3] in A427 cells. (b) Uptake of cypate-cyclo [CRGDLC] [SEQ ID NO:3] in A549 cells. (c) Uptake of cyclo-[K$^{(cypate)}$RGDf] [SEQ ID NO:4] in A549 cells. (d) Uptake of cypate alone.
Figure 13:
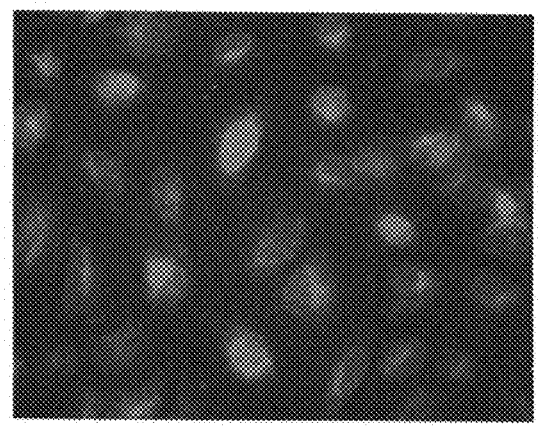
Figure 13:
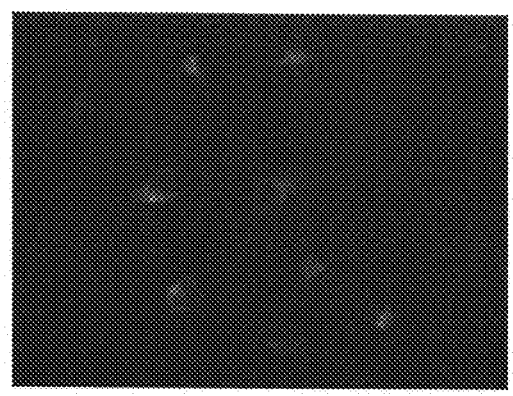
Figure 13:
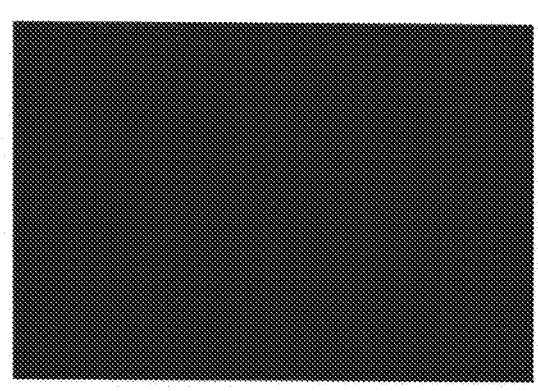

The cyclic cypate-RGD conjugates were internalized into the cells. Although the leucine-containing compound Cypate-cyclo(CRGDLC)—NH$_2$ [SEQ ID NO:3] did not have the highest receptor binding affinity, it was internalized by the cells much better than some of the other compounds (FIG. 13a-c). These data suggest that, besides the receptor binding affinities, other structural features of the molecules, such as lipophilicity, may be important in the cellular internalization.

Example 3

Targeting β$_3$ Integrin Protein with Fluorescent Labeled Linear GRD Peptides

Integrins are a large family of heterodimeric transmembrane proteins that mediate cell-cell and cell-matrix interactions. They play key roles in tumor invasion, formation of metastasis, and tumor-induced angiogenesis. These proteins associate as αβ heterodimers in their native environments, where the α and β subunits perform distinct but complementary physiological functions. Currently, eighteen α subunits and eight β subunits have been identified, with each β subunit associating with different α subunit. The β$_3$ subunit has been shown to form α$_{IIb}$β$_3$ and α$_v$β$_3$ heterodimers. Because of its overexpression in many pathophysiological processes, anti-angiogenic drugs and tumor imaging agents have been developed to target α$_v$β$_3$ integrin (ABI). The β$_3$ integrin has been associated with a number of cancers, including prostate, breast and stomach, as well as melanomas. However, only a limited number of studies have targeted the β$_3$ integrin for diagnostic and therapeutic interventions due to limitations in the availability of β$_3$-specific synthetic compounds.

Biomolecules and synthetic compounds containing the arginine-glycine-aspartic acid (RGD) peptide sequence are known to bind ABI and related integrin heterodimers with high affinity. In a recent study, it was demonstrated that removal of glycine in the linear RGD peptide sequence and labeling the resulting GRD peptide with a near infrared fluorescent dye (cypate) formed an imaging agent that was specifically retained ABI-positive A549 tumor cells and tissue (Achilefu et al. (2005) Proc. Natl. Acad. Sci. USA 102:7976-7981). In this study, evidence is provided that cellular internalization and tumor uptake of cypate-GRD peptide conjugate by ABI-positive tumor cells is mediated by the initial association of the probe with the β$_3$ integrin subunit. These results show that cypate-GRD could be used to image the expression of this protein in cancers. Because of the ease of preparing and labeling the linear GRD peptides, conjugation of cytotoxic drugs to the peptide could be a useful strategy for treating a variety of cancerous tissues.

Peptide Synthesis

All reagents and solvents were obtained from commercial sources and used without further purification. Amino acids were purchased from Novabiochem (San Diego, Calif.). The ABI-avid peptide (cyclo[RGDfV]; SEQ ID NO:1) was used for the blocking studies. The NIR fluorescent dye, cypate, was prepared as described above. The cypate-GRD peptide, cypate-(GRDSPK) [SEQ ID NO:6], the linear cypate-RGD peptide, cypate-(GRGDSPK [SEQ ID NO:5], and the cyclic cypate-RGD peptide, cyclo-[K$^{(Cypate)}$RGDfV] [SEQ ID NO 7] were synthesized as described above in Examples 1 and 2. The peptides were purified and analyzed as described above.

Western Blotting

The human nonsmall cell carcinoma cell line A549 and the human erythroblast cell line HEL were purchased from ATTC. A549 cells were grown, as described above. HEL cells were maintained in RPMI 1640 with 2 mM L-glutamine adjusted to contain 1.5 g/L sodium bicarbonate, 4.5 g/L glucose, 10 mM HEPES, and 1.0 mM sodium pyruvate. A549 and HEL cells were harvested and lysed in CHAPS buffer (50 mM Pipes/HCl, pH 6.5, 5 mM dithiothreitol (DTT), 2 mM EDTA, 0.1% CHAPS, 20 μg mL$^1$ leupeptin, 10 μg mL$^1$ pepstatin, 10 μg mL$^1$ aprotinin, 1 mM phenyl methylsulfonyl fluoride). Cells were homogenized with an ultrasonic processor, and lysis was confirmed by microscopy. Total cell lysates were clarified by centrifugation. Protein concentration of the lysates was determined using the Bio-Rad protein assay reagent. SDS-PAGE was performed using the EC120 Mini vertical gel system (Thermo EC, Holbrook, N.Y.). Electrophoresed samples were transferred onto PVDF membrane using an EC140 Mini Blot Module (Thermo EC, Holbrook, N.Y.) apparatus. The membranes were blocked 1 h at room temperature in PBS containing 5% nonfat dry milk (w/v) and 0.1% (v/v) Tween-20 (PBS-T) after which they were incubated overnight in PBS-T containing 3% nonfat dry milk (w/v) and 1:1000 dilution of anti-β$_3$, anti-α$_v$, or anti-α$_{IIb}$β$_3$ antibodies. After washing three times for 10 min each in PBS-T, membranes were incubated for 1 h with diluted polyclonal rabbit antigoat IgG conjugated to horseradish peroxidase in PBS-T containing 3% nonfat dry milk (w/v). Membranes were again washed three times for 10 min each in PBS-T and developed using the chemiluminescence ECL kit (Pierce) according to the manufacturer's instruction.

Western blot confirmed that α$_{IIb}$β$_3$ was present in the A549 cells. Both α$_v$ and β$_3$ were expressed in the cell line (FIGS. 2a and b), as was shown above. Previous studies have shown that β$_3$ protein dimerizes with either α$_v$ or α$_{IIb}$ integrins. Using HEL cells as a positive control, this experiment confirmed that A549 cells also expressed α$_{IIb}$β$_3$ (FIG. 2c).

Receptor Binding

A 96-well filtration plate was blocked with 0.1% polyethylenimine blocking solution by incubation overnight at 4° C. $^{125}$I-Echistatin (50 nmol/L) was added to the binding buffer (50 mM Tris-HCl, pH 7.4, 100 mM NaCl, 2 mM CaCl$_2$, 1 mM MgCl$_2$, 1 mM MnCl$_2$, 0.1% BSA) with integrin α$_v$β$_3$ protein (50 ng/well in 96-well filtration plate) and ligands. The concentration range of ligand was between 0.01 and 100 μM. The mixture was incubated for 2 h by shaking at room temperature. Each well was washed three times with 0.25 mL of ice-cold binding buffer and dried. The filters were removed using a punch apparatus and counted in a gamma counter.

The receptor binding affinities of the peptide conjugates were evaluated by using purified ABI proteins, $^{125}$I-echistatin, and cyclo[RGDfV] [SEQ ID NO:1] as the target receptor, tracer, and reference standard, respectively. Echistatin is a polypeptide that binds purified ABI specifically and irreversibly and the radiolabeled analogue is used widely in ABI binding assays. All of the RGD compounds were recognized by ABI, with the exception of Cyp-GRD, which had IC$_{50}$ of >100 μM (Table 4). The highest binding affinity (IC$_{50}$ ca. 0.11

μM) was found for the RGD peptide, cyclo[RGDfV] [SEQ ID NO:1], which is in agreement with the literature data (IC$_{50}$ ca. 0.5 μM). Because of the rearrangement of the RGD peptide sequence, the low binding of cypate-GRD peptide to ABI was expected. Considering that in vivo studies showed enhanced retention of cypate-GRD peptide in A549 tumor tissue despite its low affinity for the heterodimeric ABI proteins, the binding assay was also performed using A549 cell membranes. No improvement in the ABI binding affinity was observed by this method, however.

TABLE 4

Binding Affinities of Peptides.

| SEQ ID NO: | Structure | IC$_{50}$ ± SD (μM) |
|---|---|---|
| 6 | Cypate-GRDSPK-OH | >100 |
| 5 | Cypate-GRGDSPK-OH | 10.66 ± 1.87 |
| 7 | cyclo[RGDfVK$^{(cypate)}$] | 79.09 ± 3.03 |
| 1 | cyclo[RGDfV] | 0.113 ± 0.008 |
| 54 | cyclo[RGDfVK] | 1.926 ± 0.347 |

Cell Uptake and Internalization of the Cypate-Peptide Conjugates

The ABI-positive cells were incubated with cypate or cypate-peptide conjugates at 37° C. for different time points. A549 cells were grown as detailed above. The human glioblastoma cell line, U87, and the human embryonic kidney cell line, HEK, were purchased from ATTC. U87 and HEK cells were maintained in minimum essential medium (MEM) with 2 mM L-glutamine and Earle's BSS adjusted to contain 1.5 g/L sodium bicarbonate, 0.1 mM nonessential amino acids, and 1.0 mM sodium pyruvate, with 10% fetal calf serum, 100 units/mL penicillin, and 100 units/mL streptomycin. Cells were grown on Lab-Tek slides. The medium was replaced and cells were incubated for various times up to 4 h at 37° C. in the presence of 1 μM of the dye conjugated peptides. For fluorescence microscopy, cells were visualized with an Olympus BX61W1 microscope using 775/50 excitation, 845/55 emission. For subcellular localization studies, 25 nM mitotracker green or 50 nM lysotracker red from Molecular Probes (Eugene, Oreg.) was added during the last 15 min or 60 min of incubation, respectively. For antibody blocking studies, cells were pretreated with 10 μg/ml functional blocking anti-α or anti-β antibodies from Molecular Probes for 15 min at 37° C. and then incubated with the cypate compound for 30 min at 37° C. For RGD peptide blocking studies, cells were pretreated with cyclo[RGDfV] [SEQ ID NO:1] for 15 min at 37° C. and then incubated with the cypate conjugate for 30 min at 37° C. Relative fluorescence was determined for five different areas of each experimental condition using the Slidebook software, and the results were averaged. The average relative fluorescence for each condition was normalized to cells treated with Cyp-GRD peptide.

Figure 14:
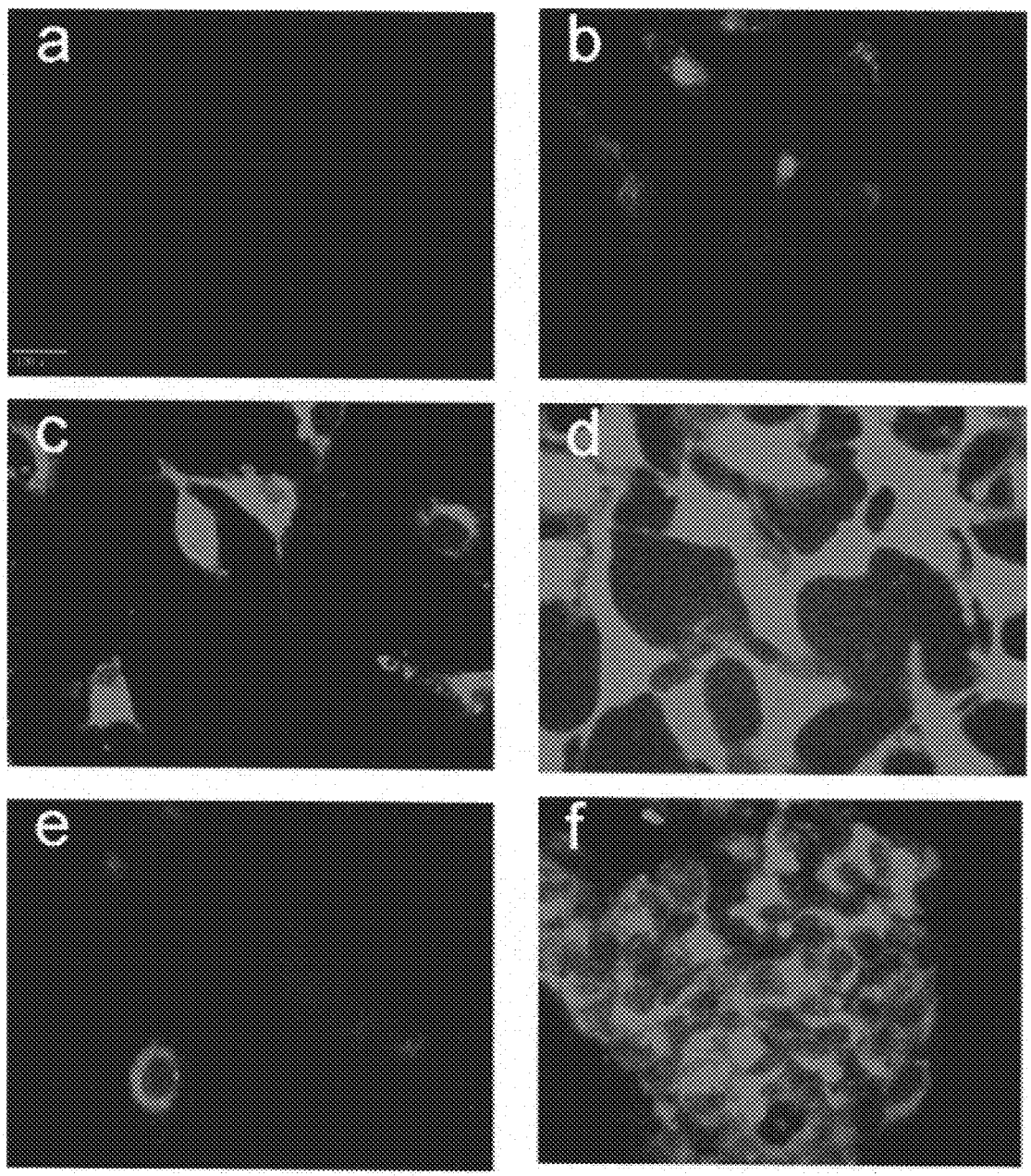
FIG. 14 presents the internalization of various compounds in ABI-positive A549, U87, and HEK cells at 37° C. A549 cells were treated with 1 μM of (a) cypate, (b) cypate-GRD, (c) cypate-RGD, and (d) cyclic cypate-RGD for 4 h. (e) U87 and (f) HEK cells were incubated with cypate-GRD for 1 h.

High accumulation was observed for the compounds at 4 h postincubation relative to earlier time points. All fluorescence intensities were normalized to that of cypate dye as background (FIG. 14a). As was expected, all of the bioconjugates internalized in the cells. However, no clear correlation between the binding affinities of the compounds to ABI and their fluorescence intensities in cells was observed. On one hand, the linear RGD compound [SEQ ID NO:5] with higher affinity showed higher intensity than the linear GRD compound [SEQ ID NO:6] with low affinity (compare FIGS. 14b and c). On the other hand, the cyclic RGD [SEQ ID NO:7] (FIG. 14d) showed much higher fluorescence intensity than the linear RGD compound (FIG. 14c), although the ABI binding affinities of both compounds to ABI were comparable (Table 4). Additional testing of the cypate-GRD compound in other ABI-positive cells (U87, HEK) also showed internalization of the compound within an hour of incubation (FIGS. 14e and f). The uptake of cypate-GRD in these cells was not anticipated based on its low ABI binding affinity. Most importantly, co-incubation of cypate-GRD with the ABI-avid peptide cyclo[RGDfV] [SEQ ID NO:1] blocked the uptake of cypate-GRD (see FIG. 15b), suggesting the recognition of the bioconjugates by the same receptor protein.

Figure 15:
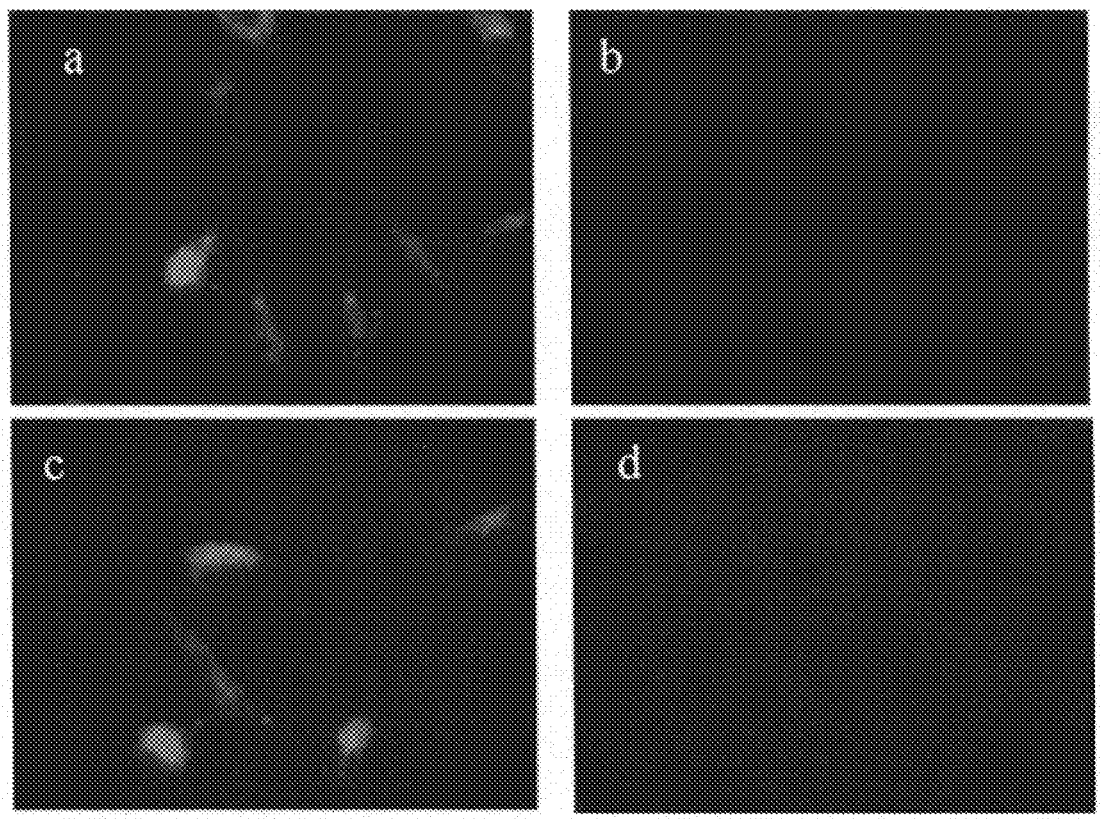
FIG. 15 illustrates the blocking of cypate-GRD internalization in A549 cells. (a) Cells were incubated with cypate-GRD. (b) Cells were preincubated for 15 min with inhibitory cyclic RGD peptide and then incubated with cypate-GRD. (c) Cells were preincubated for 30 min with anti-$\alpha_v$ antibodies and then with cypate-GRD. (d) Cells were preincubated for 30 min with anti-$\beta_3$ antibodies and then with cypate-GRD.

To assess the roles of different integrins in the cellular internalization of cypate-GRD in ABI-positive cells, antibody blocking studies were performed. As shown in FIG. 15c, blocking of α$_v$ integrin by the specific antibody did not inhibit the internalization of cypate-GRD. It was also found that, with the exception of anti-β$_3$ integrin antibody (FIG. 15d), all of the other anti-β integrin antibodies tested were not effective in inhibiting the uptake of cypate-GRD by A549 cells. The successful blocking of cellular internalization of this compound by the anti-β$_3$ integrin antibody (FIG. 15) suggests that cypate-GRD binds to β$_3$ integrin and that this interaction may mediate the observed internalization.

Immunostaining for α$_v$, α$_{IIB}$, β$_3$, and the Heterodimers in Cells Treated with Cypate-GRD To confirm the receptors that mediate internalization of cypate-GRD in A549 cells, the levels of α$_v$, α$_{IIb}$, β$_3$, α$_v$β$_3$, and α$_{IIB}$β$_3$ in treated and untreated cells were assessed by immunostaining. Cells were grown on Lab-Tek slides and fixed in 3% paraformaldehyde in PBS for 30 min. After washing three times for 5 min each in PBS, the cells were blocked to mask nonspecific binding sites with PBS containing 1% normal goat serum (blocking solution) for 1 h. Primary antibodies of mouse anti-human α$_v$ or β$_3$ integrin antibodies (Chemicon International, Temecula, Calif.) or antihuman α$_{IIB}$β$_3$ (GeneTex, Inc., South Bend, Ind.) diluted 1:500 (v/v) in blocking solution were added to each well and incubated overnight at 4° C. After washing three times for 10 min each in PBS, cells were incubated for 1 h with diluted biotinylated-anti-mouse IgG antibody in blocking solution. After washing, antigens were detected with avidin-horseradish peroxidase conjugate and diamino benzidine (Vector Laboratories, Burlingame, Calif.). Slides were counterstained with Mayers Hematoxylin, and the cover slips were mounted for microscopic examination.

Figure 16:
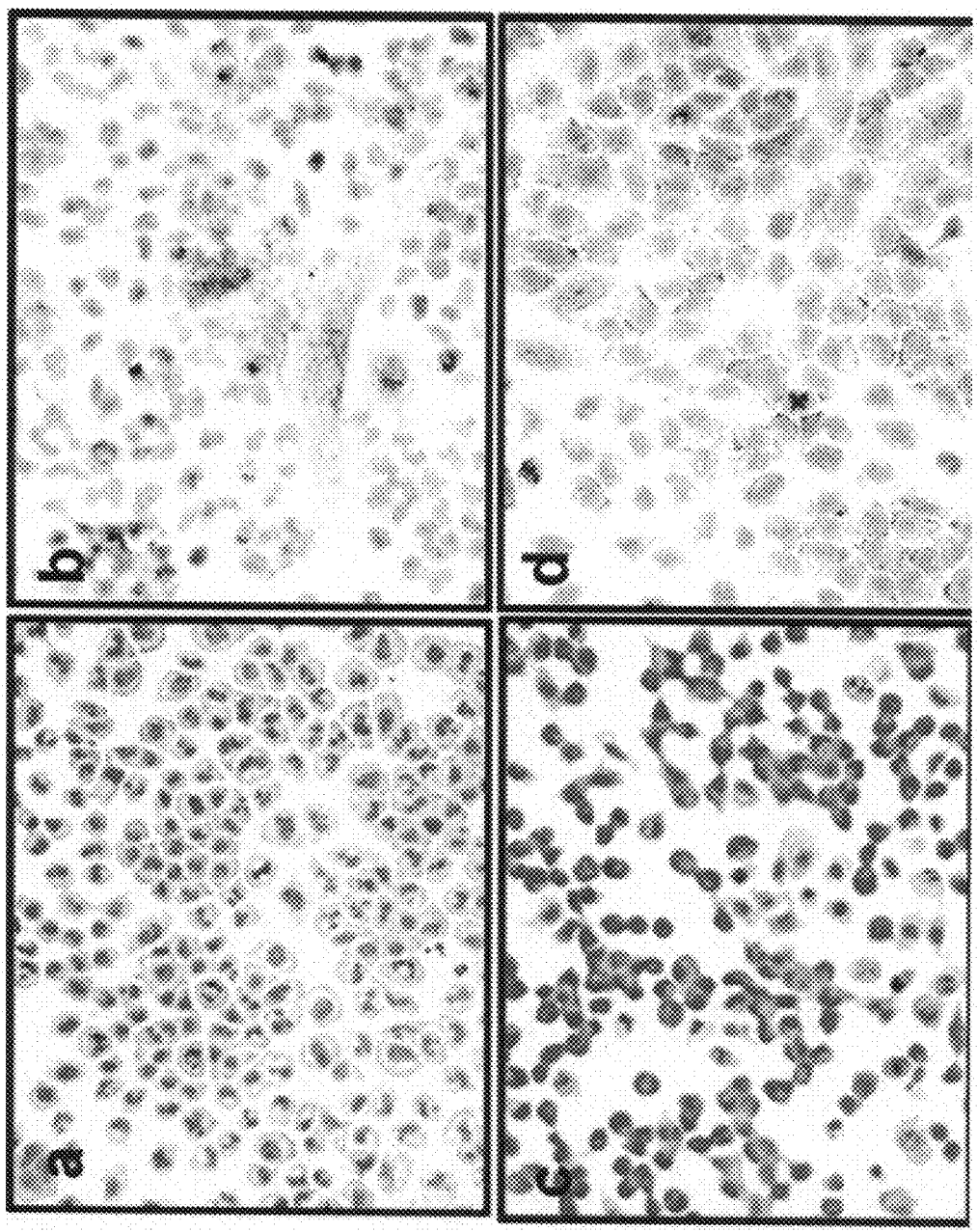
FIG. 16 presents immunostaining of $\alpha_v$ (a and b), $\beta_3$ (c and d), $\alpha_{IIb}\beta_3$ (e and f), and $\alpha_v\beta_3$ (g and h) protein expression in A549 cells. Cells were treated with 100 μM of cypate-RGD (a, c, e, and g) or PBS (b, d, f, and h). Anti-$\alpha_v$, anti-$\beta_3$, anti-$\alpha_{IIb}\beta_3$, and anti-$\alpha_v\beta_3$ integrin antibodies were used to identify the respective proteins.
Figure 16:
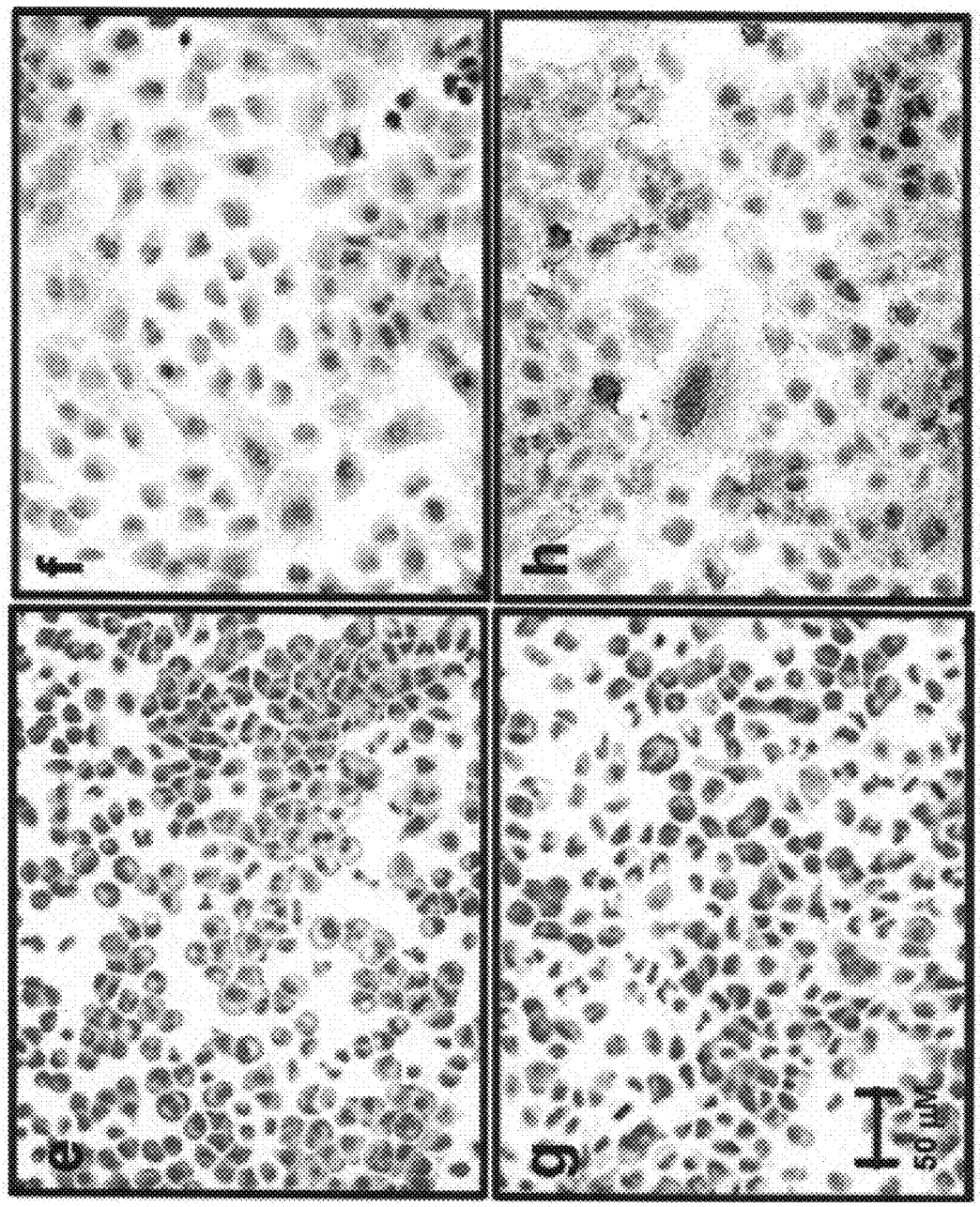

FIG. 16 shows that all of the antibodies stained untreated A549 cells. Relative to the PBS-treated cells, preincubation in buffer containing cypate-GRD resulted in reduced staining of A549 cells with the anti-α$_v$, anti-β$_3$, anti-α$_v$β$_3$, and anti-α$_{IIB}$β$_3$ antibodies.

Internalization of Cypate-Peptide Conjugates in Integrin β$_3$ Knock-Out Cells

Having shown that cypate-GRD preferentially binds to β$_3$ integrin in ABI-positive cells, it was hypothesized that it would not internalize in β$_3$ knockout cells. Vascular smooth muscle cells (VSMCs) from the aortas of β$_3^{-/-}$apoE$^{-/-}$ and β$_3^{+/+}$apoE$^{-/-}$ mice were provided by Dr. Clay F. Semenkovich (Washington University Medical School in St. Louis, Mo.). VSMCs were maintained at 37° C. in humidified atmosphere containing 5% CO$_2$ in Dulbecco's modified Eagle's medium (DMEM) containing 10% fetal bovine serum, 4 mmol/L L-glutamine, 1 mM sodium pyruvate, 100 U/ml penicillin, 0.25 μg/ml amphotericin, 100 μg/ml streptomycin. The internalization of cypate-GRD and cyclic cypate-RGD were compared in $\beta_3$ knockout and wild-type VSMC cells, essentially as described above.

Figure 17:
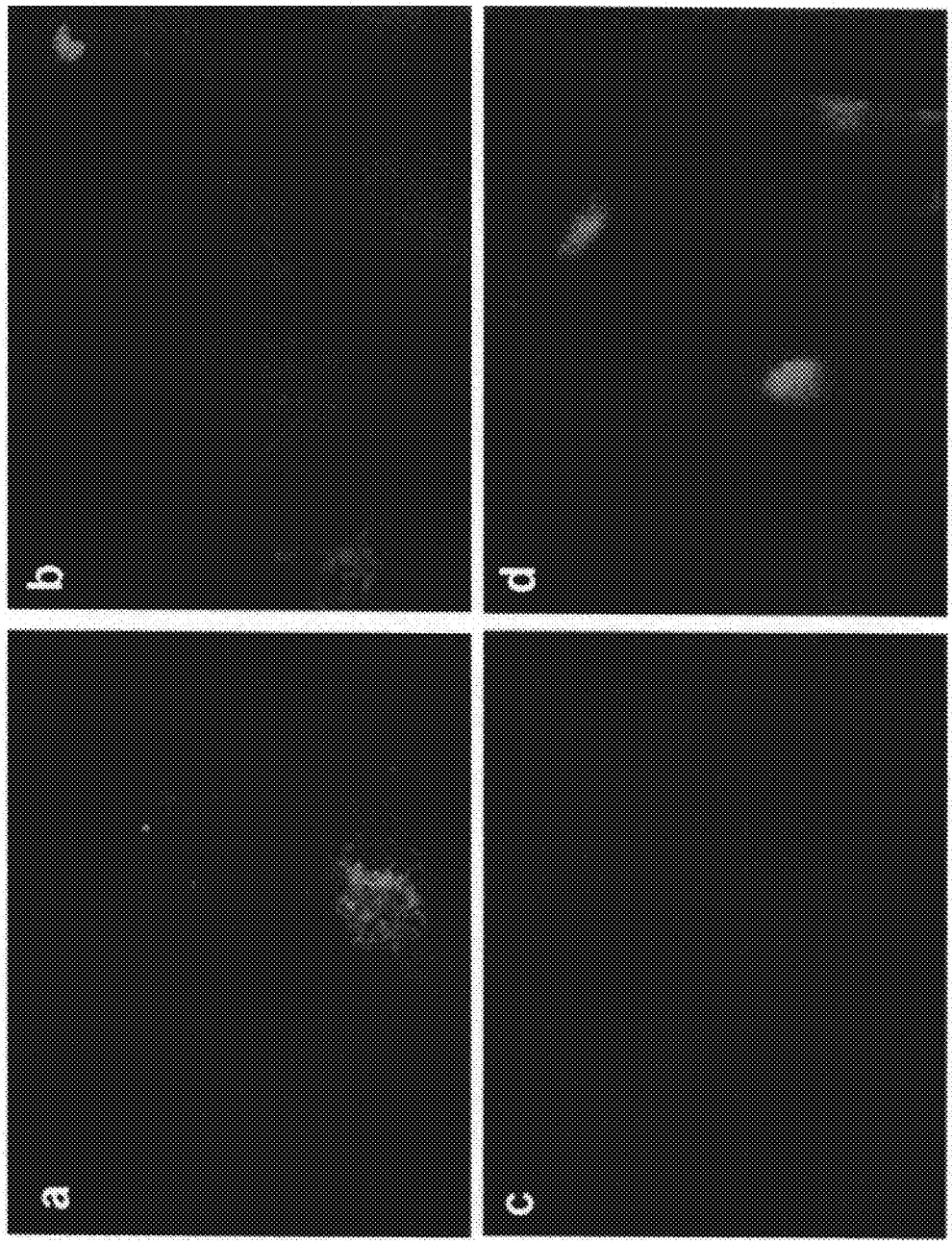
FIG. 17 illustrates the cellular uptake of cypate-peptide compounds into $\beta_3$ knock-out cells. Vascular smooth muscle cells (VSMC) of integrin $\beta_3$ knock-out (a and c) and wild-type (b and d) mice were treated with 1 μM of cyclic cypate-RGD (a and b) and cypate-GRD (c and d) for 1 hr at 37° C.

Expectedly, both compounds internalized in VSMC wild-type cells (FIGS. 17b and d), but the internalization of cypate-GRD was not observed in the $\beta_3$ knockout cells (FIG. 17c). The fluorescence observed in FIG. 17a was attributed to the binding of cyclic cypate-RGD with the $\alpha_v$ subunit. These findings further confirm that $\beta_3$ integrin actively mediated the cellular internalization of cypate-GRD.

Cytotoxicity and Proliferation Assays

Cells were seeded at $2.5 \times 10^4$ cells/well and grown in 96 well plates in the presence of $0-1.5 \times 10^{-5}$ M cypate conjugated peptides for 24 or 48 hours. Cell proliferation was measured using the CyQuant proliferation assay from Molecular Probes (Eugene, Oreg.) per the manufacturer's protocol. Briefly, after incubation the microplate was inverted to remove the media and frozen at −70° C. overnight. The microplate was thawed at room temperature and 200 μL of the CyQuant GR dye/cell-lysis buffer was added to each well. After a 5-minute incubation at room temperature in the dark, the fluorescence was measured using a SynergyHT plate reader with 485 nM excitation/520 nM emission filters.

Figure 18:
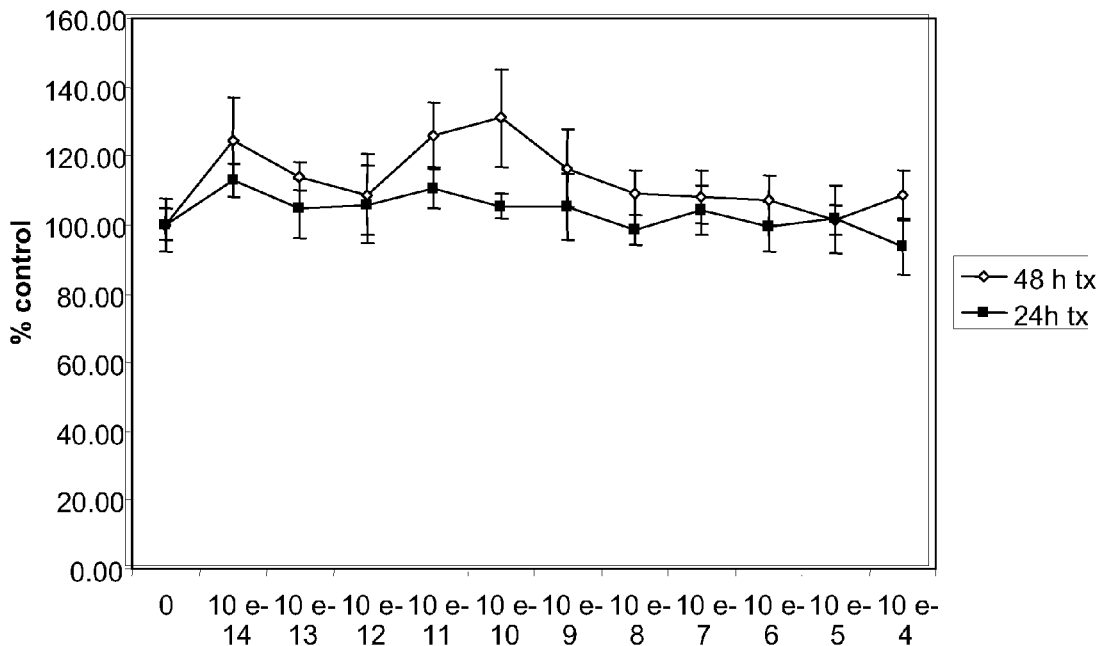
FIG. 18 illustrates that the cypate-peptide conjugates do not affect cell viability. Cyquant cell proliferation assay in A549 cells treated with (A) cypate-GRD, (B) cypate-RGD, and (C) cyclic cypate-RGD.
Figure 18:
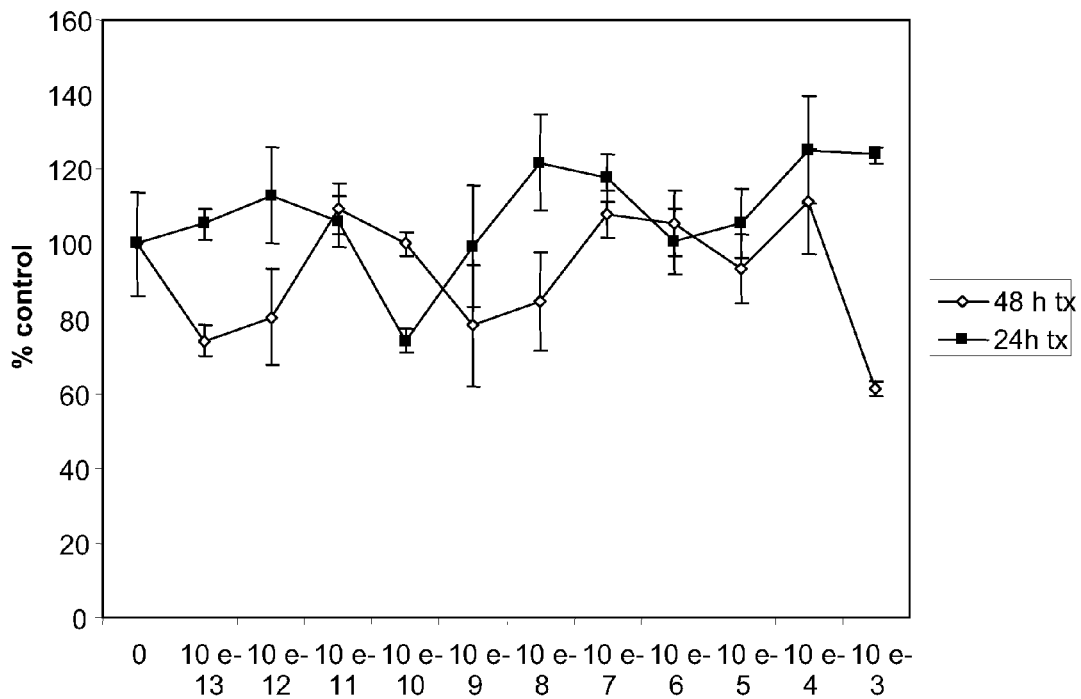
Figure 18C:
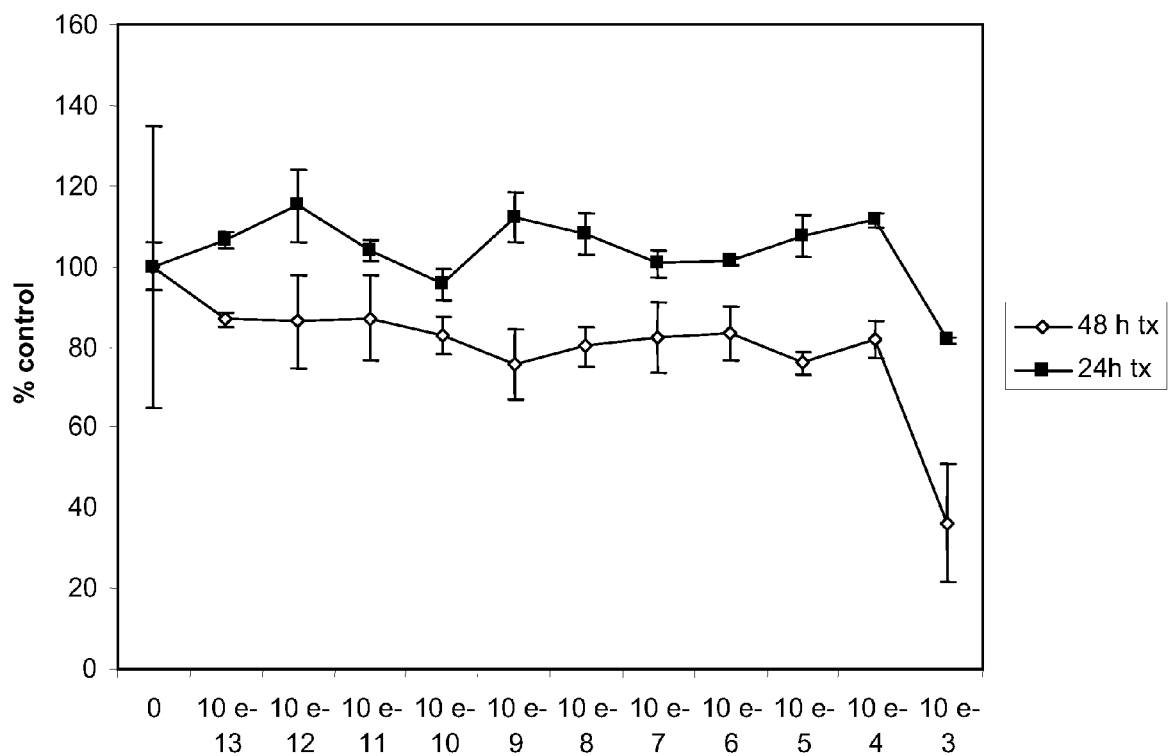

Because the Cyquant assay is based on the adherence of a dye to nucleic acids, the assay is a measure of both proliferative and cytotoxic effects. The results show that none of the compounds tested affected cell proliferation or induced cytotoxicity when cells were treated with concentrations up to 100 μM for 24 hours (FIG. 18). Longer treatment (48 hours) did result in some cytotoxicity with cyclic cypate-RGD and linear cypate RGD, (FIGS. 18B and C), but not with linear cypate-GRD (FIG. 18A).

Optical Imaging

Figure 19A:
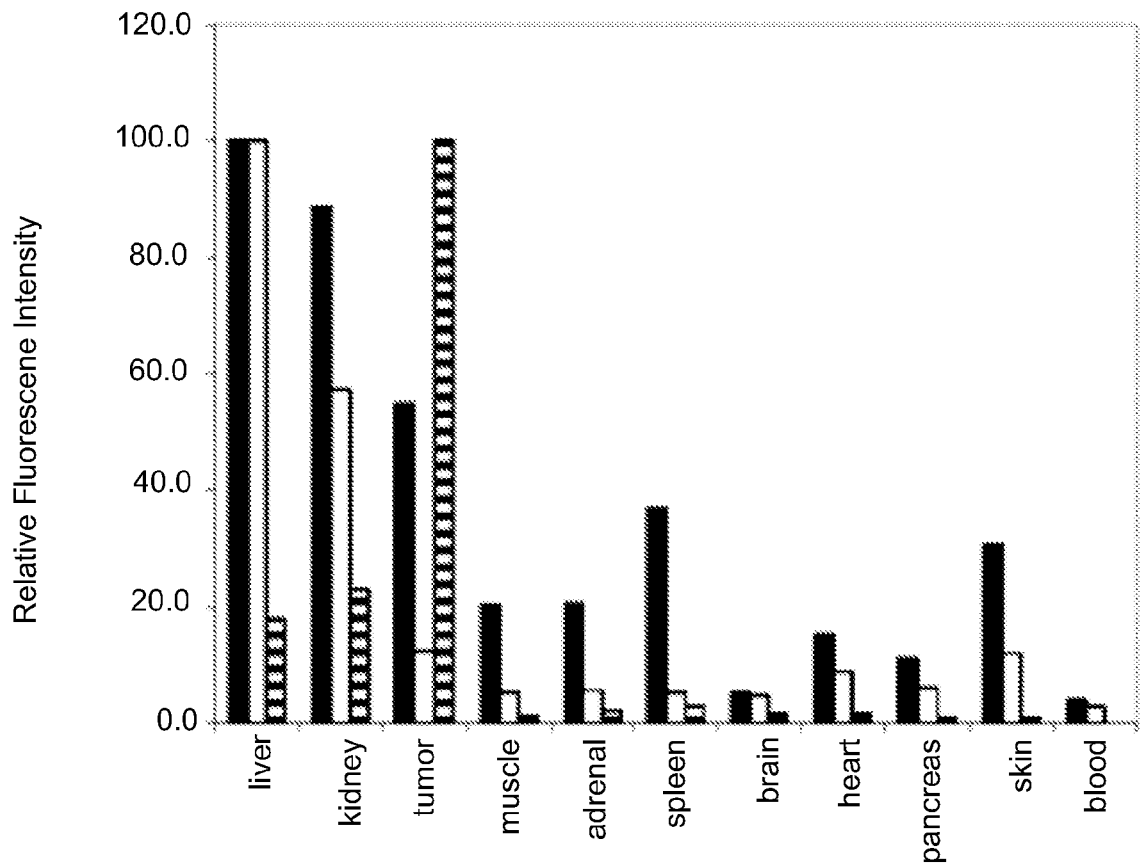
FIG. 19 presents the biodistribution of cypate conjugates in A549 tumor-bearing nude mice at 24 h postinjection. (a) Distribution of cypate-GRD (striped bars), cypate-RGD (white bars), and cyclic cypate-RGD (black bars) in different tissues. (b) Whole-body noninvasive optical imaging of the distribution of cypate-GRD in nude mice.
Figure 19B:
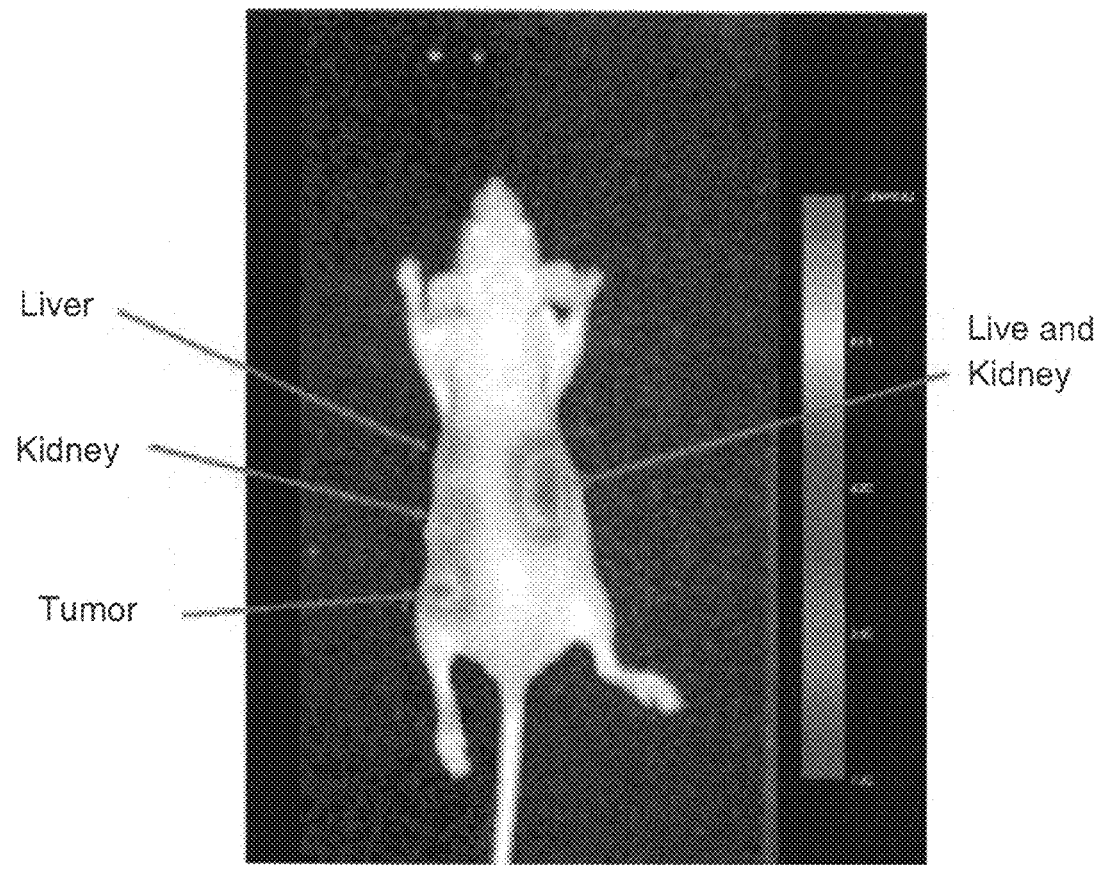

In vivo optical imaging studies using the cypate-peptide optical probes were performed and analyzed as described above in Example 1. At 24 h postinjection, cypate-GRD, linear cypate-RGD, and cyclic cypate-RGD preferentially localized in the ABI-positive A549 tumors grown in nude mice (FIG. 19a). Unlike the RGD compounds, cypate-GRD had higher uptake in the tumor tissue. Furthermore, the retention of cypate-GRD in nontarget tissues, including the major excretion organs (liver and kidneys), were much lower than the two GRD compounds. The superior clearance profile of cypate-GRD provides a strategy to image the expression of $\beta_3$ integrins in vivo.

As in the in vitro studies, the tumor uptake of cypate-GRD can be inhibited by ABI-avid peptides, such as cyclo[RGDfV] [SEQ ID NO:1]. For example, an equimolar amount of this peptide blocked the uptake of cypate-GRD in A549 tumor-bearing mice (data not shown). Typically, higher concentrations (>100×) of the blocking peptides are needed to inhibit the retention of compounds by a common receptor. Therefore, the small dose of cyclo[RGDfV] [SEQ ID NO:1] needed to block the uptake of cypate-GRD confirmed the low binding affinity of cypate-GRD to ABI. However, the weak ligand-receptor interaction does not appear to decrease the uptake of cypate-GRD in tumors. This observation could be explained by the preponderance of the activated form of $\beta_3$ in the in vivo tumor model or the activation of $\beta_3$ subunit by cypate-GRD. Subsequent studies showed that the blocking peptide was unable to displace cypate-GRD in A549 tumor in mice 24 h postinjection of cypate-GRD. This suggests that cypate-GRD 2 was not retained on the tumor cell membranes but probably internalized in the tumor cells by $\beta_3$ integrin receptor. Thus, the superior biodistribution profile of cypate-GRD in vivo provides a strategy to image and monitor the functional status of $\beta_3$ integrin in cells and live animals. The use of NIR fluorescent probes allows the assessment of molecular processes in cells and intact animals without changing the fluorescent labels.

What is claimed is:

1. A compound having the formula:

$$R^1\text{-}[GRDSPK]_n\text{-}R^2$$

wherein:
- $R^1$ and $R^2$ are independently selected from the group consisting of an imaging agent, a treatment agent, hydrogen, hydroxyl, hydrocarbyl, and substituted hydrocarbyl, provided at least one of $R^1$ or $R^2$ is an imaging agent or a treatment agent;
- GRDSPK (SEQ ID NO:8) is a linear or cyclic peptide;
- n is an integer from 1 to about 10; and
- a dash (-) represents a covalent bond.

2. The compound of claim 1, wherein one of $R^1$ or $R^2$ is an imaging agent selected from the group consisting of a fluorescent dye, a fluorescent semiconductor particle, paramagnetic or superparamagnetic material, and a radioisotope.

3. The compound of claim 1, wherein one of $R^1$ or $R^2$ is a treatment agent selected from the group consisting of a drug and a hormone.

4. The compound of claim 1, further comprising a linker, $L^1$, that conjugates $R^1$ to $X^1$.

5. The compound of claim 1, further comprising a linker, $L^2$, that conjugates $R^2$ to $X^2$.

6. The compound of claim 1, wherein n is from 1 to 5.

7. A compound having the formula:

$$R^1\text{-}[X^1_m\text{—}R\text{-}D\text{-}X^2_p]_n\text{-}R^2 \quad (SEQ\ ID\ NO:55)$$

wherein:
- $R^1$ and $R^2$ are independently selected from the group consisting of a carbocyanine dye, a treatment agent, hydrogen, hydroxyl, hydrocarbyl, and substituted hydrocarbyl, provided at least one of $R^1$ or $R^2$ is a carbocyanine dye;
- $X^1_m$—R-D-$X^2_p$ together form a linear or cyclic peptide;
- each $X^1$ and each $X^2$ are independently selected from the group consisting of G, S, N, Q, D, E, K, R, T, Y, C, H, and P;
- m is an integer from 1 to about 10;
- n is an integer from 1 to about 10;
- p is an integer from 1 to about 10; and
- a dash (-) represents a covalent bond.

8. The compound of claim 7, wherein one of $R^1$ or $R^2$ is a treatment agent selected from the group consisting of a drug and a hormone.

9. The compound of claim 7, further comprising a linker, $L^1$, that conjugates $R^1$ to $X^1$.

10. The compound of claim 7, further comprising a linker, $L^2$, that conjugates $R^2$ to $X^2$.

11. The compound of claim 7, wherein:
- n is from 1 to 5;
- m is from 1 to 3; and
- p is from 1 to 3.

12. The compound of claim 7, further comprising at least one cyclic peptide having a RGD motif.

13. The compound of claim 12, wherein the cyclic peptide has from about 4 amino acid residues to about 10 amino acid residues.

14. The compound of claim 7, wherein the carbocyanine dye is cypate.

15. A method for detecting expression of a $\beta_3$ subunit of integrin in a cell, the method comprising:
(a) contacting a population of cells with a compound of claim 7; and
(b) detecting the presence of a signal emitted from the carbocyanine dye of the compound of claim 7 in the population of cells, the signal being emitted from a cell expressing a $\beta_3$ subunit of integrin.

* * * * *

SEQUENCE LISTING

```
<160> NUMBER OF SEQ ID NOS: 55

<210> SEQ ID NO 1
<211> LENGTH: 5
<212> TYPE: PRT
<213> ORGANISM: Homo sapiens
<220> FEATURE:
<221> NAME/KEY: MISC_FEATURE
<222> LOCATION: (1)..(5)
<223> OTHER INFORMATION: CYCLIC PEPTIDE
<220> FEATURE:
<221> NAME/KEY: MISC_FEATURE
<222> LOCATION: (4)..(4)
<223> OTHER INFORMATION: X=D-PHENYLALANINE

<400> SEQUENCE: 1

Arg Gly Asp Xaa Val
1               5

<210> SEQ ID NO 2
<211> LENGTH: 6
<212> TYPE: PRT
<213> ORGANISM: Homo sapiens
<220> FEATURE:
<221> NAME/KEY: MISC_FEATURE
<222> LOCATION: (1)..(6)
<223> OTHER INFORMATION: CYCLIC PEPTIDE
<220> FEATURE:
<221> NAME/KEY: MISC_FEATURE
<222> LOCATION: (1)..(1)
<223> OTHER INFORMATION: CYPATE DYE ATTACHED
```

```
<400> SEQUENCE: 2

Cys Arg Gly Asp Asp Cys
1               5

<210> SEQ ID NO 3
<211> LENGTH: 6
<212> TYPE: PRT
<213> ORGANISM: Homo sapiens
<220> FEATURE:
<221> NAME/KEY: MISC_FEATURE
<222> LOCATION: (1)..(1)
<223> OTHER INFORMATION: CYPATE DYE ATTACHED
<220> FEATURE:
<221> NAME/KEY: MISC_FEATURE
<222> LOCATION: (1)..(6)
<223> OTHER INFORMATION: CYCLIC PEPTIDE

<400> SEQUENCE: 3

Cys Arg Gly Asp Leu Cys
1               5

<210> SEQ ID NO 4
<211> LENGTH: 5
<212> TYPE: PRT
<213> ORGANISM: Homo sapiens
<220> FEATURE:
<221> NAME/KEY: MISC_FEATURE
<222> LOCATION: (1)..(5)
<223> OTHER INFORMATION: CYCLIC PEPTIDE
<220> FEATURE:
<221> NAME/KEY: MISC_FEATURE
<222> LOCATION: (1)..(1)
<223> OTHER INFORMATION: CYPATE DYE ATTACHED
<220> FEATURE:
<221> NAME/KEY: MISC_FEATURE
<222> LOCATION: (5)..(5)
<223> OTHER INFORMATION: X = D-PHENYALANINE

<400> SEQUENCE: 4

Lys Arg Gly Asp Xaa
1               5

<210> SEQ ID NO 5
<211> LENGTH: 7
<212> TYPE: PRT
<213> ORGANISM: Homo sapiens
<220> FEATURE:
<221> NAME/KEY: MISC_FEATURE
<222> LOCATION: (1)..(1)
<223> OTHER INFORMATION: CYPATE DYE ATTACHED

<400> SEQUENCE: 5

Gly Arg Gly Asp Ser Pro Lys
1               5

<210> SEQ ID NO 6
<211> LENGTH: 6
<212> TYPE: PRT
<213> ORGANISM: Homo sapiens
<220> FEATURE:
<221> NAME/KEY: MISC_FEATURE
<222> LOCATION: (1)..(1)
<223> OTHER INFORMATION: CYPATE DYE ATTACHED

<400> SEQUENCE: 6

Gly Arg Asp Ser Pro Lys
1               5

<210> SEQ ID NO 7
```

```
<211> LENGTH: 6
<212> TYPE: PRT
<213> ORGANISM: Homo sapiens
<220> FEATURE:
<221> NAME/KEY: MISC_FEATURE
<222> LOCATION: (1)..(1)
<223> OTHER INFORMATION: CYPATE DYE ATTACHED
<220> FEATURE:
<221> NAME/KEY: MISC_FEATURE
<222> LOCATION: (1)..(6)
<223> OTHER INFORMATION: CYCLIC PEPTIDE
<220> FEATURE:
<221> NAME/KEY: MISC_FEATURE
<222> LOCATION: (5)..(5)
<223> OTHER INFORMATION: X = D-PHENYLALANINE

<400> SEQUENCE: 7

Lys Arg Gly Asp Xaa Val
1               5

<210> SEQ ID NO 8
<211> LENGTH: 6
<212> TYPE: PRT
<213> ORGANISM: Homo sapiens

<400> SEQUENCE: 8

Gly Arg Asp Ser Pro Lys
1               5

<210> SEQ ID NO 9
<211> LENGTH: 6
<212> TYPE: PRT
<213> ORGANISM: Homo sapiens
<220> FEATURE:
<221> NAME/KEY: MISC_FEATURE
<222> LOCATION: (1)..(1)
<223> OTHER INFORMATION: CYPATE DYE ATTACHED

<400> SEQUENCE: 9

Gly Arg Gly Asp Pro Lys
1               5

<210> SEQ ID NO 10
<211> LENGTH: 6
<212> TYPE: PRT
<213> ORGANISM: Homo sapiens
<220> FEATURE:
<221> NAME/KEY: MISC_FEATURE
<222> LOCATION: (1)..(1)
<223> OTHER INFORMATION: CYPATE-3 DYE ATTACHED

<400> SEQUENCE: 10

Gly Arg Asp Ser Pro Lys
1               5

<210> SEQ ID NO 11
<211> LENGTH: 6
<212> TYPE: PRT
<213> ORGANISM: Homo sapiens
<220> FEATURE:
<221> NAME/KEY: MISC_FEATURE
<222> LOCATION: (1)..(6)
<223> OTHER INFORMATION: CYCLIC PEPTIDE
<220> FEATURE:
<221> NAME/KEY: MISC_FEATURE
<222> LOCATION: (4)..(4)
<223> OTHER INFORMATION: X = D-PHENYLALANINE
<220> FEATURE:
<221> NAME/KEY: MISC_FEATURE
<222> LOCATION: (6)..(6)
<223> OTHER INFORMATION: CYPATE DYE ATTACHED
```

```
<400> SEQUENCE: 11

Arg Gly Asp Xaa Val Leu
1               5

<210> SEQ ID NO 12
<211> LENGTH: 6
<212> TYPE: PRT
<213> ORGANISM: Homo sapiens
<220> FEATURE:
<221> NAME/KEY: MOD_RES
<222> LOCATION: (1)..(1)
<223> OTHER INFORMATION: Dde protecting group attached
<220> FEATURE:
<221> NAME/KEY: MOD_RES
<222> LOCATION: (2)..(2)
<223> OTHER INFORMATION: Pbf protecting group attached
<220> FEATURE:
<221> NAME/KEY: MOD_RES
<222> LOCATION: (4)..(4)
<223> OTHER INFORMATION: Obut protecting group attached
<220> FEATURE:
<221> NAME/KEY: MISC_FEATURE
<222> LOCATION: (5)..(5)
<223> OTHER INFORMATION: X = D-PHENYLALANINE

<400> SEQUENCE: 12

Lys Arg Gly Asp Xaa Val
1               5

<210> SEQ ID NO 13
<211> LENGTH: 6
<212> TYPE: PRT
<213> ORGANISM: Homo sapiens
<220> FEATURE:
<221> NAME/KEY: MISC_FEATURE
<222> LOCATION: (1)..(6)
<223> OTHER INFORMATION: CYCLIC PEPTIDE
<220> FEATURE:
<221> NAME/KEY: MOD_RES
<222> LOCATION: (1)..(1)
<223> OTHER INFORMATION: Pbf protecting group attached
<220> FEATURE:
<221> NAME/KEY: MOD_RES
<222> LOCATION: (3)..(3)
<223> OTHER INFORMATION: Obut protecting group attached
<220> FEATURE:
<221> NAME/KEY: MISC_FEATURE
<222> LOCATION: (4)..(4)
<223> OTHER INFORMATION: X = D-PHENYLALANINE

<400> SEQUENCE: 13

Arg Gly Asp Xaa Val Lys
1               5

<210> SEQ ID NO 14
<211> LENGTH: 6
<212> TYPE: PRT
<213> ORGANISM: Homo sapiens
<220> FEATURE:
<221> NAME/KEY: MISC_FEATURE
<222> LOCATION: (1)..(6)
<223> OTHER INFORMATION: CYCLIC PEPTIDE
<220> FEATURE:
<221> NAME/KEY: MOD_RES
<222> LOCATION: (1)..(1)
<223> OTHER INFORMATION: Pbf protecting group attached
<220> FEATURE:
<221> NAME/KEY: MOD_RES
<222> LOCATION: (3)..(3)
<223> OTHER INFORMATION: Obut protecting group attached
<220> FEATURE:
<221> NAME/KEY: MISC_FEATURE
<222> LOCATION: (4)..(4)
<223> OTHER INFORMATION: X = D-PHENYLALANINE
```

```
<220> FEATURE:
<221> NAME/KEY: MOD_RES
<222> LOCATION: (6)..(6)
<223> OTHER INFORMATION: Dde protecting group attached

<400> SEQUENCE: 14

Arg Gly Asp Xaa Val Lys
1               5

<210> SEQ ID NO 15
<211> LENGTH: 6
<212> TYPE: PRT
<213> ORGANISM: Homo sapiens
<220> FEATURE:
<221> NAME/KEY: MISC_FEATURE
<222> LOCATION: (1)..(1)
<223> OTHER INFORMATION: DODECYLTETRA ACETIC ACID ATTACHED

<400> SEQUENCE: 15

Gly Arg Asp Ser Pro Lys
1               5

<210> SEQ ID NO 16
<211> LENGTH: 6
<212> TYPE: PRT
<213> ORGANISM: Homo sapiens
<220> FEATURE:
<221> NAME/KEY: MOD_RES
<222> LOCATION: (1)..(1)
<223> OTHER INFORMATION: Acm protecting group attached
<220> FEATURE:
<221> NAME/KEY: MOD_RES
<222> LOCATION: (2)..(2)
<223> OTHER INFORMATION: Pbf protecting group attached
<220> FEATURE:
<221> NAME/KEY: MOD_RES
<222> LOCATION: (4)..(4)
<223> OTHER INFORMATION: OBut protecting group attached
<220> FEATURE:
<221> NAME/KEY: MISC_FEATURE
<222> LOCATION: (5)..(5)
<223> OTHER INFORMATION: X = ANY AMINO ACID
<220> FEATURE:
<221> NAME/KEY: MOD_RES
<222> LOCATION: (6)..(6)
<223> OTHER INFORMATION: Acm protecting group attached

<400> SEQUENCE: 16

Cys Arg Gly Asp Xaa Cys
1               5

<210> SEQ ID NO 17
<211> LENGTH: 6
<212> TYPE: PRT
<213> ORGANISM: Homo sapiens
<220> FEATURE:
<221> NAME/KEY: MISC_FEATURE
<222> LOCATION: (1)..(6)
<223> OTHER INFORMATION: CYCLIC PEPTIDE
<220> FEATURE:
<221> NAME/KEY: MOD_RES
<222> LOCATION: (2)..(2)
<223> OTHER INFORMATION: Pbf protecting group attached
<220> FEATURE:
<221> NAME/KEY: MOD_RES
<222> LOCATION: (4)..(4)
<223> OTHER INFORMATION: OBut protecting group attached
<220> FEATURE:
<221> NAME/KEY: MISC_FEATURE
<222> LOCATION: (5)..(5)
<223> OTHER INFORMATION: X = ANY AMINO ACID

<400> SEQUENCE: 17
```

-continued

```
Cys Arg Gly Asp Xaa Cys
1               5

<210> SEQ ID NO 18
<211> LENGTH: 6
<212> TYPE: PRT
<213> ORGANISM: Homo sapiens
<220> FEATURE:
<221> NAME/KEY: MISC_FEATURE
<222> LOCATION: (1)..(6)
<223> OTHER INFORMATION: CYCLIC PEPTIDE
<220> FEATURE:
<221> NAME/KEY: MISC_FEATURE
<222> LOCATION: (1)..(1)
<223> OTHER INFORMATION: CYPATE DYE ATTACHED
<220> FEATURE:
<221> NAME/KEY: MISC_FEATURE
<222> LOCATION: (5)..(5)
<223> OTHER INFORMATION: X = ANY AMINO ACID

<400> SEQUENCE: 18

Cys Arg Gly Asp Xaa Cys
1               5

<210> SEQ ID NO 19
<211> LENGTH: 5
<212> TYPE: PRT
<213> ORGANISM: Homo sapiens
<220> FEATURE:
<221> NAME/KEY: MISC_FEATURE
<222> LOCATION: (1)..(5)
<223> OTHER INFORMATION: CYCLIC PEPTIDE
<220> FEATURE:
<221> NAME/KEY: MISC_FEATURE
<222> LOCATION: (1)..(1)
<223> OTHER INFORMATION: CYPATE DYE ATTACHED

<400> SEQUENCE: 19

Cys Arg Gly Asp Cys
1               5

<210> SEQ ID NO 20
<211> LENGTH: 6
<212> TYPE: PRT
<213> ORGANISM: Homo sapiens
<220> FEATURE:
<221> NAME/KEY: MISC_FEATURE
<222> LOCATION: (1)..(6)
<223> OTHER INFORMATION: CYCLIC PEPTIDE
<220> FEATURE:
<221> NAME/KEY: MISC_FEATURE
<222> LOCATION: (1)..(1)
<223> OTHER INFORMATION: CYPATE DYE ATTACHED

<400> SEQUENCE: 20

Cys Arg Gly Asp Ser Cys
1               5

<210> SEQ ID NO 21
<211> LENGTH: 7
<212> TYPE: PRT
<213> ORGANISM: Homo sapiens
<220> FEATURE:
<221> NAME/KEY: MISC_FEATURE
<222> LOCATION: (1)..(7)
<223> OTHER INFORMATION: CYCLIC PEPTIDE
<220> FEATURE:
<221> NAME/KEY: MISC_FEATURE
<222> LOCATION: (1)..(1)
<223> OTHER INFORMATION: CYPATE DYE ATTACHED

<400> SEQUENCE: 21
```

```
Cys Arg Gly Asp Gly Arg Cys
1               5

<210> SEQ ID NO 22
<211> LENGTH: 6
<212> TYPE: PRT
<213> ORGANISM: Homo sapiens
<220> FEATURE:
<221> NAME/KEY: MISC_FEATURE
<222> LOCATION: (1)..(6)
<223> OTHER INFORMATION: CYCLIC PEPTIDE
<220> FEATURE:
<221> NAME/KEY: MISC_FEATURE
<222> LOCATION: (1)..(1)
<223> OTHER INFORMATION: CYPATE DYE ATTACHED

<400> SEQUENCE: 22

Cys Arg Gly Asp Leu Cys
1               5

<210> SEQ ID NO 23
<211> LENGTH: 6
<212> TYPE: PRT
<213> ORGANISM: Homo sapiens
<220> FEATURE:
<221> NAME/KEY: MISC_FEATURE
<222> LOCATION: (1)..(6)
<223> OTHER INFORMATION: CYCLIC PEPTIDE
<220> FEATURE:
<221> NAME/KEY: MISC_FEATURE
<222> LOCATION: (1)..(1)
<223> OTHER INFORMATION: CYPATE DYE ATTACHED

<400> SEQUENCE: 23

Cys Arg Gly Asp Pro Cys
1               5

<210> SEQ ID NO 24
<211> LENGTH: 6
<212> TYPE: PRT
<213> ORGANISM: Homo sapiens
<220> FEATURE:
<221> NAME/KEY: MISC_FEATURE
<222> LOCATION: (1)..(1)
<223> OTHER INFORMATION: X = D-PHENYLALANINE
<220> FEATURE:
<221> NAME/KEY: MISC_FEATURE
<222> LOCATION: (1)..(6)
<223> OTHER INFORMATION: CYCLIC PEPTIDE

<400> SEQUENCE: 24

Xaa Val Lys Arg Gly Asp
1               5

<210> SEQ ID NO 25
<211> LENGTH: 6
<212> TYPE: PRT
<213> ORGANISM: Homo sapiens
<220> FEATURE:
<221> NAME/KEY: MISC_FEATURE
<222> LOCATION: (1)..(5)
<223> OTHER INFORMATION: CYCLIC PEPTIDE
<220> FEATURE:
<221> NAME/KEY: MISC_FEATURE
<222> LOCATION: (4)..(4)
<223> OTHER INFORMATION: X = D-PHENYLALANINE

<400> SEQUENCE: 25

Arg Gly Asp Xaa Asp Lys
1               5
```

```
<210> SEQ ID NO 26
<211> LENGTH: 7
<212> TYPE: PRT
<213> ORGANISM: Homo sapiens
<220> FEATURE:
<221> NAME/KEY: misc_feature
<222> LOCATION: (1)..(5)
<223> OTHER INFORMATION: CYCLIC PEPTIDE
<220> FEATURE:
<221> NAME/KEY: misc_feature
<222> LOCATION: (4)..(4)
<223> OTHER INFORMATION: X = D-PHENYLALANINE
<220> FEATURE:
<221> NAME/KEY: misc_feature
<222> LOCATION: (6)..(6)
<223> OTHER INFORMATION: X = AMINOHEXANOIC ACID

<400> SEQUENCE: 26

Arg Gly Asp Xaa Asp Xaa Lys
1               5

<210> SEQ ID NO 27
<211> LENGTH: 6
<212> TYPE: PRT
<213> ORGANISM: Homo sapiens
<220> FEATURE:
<221> NAME/KEY: MISC_FEATURE
<222> LOCATION: (1)..(1)
<223> OTHER INFORMATION: CYPATE DYE ATTACHED
<220> FEATURE:
<221> NAME/KEY: MISC_FEATURE
<222> LOCATION: (5)..(5)
<223> OTHER INFORMATION: X = D-PHENYLALANINE
<220> FEATURE:
<221> NAME/KEY: MISC_FEATURE
<222> LOCATION: (6)..(6)
<223> OTHER INFORMATION: X = AMINOHEXANOIC ACID

<400> SEQUENCE: 27

Lys Arg Gly Asp Xaa Xaa
1               5

<210> SEQ ID NO 28
<211> LENGTH: 8
<212> TYPE: PRT
<213> ORGANISM: Homo sapiens
<220> FEATURE:
<221> NAME/KEY: MISC_FEATURE
<222> LOCATION: (1)..(1)
<223> OTHER INFORMATION: CYPATE DYE ATTACHED
<220> FEATURE:
<221> NAME/KEY: MISC_FEATURE
<222> LOCATION: (5)..(5)
<223> OTHER INFORMATION: X = D-PHENYLALANINE
<220> FEATURE:
<221> NAME/KEY: MISC_FEATURE
<222> LOCATION: (7)..(7)
<223> OTHER INFORMATION: X = D-PHENYLALANINE
<220> FEATURE:
<221> NAME/KEY: MISC_FEATURE
<222> LOCATION: (8)..(8)
<223> OTHER INFORMATION: X = AMINOHEXANOIC ACID

<400> SEQUENCE: 28

Lys Arg Gly Asp Xaa Asp Xaa Xaa
1               5

<210> SEQ ID NO 29
<211> LENGTH: 12
<212> TYPE: PRT
<213> ORGANISM: Homo sapiens
<220> FEATURE:
<221> NAME/KEY: MISC_FEATURE
<222> LOCATION: (1)..(1)
```

```
<223> OTHER INFORMATION: X = D-PHENYLALANINE
<220> FEATURE:
<221> NAME/KEY: MISC_FEATURE
<222> LOCATION: (1)..(1)
<223> OTHER INFORMATION: CYPATE DYE ATTACHED
<220> FEATURE:
<221> NAME/KEY: MISC_FEATURE
<222> LOCATION: (2)..(7)
<223> OTHER INFORMATION: CYCLIC PEPTIDE
<220> FEATURE:
<221> NAME/KEY: MISC_FEATURE
<222> LOCATION: (4)..(4)
<223> OTHER INFORMATION: X=D-TRYPTOPHAN

<400> SEQUENCE: 29

Xaa Cys Tyr Xaa Lys Thr Cys Thr Val Arg Gly Asp
1               5                   10

<210> SEQ ID NO 30
<211> LENGTH: 5
<212> TYPE: PRT
<213> ORGANISM: Homo sapiens
<220> FEATURE:
<221> NAME/KEY: misc_feature
<222> LOCATION: (1)..(1)
<223> OTHER INFORMATION: X=D-PHENYLALANINE

<400> SEQUENCE: 30

Xaa Val Arg Gly Asp
1               5

<210> SEQ ID NO 31
<211> LENGTH: 15
<212> TYPE: PRT
<213> ORGANISM: Homo sapiens
<220> FEATURE:
<221> NAME/KEY: MISC_FEATURE
<222> LOCATION: (1)..(1)
<223> OTHER INFORMATION: X = B-ALANINE
<220> FEATURE:
<221> NAME/KEY: MISC_FEATURE
<222> LOCATION: (1)..(1)
<223> OTHER INFORMATION: CYPATE DYE ATTACHED
<220> FEATURE:
<221> NAME/KEY: MISC_FEATURE
<222> LOCATION: (5)..(5)
<223> OTHER INFORMATION: X = AMINOHEXANOIC ACID
<220> FEATURE:
<221> NAME/KEY: MISC_FEATURE
<222> LOCATION: (9)..(9)
<223> OTHER INFORMATION: X = AMINOHEXANOIC ACID

<400> SEQUENCE: 31

Xaa Arg Gly Asp Xaa Arg Gly Asp Xaa Arg Gly Asp Ser Pro Lys
1               5                   10                  15

<210> SEQ ID NO 32
<211> LENGTH: 8
<212> TYPE: PRT
<213> ORGANISM: Homo sapiens

<400> SEQUENCE: 32

His Asp Arg Gly Asp Cys Phe Lys
1               5

<210> SEQ ID NO 33
<211> LENGTH: 9
<212> TYPE: PRT
<213> ORGANISM: Homo sapiens
<220> FEATURE:
<221> NAME/KEY: MISC_FEATURE
<222> LOCATION: (1)..(1)
```

```
<223> OTHER INFORMATION: X = BETA-ALANINE
<220> FEATURE:
<221> NAME/KEY: MISC_FEATURE
<222> LOCATION: (7)..(7)
<223> OTHER INFORMATION: ETHYL GROUP ATTACHED

<400> SEQUENCE: 33

Xaa Asp Cys Arg Gly Asp Cys Phe Val
1               5

<210> SEQ ID NO 34
<211> LENGTH: 9
<212> TYPE: PRT
<213> ORGANISM: Homo sapiens
<220> FEATURE:
<221> NAME/KEY: MISC_FEATURE
<222> LOCATION: (1)..(1)
<223> OTHER INFORMATION: DIETHYLENE TRIAMINE PENTA ACETATE ATTACHED
<220> FEATURE:
<221> NAME/KEY: MISC_FEATURE
<222> LOCATION: (3)..(3)
<223> OTHER INFORMATION: ETHYL GROUP ATTACHED
<220> FEATURE:
<221> NAME/KEY: MISC_FEATURE
<222> LOCATION: (7)..(7)
<223> OTHER INFORMATION: ETHYL GROUP ATTACHED

<400> SEQUENCE: 34

His Asp Cys Arg Gly Asp Cys Phe Lys
1               5

<210> SEQ ID NO 35
<211> LENGTH: 5
<212> TYPE: PRT
<213> ORGANISM: Homo sapiens
<220> FEATURE:
<221> NAME/KEY: MISC_FEATURE
<222> LOCATION: (1)..(5)
<223> OTHER INFORMATION: CYCLIC PEPTIDE
<220> FEATURE:
<221> NAME/KEY: MISC_FEATURE
<222> LOCATION: (1)..(1)
<223> OTHER INFORMATION: X = D-PHENYLALANINE

<400> SEQUENCE: 35

Xaa Val Arg Gly Asp
1               5

<210> SEQ ID NO 36
<211> LENGTH: 12
<212> TYPE: PRT
<213> ORGANISM: Homo sapiens
<220> FEATURE:
<221> NAME/KEY: MISC_FEATURE
<222> LOCATION: (1)..(1)
<223> OTHER INFORMATION: DIETHYLENE TRIAMINE PENTA ACETATE ATTACHED
<220> FEATURE:
<221> NAME/KEY: MISC_FEATURE
<222> LOCATION: (5)..(5)
<223> OTHER INFORMATION: X = D-PHENYLALANINE
<220> FEATURE:
<221> NAME/KEY: MISC_FEATURE
<222> LOCATION: (6)..(11)
<223> OTHER INFORMATION: CYCLIC PEPTIDE
<220> FEATURE:
<221> NAME/KEY: MISC_FEATURE
<222> LOCATION: (8)..(8)
<223> OTHER INFORMATION: X=D-TRYPTOPHAN

<400> SEQUENCE: 36

Val Arg Gly Asp Xaa Cys Tyr Xaa Lys Thr Cys Thr
1               5                   10
```

```
<210> SEQ ID NO 37
<211> LENGTH: 12
<212> TYPE: PRT
<213> ORGANISM: Homo sapiens
<220> FEATURE:
<221> NAME/KEY: MISC_FEATURE
<222> LOCATION: (1)..(1)
<223> OTHER INFORMATION: X = D-PHENYLALANINE
<220> FEATURE:
<221> NAME/KEY: MISC_FEATURE
<222> LOCATION: (1)..(1)
<223> OTHER INFORMATION: DIETHYLENE TRIAMINE PENTA ACETATE ATTACHED
<220> FEATURE:
<221> NAME/KEY: MISC_FEATURE
<222> LOCATION: (2)..(7)
<223> OTHER INFORMATION: CYCLIC PEPTIDE
<220> FEATURE:
<221> NAME/KEY: MISC_FEATURE
<222> LOCATION: (4)..(4)
<223> OTHER INFORMATION: X=D-TRYPTOPHAN

<400> SEQUENCE: 37

Xaa Cys Tyr Xaa Lys Thr Cys Thr Val Arg Gly Asp
1               5                   10

<210> SEQ ID NO 38
<211> LENGTH: 13
<212> TYPE: PRT
<213> ORGANISM: Homo sapiens
<220> FEATURE:
<221> NAME/KEY: MISC_FEATURE
<222> LOCATION: (1)..(1)
<223> OTHER INFORMATION: DIETHYLENE TRIAMINE PENTA ACETATE ATTACHED
<220> FEATURE:
<221> NAME/KEY: MISC_FEATURE
<222> LOCATION: (1)..(1)
<223> OTHER INFORMATION: X = D-PHENYLALANINE
<220> FEATURE:
<221> NAME/KEY: MISC_FEATURE
<222> LOCATION: (2)..(7)
<223> OTHER INFORMATION: CYCLIC PEPTIDE
<220> FEATURE:
<221> NAME/KEY: MISC_FEATURE
<222> LOCATION: (4)..(4)
<223> OTHER INFORMATION: X=D-TRYPTOPHAN
<220> FEATURE:
<221> NAME/KEY: MISC_FEATURE
<222> LOCATION: (13)..(13)
<223> OTHER INFORMATION: X = D-PHENYLALANINE

<400> SEQUENCE: 38

Xaa Cys Tyr Xaa Lys Thr Cys Thr Val Arg Gly Asp Xaa
1               5                   10

<210> SEQ ID NO 39
<211> LENGTH: 12
<212> TYPE: PRT
<213> ORGANISM: Homo sapiens
<220> FEATURE:
<221> NAME/KEY: MISC_FEATURE
<222> LOCATION: (1)..(1)
<223> OTHER INFORMATION: X = D-PHENYLALANINE
<220> FEATURE:
<221> NAME/KEY: MISC_FEATURE
<222> LOCATION: (2)..(7)
<223> OTHER INFORMATION: CYCLIC PEPTIDE
<220> FEATURE:
<221> NAME/KEY: MISC_FEATURE
<222> LOCATION: (4)..(4)
<223> OTHER INFORMATION: X=D-TRYPTOPHAN

<400> SEQUENCE: 39

Xaa Cys Tyr Xaa Lys Thr Cys Thr Val Arg Gly Asp
1               5                   10
```

```
<210> SEQ ID NO 40
<211> LENGTH: 13
<212> TYPE: PRT
<213> ORGANISM: Homo sapiens
<220> FEATURE:
<221> NAME/KEY: MISC_FEATURE
<222> LOCATION: (1)..(1)
<223> OTHER INFORMATION: X=D-PHENYLALANINE
<220> FEATURE:
<221> NAME/KEY: MISC_FEATURE
<222> LOCATION: (2)..(7)
<223> OTHER INFORMATION: CYCLIC PEPTIDE
<220> FEATURE:
<221> NAME/KEY: MISC_FEATURE
<222> LOCATION: (4)..(4)
<223> OTHER INFORMATION: X=D-TRYPTOPHAN
<220> FEATURE:
<221> NAME/KEY: MISC_FEATURE
<222> LOCATION: (13)..(13)
<223> OTHER INFORMATION: X = D-PHENYLALANINE

<400> SEQUENCE: 40

Xaa Cys Tyr Xaa Lys Thr Cys Thr Val Arg Gly Asp Xaa
1               5                   10

<210> SEQ ID NO 41
<211> LENGTH: 12
<212> TYPE: PRT
<213> ORGANISM: Homo sapiens
<220> FEATURE:
<221> NAME/KEY: MISC_FEATURE
<222> LOCATION: (5)..(5)
<223> OTHER INFORMATION: X = D-PHENYLALANINE
<220> FEATURE:
<221> NAME/KEY: MISC_FEATURE
<222> LOCATION: (6)..(11)
<223> OTHER INFORMATION: CYCLIC PEPTIDE
<220> FEATURE:
<221> NAME/KEY: MISC_FEATURE
<222> LOCATION: (8)..(8)
<223> OTHER INFORMATION: X=D-TRYPTOPHAN

<400> SEQUENCE: 41

Val Arg Gly Asp Xaa Cys Tyr Xaa Lys Thr Cys Thr
1               5                   10

<210> SEQ ID NO 42
<211> LENGTH: 6
<212> TYPE: PRT
<213> ORGANISM: Homo sapiens
<220> FEATURE:
<221> NAME/KEY: MISC_FEATURE
<222> LOCATION: (1)..(1)
<223> OTHER INFORMATION: DIETHYLENE TRIAMINE PENTA ACETATE ATTACHED

<400> SEQUENCE: 42

Gly Arg Asp Ser Pro Lys
1               5

<210> SEQ ID NO 43
<211> LENGTH: 7
<212> TYPE: PRT
<213> ORGANISM: Homo sapiens
<220> FEATURE:
<221> NAME/KEY: MISC_FEATURE
<222> LOCATION: (1)..(1)
<223> OTHER INFORMATION: DIETHYLENE TRIAMINE PENTA ACETATE ATTACHED

<400> SEQUENCE: 43

Gly Arg Gly Asp Ser Pro Lys
1               5
```

```
<210> SEQ ID NO 44
<211> LENGTH: 6
<212> TYPE: PRT
<213> ORGANISM: Homo sapiens
<220> FEATURE:
<221> NAME/KEY: MISC_FEATURE
<222> LOCATION: (1)..(1)
<223> OTHER INFORMATION: DODECYLTETRA ACETIC ACID ATTACHED

<400> SEQUENCE: 44

Arg Gly Asp Ser Pro Lys
1               5

<210> SEQ ID NO 45
<211> LENGTH: 6
<212> TYPE: PRT
<213> ORGANISM: Homo sapiens
<220> FEATURE:
<221> NAME/KEY: MISC_FEATURE
<222> LOCATION: (1)..(1)
<223> OTHER INFORMATION: DODECYLTETRA ACETIC ACID ATTACHED
<220> FEATURE:
<221> NAME/KEY: MISC_FEATURE
<222> LOCATION: (6)..(6)
<223> OTHER INFORMATION: CYPATE DYE ATTACHED

<400> SEQUENCE: 45

Arg Gly Asp Ser Pro Lys
1               5

<210> SEQ ID NO 46
<211> LENGTH: 6
<212> TYPE: PRT
<213> ORGANISM: Homo sapiens
<220> FEATURE:
<221> NAME/KEY: MISC_FEATURE
<222> LOCATION: (6)..(6)
<223> OTHER INFORMATION: CYPATE DYE ATTACHED

<400> SEQUENCE: 46

Arg Gly Asp Ser Pro Lys
1               5

<210> SEQ ID NO 47
<211> LENGTH: 8
<212> TYPE: PRT
<213> ORGANISM: Homo sapiens
<220> FEATURE:
<221> NAME/KEY: MISC_FEATURE
<222> LOCATION: (1)..(1)
<223> OTHER INFORMATION: CYPATE DYE ATTACHED
<220> FEATURE:
<221> NAME/KEY: MISC_FEATURE
<222> LOCATION: (1)..(1)
<223> OTHER INFORMATION: X = B-ALANINE
<220> FEATURE:
<221> NAME/KEY: MISC_FEATURE
<222> LOCATION: (7)..(7)
<223> OTHER INFORMATION: X = D-PHENYLALANINE

<400> SEQUENCE: 47

Xaa Cys Arg Gly Asp Cys Xaa Val
1               5

<210> SEQ ID NO 48
<211> LENGTH: 4
<212> TYPE: PRT
<213> ORGANISM: Homo sapiens
<220> FEATURE:
<221> NAME/KEY: MISC_FEATURE
```

```
<222> LOCATION: (1)..(1)
<223> OTHER INFORMATION: CYPATE DYE ATTACHED
<220> FEATURE:
<221> NAME/KEY: MISC_FEATURE
<222> LOCATION: (4)..(4)
<223> OTHER INFORMATION: D-GLUCOSAMINE ATTACHED

<400> SEQUENCE: 48

Arg Gly Asp Ser
1

<210> SEQ ID NO 49
<211> LENGTH: 6
<212> TYPE: PRT
<213> ORGANISM: Homo sapiens
<220> FEATURE:
<221> NAME/KEY: MISC_FEATURE
<222> LOCATION: (1)..(1)
<223> OTHER INFORMATION: CYPATE DYE ATTACHED
<220> FEATURE:
<221> NAME/KEY: MISC_FEATURE
<222> LOCATION: (1)..(6)
<223> OTHER INFORMATION: CYCLIC PEPTIDE
<220> FEATURE:
<221> NAME/KEY: MISC_FEATURE
<222> LOCATION: (6)..(6)
<223> OTHER INFORMATION: D-GLUCOSAMINE ATTACHED

<400> SEQUENCE: 49

Cys Arg Gly Asp Ser Cys
1               5

<210> SEQ ID NO 50
<211> LENGTH: 3
<212> TYPE: PRT
<213> ORGANISM: Homo sapiens
<220> FEATURE:
<221> NAME/KEY: MISC_FEATURE
<222> LOCATION: (1)..(1)
<223> OTHER INFORMATION: CYPATE DYE ATTACHED
<220> FEATURE:
<221> NAME/KEY: MISC_FEATURE
<222> LOCATION: (1)..(1)
<223> OTHER INFORMATION: OCTREOTATE ATTACHED

<400> SEQUENCE: 50

Arg Gly Asp
1

<210> SEQ ID NO 51
<211> LENGTH: 12
<212> TYPE: PRT
<213> ORGANISM: Homo sapiens
<220> FEATURE:
<221> NAME/KEY: MISC_FEATURE
<222> LOCATION: (1)..(1)
<223> OTHER INFORMATION: CYPATE DYE ATTACHED
<220> FEATURE:
<221> NAME/KEY: MISC_FEATURE
<222> LOCATION: (5)..(5)
<223> OTHER INFORMATION: X = D-PHENYLALANINE
<220> FEATURE:
<221> NAME/KEY: MISC_FEATURE
<222> LOCATION: (6)..(11)
<223> OTHER INFORMATION: CYCLIC PEPTIDE
<220> FEATURE:
<221> NAME/KEY: MISC_FEATURE
<222> LOCATION: (8)..(8)
<223> OTHER INFORMATION: X=D-TRYPTOPHAN

<400> SEQUENCE: 51

Val Arg Gly Asp Xaa Cys Tyr Xaa Lys Thr Cys Thr
1               5                   10
```

```
<210> SEQ ID NO 52
<211> LENGTH: 6
<212> TYPE: PRT
<213> ORGANISM: Homo sapiens
<220> FEATURE:
<221> NAME/KEY: MISC_FEATURE
<222> LOCATION: (1)..(1)
<223> OTHER INFORMATION: CYPATE-3 DYE ATTACHED

<400> SEQUENCE: 52

Gly Arg Asp Ser Pro Lys
1               5

<210> SEQ ID NO 53
<211> LENGTH: 6
<212> TYPE: PRT
<213> ORGANISM: Homo sapiens
<220> FEATURE:
<221> NAME/KEY: MISC_FEATURE
<222> LOCATION: (1)..(1)
<223> OTHER INFORMATION: CYPATE-2 DYE ATTACHED

<400> SEQUENCE: 53

Gly Arg Asp Ser Pro Lys
1               5

<210> SEQ ID NO 54
<211> LENGTH: 6
<212> TYPE: PRT
<213> ORGANISM: Homo sapiens
<220> FEATURE:
<221> NAME/KEY: MISC_FEATURE
<222> LOCATION: (1)..(6)
<223> OTHER INFORMATION: CYCLIC PEPTIDE
<220> FEATURE:
<221> NAME/KEY: MISC_FEATURE
<222> LOCATION: (4)..(4)
<223> OTHER INFORMATION: X=D-PHENYLALANINE

<400> SEQUENCE: 54

Arg Gly Asp Xaa Val Lys
1               5

<210> SEQ ID NO 55
<211> LENGTH: 4
<212> TYPE: PRT
<213> ORGANISM: Homo sapiens
<220> FEATURE:
<221> NAME/KEY: MISC_FEATURE
<222> LOCATION: (1)..(1)
<223> OTHER INFORMATION: Xaa = between 1 & 10 amino acids selected from
     Gly, Ser, Asn, Gln, Asp, Glu, Lys, Arg, Thr, Tyr, Cys and His
<220> FEATURE:
<221> NAME/KEY: MISC_FEATURE
<222> LOCATION: (1)..(4)
<223> OTHER INFORMATION: are bound to R1 & R2 where R1 & R2 are
     independently selected from the group consisting of an imaging
     agent, a treatment agent, H, hydroxyl, hydrocarbyl, &
     subsituted hydrocarbyl, provided at least one of R1 & R2 is an
     imaging agenet or a treatment agent
<220> FEATURE:
<221> NAME/KEY: MISC_FEATURE
<222> LOCATION: (1)..(4)
<223> OTHER INFORMATION: wherein Xaa Arg Asp Xaa is repeated between 1
     and 10 times
<220> FEATURE:
<221> NAME/KEY: MISC_FEATURE
<222> LOCATION: (4)..(4)
```

-continued

```
<223> OTHER INFORMATION: Xaa = between 1 & 10 amino acids selected from
      Gly, Ser, Asn, Gln, Asp, Glu, Lys, Arg, Thr, Tyr, Cys and His

<400> SEQUENCE: 55

Xaa Arg Asp Xaa
1
```